United States Patent [19]

Takiguchi et al.

[11] Patent Number: 5,244,596
[45] Date of Patent: Sep. 14, 1993

[54] MESOMORPHIC COMPOUND FOR USE IN LIQUID CRYSTAL COMPOSITION AND LIQUID CRYSTAL DEVICE AND DISPLAY APPARATUS USING SAME

[75] Inventors: Takao Takiguchi, Tokyo; Takashi Iwaki, Machida; Takeshi Togano, Yokohama; Yoko Yamada; Shinichi Nakamura, both of Atsugi, all of Japan

[73] Assignee: Canon Kabushiki Kaisha, Tokyo, Japan

[21] Appl. No.: 716,840

[22] Filed: Jun. 17, 1991

[30] Foreign Application Priority Data

Jun. 19, 1990 [JP] Japan .................................. 2-161918
Jan. 31, 1991 [JP] Japan .................................. 3-011018

[51] Int. Cl.$^5$ .................... C09K 19/34; C07D 401/00; C07D 263/52
[52] U.S. Cl. .................. 252/299.61; 252/299.62; 252/299.63; 252/299.67; 252/299.01; 546/192; 546/208; 546/269; 546/273; 548/215; 548/217; 548/221; 548/224; 548/237; 548/241; 548/243
[58] Field of Search ............ 252/299.1, 299.61, 299.62, 252/299.63, 299.67; 544/242, 298, 335; 546/192, 198, 200, 208, 269, 271, 272, 273; 548/122, 124, 215, 217, 221, 224, 237, 241, 243; 359/103

[56] References Cited

U.S. PATENT DOCUMENTS

| | | | |
|---|---|---|---|
| 4,367,924 | 1/1983 | Clark et al. | 350/334 |
| 5,034,151 | 7/1991 | Shinjo et al. | 252/299.6 |
| 5,190,690 | 3/1993 | Takiguchi et al. | 252/299.61 |

FOREIGN PATENT DOCUMENTS

| | | |
|---|---|---|
| 0393613 | 10/1990 | European Pat. Off. |
| 56-107216 | 8/1981 | Japan. |
| 58-004778 | 1/1983 | Japan. |

OTHER PUBLICATIONS

Gattermann, "Die Praxis des Organisden Chemikers", p. 214.
Adams et al., "J. Am. Chem. Soc.", vol. 63, p. 196 (1941).
Hein et al., "J. Am. Chem. Soc.", vol. 79 p. 427 (1957).
Kanaoka et al., "Chem. Pharm. Bull.", vol. 18, p. 587 (1970).
Schadt et al., "Applied Physics Letters", vol. 18, No. 4, pp. 127–128 (1971).
Pavluchenko et al., "Mol. Cryst. Liq. Cryst", vol. 37, pp. 35–36 (1976).
Chemical Abstracts, vol. 98, No. 21 (May 1983) 179360r.

*Primary Examiner*—Robert L. Stoll
*Assistant Examiner*—Shean C. Wu
*Attorney, Agent, or Firm*—Fitzpatrick, Cella, Harper & Scinto

[57] ABSTRACT

A mesomorphic compound represented by the following formula [I]:

$$R_1(X_1-A_1)_{n1}-X_2-\text{[benzoxazole]}-A_2-X_3-(A_3-X_4)_{n2}-R_2 \quad [I]$$

wherein $R_1$ and $R_2$ independently denote an alkyl group having 1–16 carbon atoms capable of having a substituent; $X_1$, $X_2$, $X_3$ and $X_4$ independently denote a single bond $$-O-, -OC-, -CO-, \text{ or } -C-;$$
$$\quad\quad\quad \|\quad\quad\|\quad\quad\quad\|$$
$$\quad\quad\quad O\quad\quad O\quad\quad\quad O$$

$A_1$, $A_2$ and $A_3$ independently denote (structures shown)

(Abstract continued on next page.)

-continued
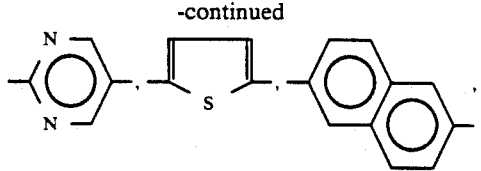
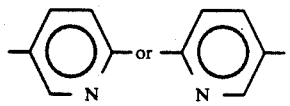
; $X_5$ and $X_6$ independently denote hydrogen atom, fluorine, chlorine, bromine, $CH_3$, CN or $CF_3$; $n_1$ and $n_2$ are 0 or 1, with provisos that (1) $X_2$ cannot be a single bond when $n_1$ is 0, (2) $X_3$ cannot be a single bond when $N_2$ is 1 and (3) at least one of $X_2$ and $X_3$ denotes
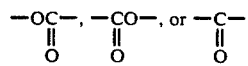
when both $n_1$ and $n_2$ is O and $A_2$ denote
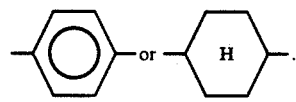
23 Claims, 4 Drawing Sheets

MESOMORPHIC COMPOUND FOR USE IN LIQUID CRYSTAL COMPOSITION AND LIQUID CRYSTAL DEVICE AND DISPLAY APPARATUS USING SAME

BACKGROUND OF THE INVENTION

1. Field of the Invention

The present invention relates to a novel mesomorphic compound which may be used in a liquid crystal composition as well as liquid crystal devices apparatus and display methods using the same. In particular, the present invention relates to a novel mesomorphic compound and a liquid crystal composition, etc. with improved responsiveness to an electric field.

2. Related Background Art

Previously, liquid crystal materials have been used in electro-optical devices in various applications. Many such liquid crystal devices have used twisted nematic (TN) type liquid crystals, such as those shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices utilize the dielectric effect wherein dielectric anisotropy causes in which the aligment of the average molecular axis of a liquid crystal to be directed in a specific direction in response to an applied electric field. However, the accepted lower limit of response speed of TN devices is on the order of milliseconds, which is considered to be too slow for many uses. Moreover, while the simple matrix driving system (wherein scanning electrodes and signal electrodes are arranged in a matrix which is used by a multiplex driving scheme in which an address signal is sequentially, periodically and selectively applied to the scanning electrodes and prescribed data signals are selectively applied in parallel to the signal electrodes in synchronism therewith) is most promising for large-area flat displays in terms of cost, productivity, etc., the electric field applied to TN liquid crystal regions with a matrix driving system where a scanning electrode is selected and signal electrodes are not selected, or where a scanning electrode is not selected and a signal electrode is selected ("half-selected points") may cause image defects. In particular, if the difference between the voltage applied to the selected points and the voltage applied to the half-selected points is sufficiently large, and the voltage threshold (the voltage level required for allowing liquid crystal molecules to be aligned or be oriented perpendicular to an electric field) is set to a value therebetween, the TN display devices operate normally.

However, as the number (N) of scanning lines increases, a time (duty ratio) during which an effective electric field is applied to one selected point when a whole image area (corresponding to one frame) is scanned decreases with a ratio of 1/N. Accordingly, as the number of scanning lines becomes greater, the difference of the voltage values applied to a selected point and non-selected points when scanning is repeated decreases. As a result, this leads to drawbacks including lowering of image contrast or interference (crosstalk). These phenomena are regarded as essentially unavoidable when repeatedly driving liquid crystal materials which are not bistable (i.e. those materials wherein liquid crystal molecules are stably oriented horizontally with respect to the electrode surface and oriented vertically with respect to the electrode surface only when an electric field is applied) using a time storage effect.

In an attempt to overcome the above drawbacks, driving methods such as the voltage averaging method [Fundamentals and Applications of Liquid Crystals, Ohm. April 1979], the two-frequency driving method [Latest technology of Liquid Crystals. Kogyochosaka; September 1984], the multiple matrix method [Liquid Crystals. Applications, Baifukan. July 1985], etc. have been proposed. However, no method is sufficient actually to overcome these drawbacks. As a result, development of TN devices with large image areas (or high display element packaging densities) is delayed because it is difficult to sufficiently increase the number of scanning lines.

To overcome drawbacks with such prior art liquid crystal devices, the use of bistable liquid crystal devices has been proposed by Clark and Lagerwall (e.g. Japanese Laid-Open Patent Appln. No. 56-107216, U.S. Pat. No. 4,367,924, etc.). In this instance, bistable, ferroelectric liquid crystals having chiral smectic C-phase (SmC*) or H-phase (SmH*) are generally used which assumed different states with respect to the polarity of an applied electric field. Accordingly, these bistable liquid crystal materials and devices differ from optical modulation devices which use TN liquid crystals since the bistable liquid crystal molecules are oriented to first and second optically stable states respectively by one and the other electric field vectors. Moreover, the bistable liquid crystal has the further difference in that the two stable states which are assumed in response to an applied electric field are retained even in the absence of that electric field.

In addition to their bistability characteristic, ferroelectric liquid crystal ("FLC") materials also exhibit crystal an excellent high-speed responsiveness. This is because the spontaneous polarization of the ferroelectric liquid crystal and an applied electric field directly interact with each other to induce transition of orientation states. The resulting response speed is faster by 3 to 4 magnitudes than a response speed which is solely due to the interaction between dielectric anisotropy and an electric field.

Thus, a ferroelectric liquid crystal has excellent characteristics, and by making use of these properties, it is potentially possible to provide essential improvements to many of the above-mentioned problems concerning conventional TN-type devices. Particularly, the successful application of an FLC to a high-speed optical shutter, a high density display and a large picture display are all expected. For this reason, extensive research has been undertaken with respect to liquid crystal materials showing ferroelectricity.

However, ferroelectric liquid crystal materials developed heretofore cannot be said to satisfy optimal characteristics required for a liquid crystal devices including low-temperature operation characteristic, high-speed responsiveness, etc. Concerning deficiencies in response time $\tau$, the following relationship exists: $\tau = \eta/(Ps \cdot E)$, where E is an applied voltage, Ps is the magnitude of spontaneous polarization and $\eta$ is viscosity. Accordingly, a high response speed can be obtained by any of (a) increasing the spontaneous polarization (b) lowering the viscosity, or (c) increasing the applied voltage. In practice, however, the driving voltage has a certain upper limit in view of driving with IC, etc., and should desirably be as low as possible. Accordingly, it is really feasible only to lower the viscosity or increase the spontaneous polarization.

A ferroelectric chiral smectic liquid crystal having a large spontaneous polarization generally provides in a cell a large internal electric field due to the spontaneous polarization. This internal electric field is liable to pose many constraints on the construction of a bistable device. [Ferroelectronics. 1988, Vol. 85. pp. 255-264]. Further, an excessively large spontaneous polarization often accompanies an increase in viscosity, so that a noticeable increase in response speed may not be achieved. Moreover, since response speed changes by a factor of about 20 over a typical operation temperature range of 5-40° C., response speed variance actually exceeds the range which is controllable by manipulating driving voltage and frequency.

As described hereinabove, an optimal ferroelectric liquid crystal device therefore requires the availability of a chiral smectic phase liquid crystal composition which has a large spontaneous polarization, a low viscosity, a high-speed responsiveness and a response speed which depends minimally upon temperature.

SUMMARY OF THE INVENTION

An object of the present invention is to provide a mesomorphic compound for use in a liquid crystal composition, particularly a chiral smectic liquid crystal composition which can provide a practical ferroelectric liquid crystal device and apparatus with a high response speed and a smaller temperature-dependence of the response speed, and a display method using the same.

According to the present invention, there is provided a mesomorphic compound represented by the following Formula (I):

$$R_1\text{-}(X_1\text{-}A_1)_{\overline{n1}}\text{-}X_2\text{-}\underset{O}{\underset{\|}{\text{benzoxazole}}}\text{-}A_2\text{-}X_3\text{-}(A_3\text{-}X_4)_{\overline{n2}}\text{-}R_2 \quad [\text{I}]$$

wherein $R_1$ and $R_2$ independently denote an alkyl group having 1-16 carbon atoms capable of having a substituent; $X_1$, $X_2z$, $X_3$ and $X_4$ independently denote a single bond $$-O-, -OC-, -CO-, \text{ or } -C-;\\ \quad\quad\;\; \| \quad\;\; \| \quad\;\; \|\\ \quad\quad\;\; O \quad\;\; O \quad\;\; O$$

$A_1$, $A_2$ and $A_3$ independently denote

[ring structures with $X_6$ substituents, including phenyl, cyclohexyl (H), pyridyl, pyrimidyl, thiophene (S), and naphthyl groups]

[continued phenyl and pyridyl ring structures]

$X_5$ and $X_0$ independently denote hydrogen atom, fluorine, chlorine, bromine, $CH_3$, $CN$ or $CF_3$; and $n_1$ and $n_2$ are independently 0 or 1, with provisos that (1) $X_2$ cannot be a single bond when $n_1$ is 1, (2) $X_3$ cannot be a single bond when $n_2$ is 1 and (3) at least $X_3$ denotes $$-OC-, -CO-, \text{ or } -C-\\ \;\;\| \quad\;\; \| \quad\;\; \|\\ \;\;O \quad\;\; O \quad\;\; O$$

when both $n_1$ and $n_2$ are O and $A_2$ denotes

[phenyl or cyclohexyl (H) ring structure].

According to the present invention, there is further provided a liquid crystal composition comprising at least one of a mesomorphic compound of the Formula (I) as well as a liquid crystal device comprising a pair of opposed electrodes and the liquid crystal composition described above disposed there between and a display apparatus comprising the same.

Further according to the present invention, there is provided a display method using the liquid crystal composition containing a mesomorphic compound described above.

These and other objects, features and advantages of the present invention will become more apparent upon a consideration of the following description of the preferred embodiments of the present invention taken in conjunction with the accompanying drawings.

DETAILED DESCRIPTION OF THE PREFERRED EMBODIMENTS

Figure 1:
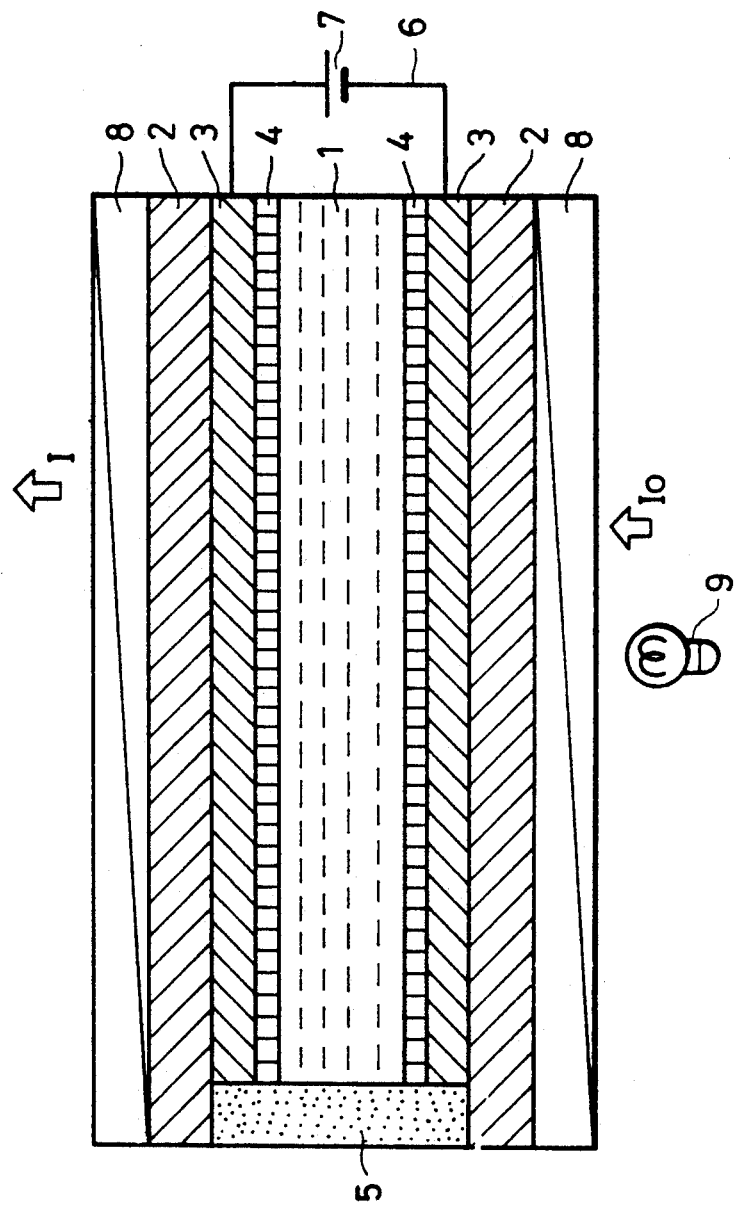
FIG. 1 is a partial cross-sectional view of a liquid crystal cell using a liquid crystal composition assuming a chiral smectic phase.

Preferred example of the mesomorphic compounds represented by the above-mentioned general Formula (I) include those shown by the following structural Formulae [Ia]-[Ik].

$$R_1\text{-}X_2\text{-}\underset{O}{\underset{\|}{\text{benzoxazole}}}\text{-}\underset{X_6}{\overset{X_6}{\text{phenyl}}}\text{-}X_3\text{-}A_3\text{-}X_4)_{\overline{n2}}\text{-}R_2 \quad [\text{Ia}]$$

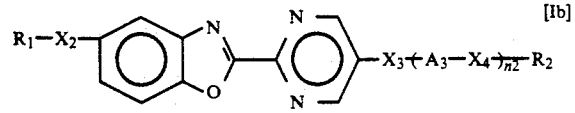 [Ib]

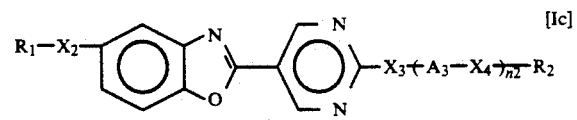 [Ic]

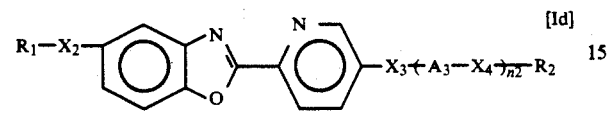 [Id]

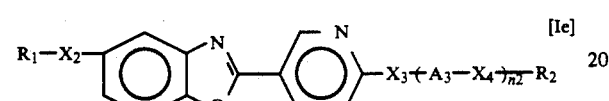 [Ie]

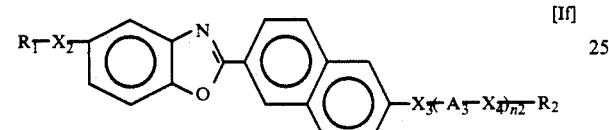 [If]

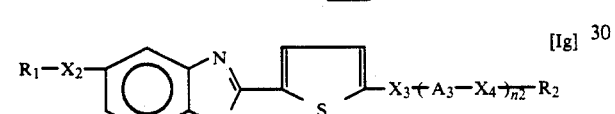 [Ig]

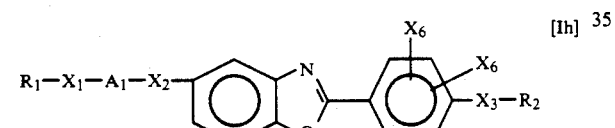 [Ih]

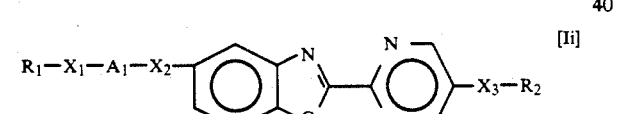 [Ii]

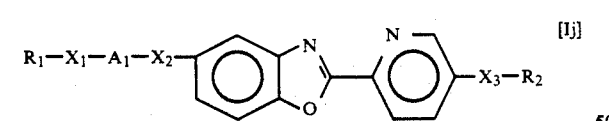 [Ij]

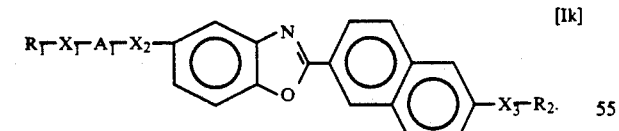 [Ik]

More preferred examples of the mesomorphic compounds shown by the above Formulae [Ia]–[Ik] include those shown by the following Formulae [Iaa]–[Ihb].

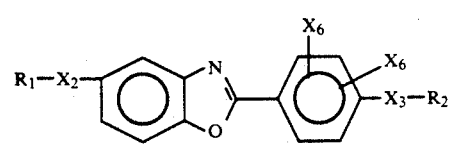 [Iaa]

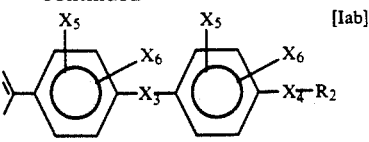 [Iab]

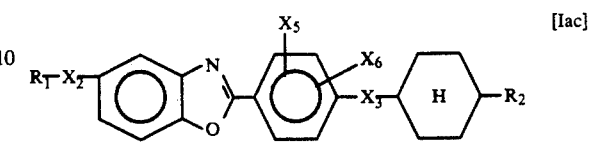 [Iac]

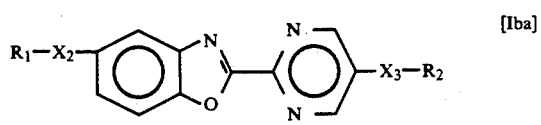 [Iba]

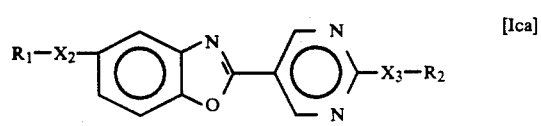 [Ica]

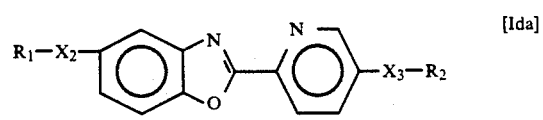 [Ida]

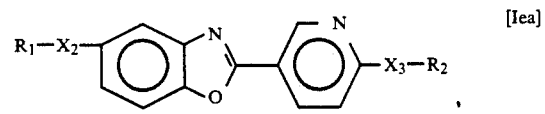 [Iea]

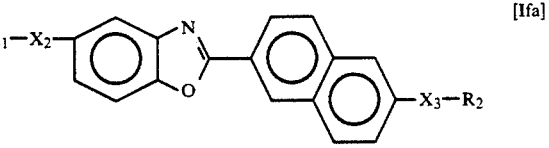 [Ifa]

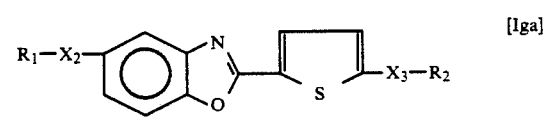 [Iga]

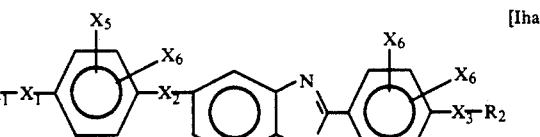 [Iha]

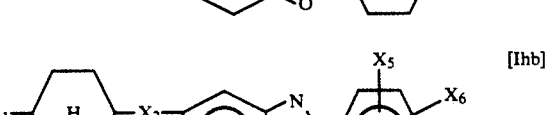 [Ihb]

wherein two sets of $X_5$ and $X_6$ attached to different benzene rings in the formulas [Iab] and [Iha] may be same of different.

Further, preferred example of $R_1$ and $R_2$ include those represented by the following groups (i) to (iv):

(i) an n-alkyl group having 1-15 carbon atoms, and preferably 4-12 carbon atoms;

(ii) 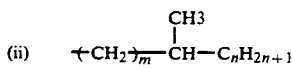

wherein m is integer of 0-6, n is an integer of 1-8 and the group may be optically active;

(iii) 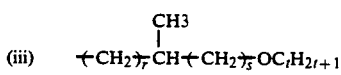

wherein n is an integer of 0-6, S is 0 or 1 and t is an integer of 1-12 and the group may be optically active;

(iv) 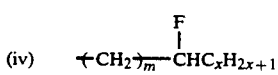

wherein m is 0 or 1 and X is an integer of 4-14. Preferred examples of $X_5$ and $X_6$ include hydrogen, F, CN, $CH_3$ and $CF_3$, more preferably hydrogen, F and $CF_3$.

Different liquid crystal materials containing a benzooxazole ring have been shown in A. I. Pavlucheko et al., "Mol. Cryst. Liq. Cryst.", 37. 35-46 (1976) and in Japanese Laid-Open Patent Application No. 58-4778. However, we have studied ferroelectric chiral smectic liquid crystal compositions containing a benzooxazole derivative shown by Formula [I] of the present invention and found an improved operation characteristic at a lower temperature and decreased temperature dependence of response speed.

General synthesis of the mesomorphic compound represented by the above-mentioned Formula [I] is shown below.

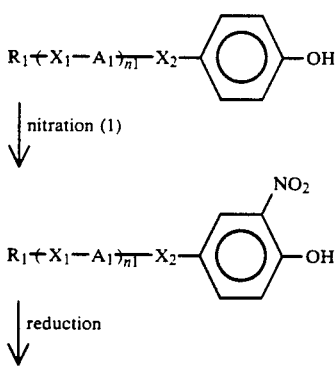

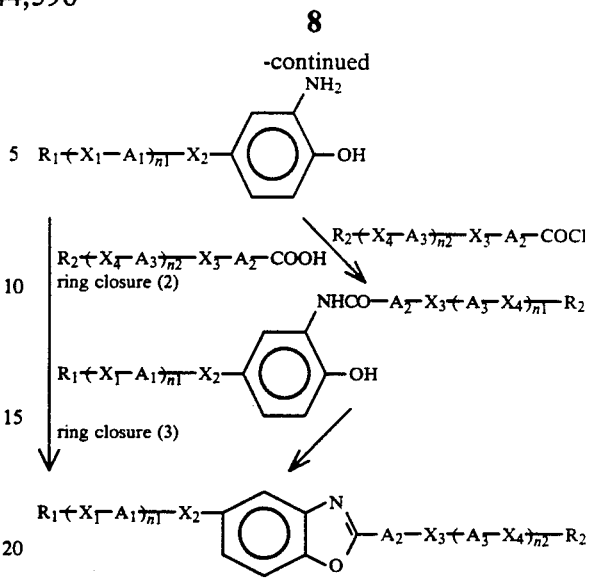

Methods of nitration of phenols (Step 1) are shown in L. Gattermann, "Die Praxis des Organischen Chemikers" p. 214 and R. Adams et al., "J.Am.Chem. Soc.", 63. 196 (1941).

Methods of ring closure (Steps 2 and 3) of O-aminophenols to benzooxazole ring are shown in D. W. Hein et al., "J.Am.Chem.Soc.", 79, 427 (1957) and Y. Kanaoka et al. "Chem.Pharm.Bull," 18, 587 (1970).

In a case where $X_2$ and $X_3$ are

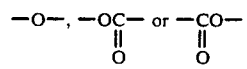

it is possible to form a group of $-X_2-(A_1-X_1)_{n1}R_1$ and $-X_2-(A_3-X_4)_{n2}R_2$ by adding a detachable protective group to hydroxyl group or carboxyl group combined with 4-place of nitrophenol or $A_2$, followed by eliminating the protective group after ring closure is effected to form a benzooxazole ring.

It is also possible to form a group of $-X_2-(A_1-X_1)_{n1}R_1$ and $-X_2-(A_3-X_4)_{n2}R_2$ by combining nitro group or acetyl group, (which can be modified into hydroxyl group or carboxyl group) with 4-place of nitrophenol or $A_2$, followed by modifying these group into hydroxyl group or carboxyl group after ring closure is effected to form a benzooxazole ring.

Specific examples of the mesomorphic compounds represented by the above-mentioned Formula [I]include those shown by the following structural formulae.

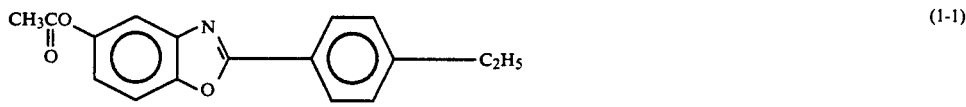

(1-1)

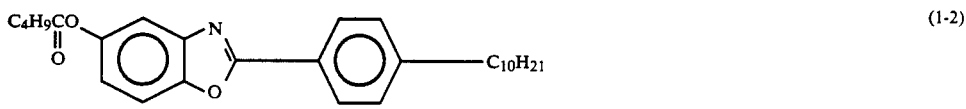

(1-2)

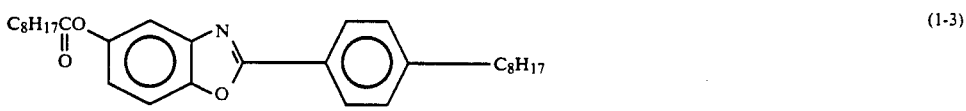

(1-3)

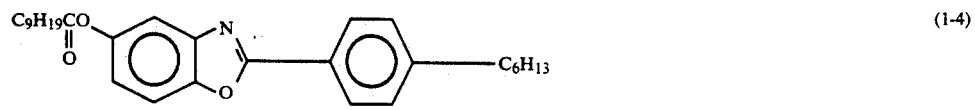 (1-4)
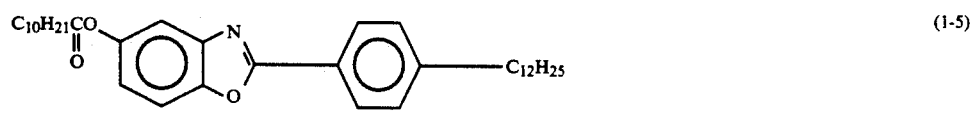 (1-5)
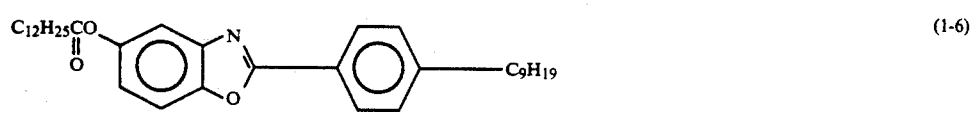 (1-6)
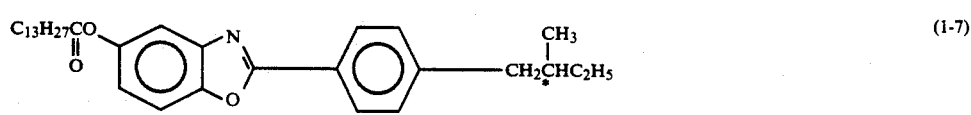 (1-7)
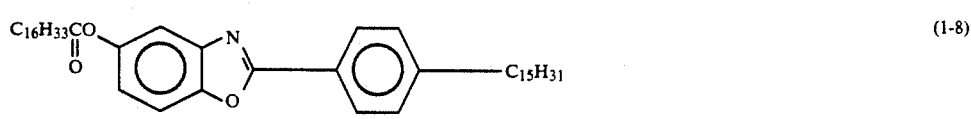 (1-8)
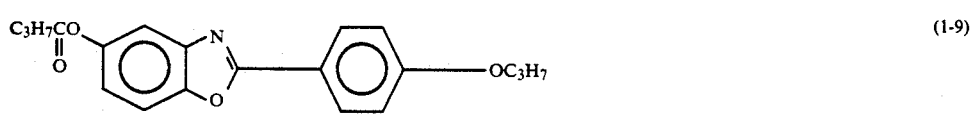 (1-9)
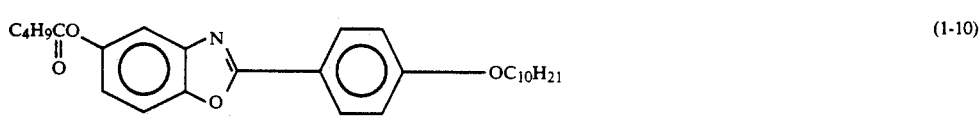 (1-10)
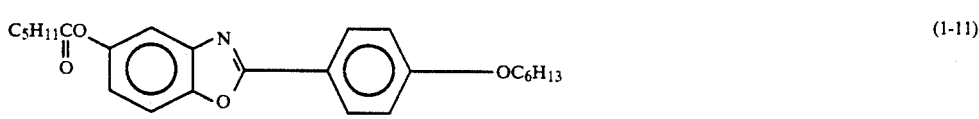 (1-11)
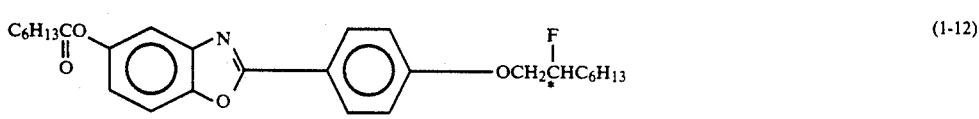 (1-12)
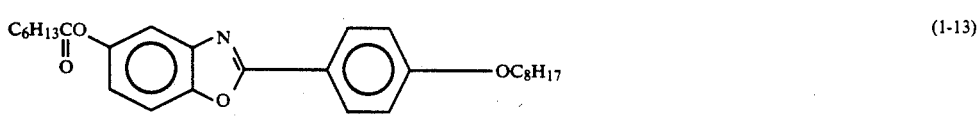 (1-13)
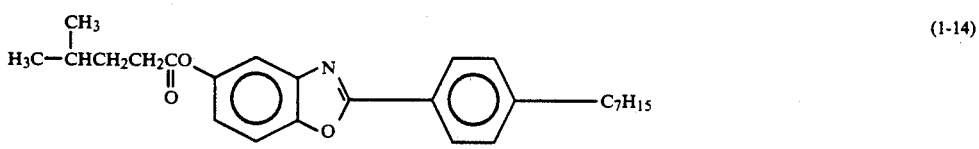 (1-14)
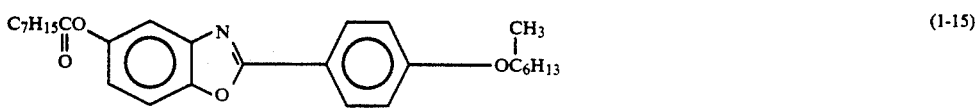 (1-15)
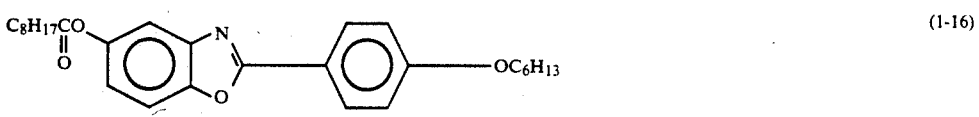 (1-16)

-continued
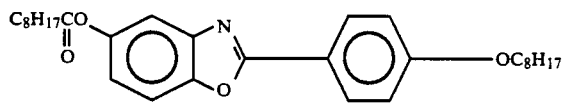 (1-17)
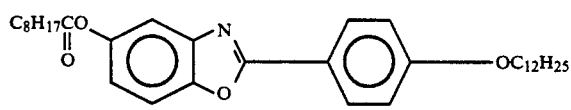 (1-18)
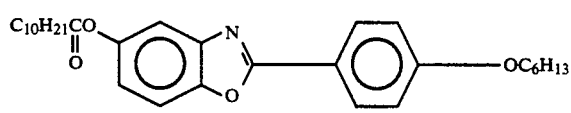 (1-19)
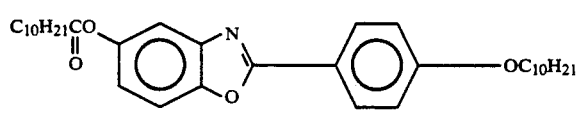 (1-20)
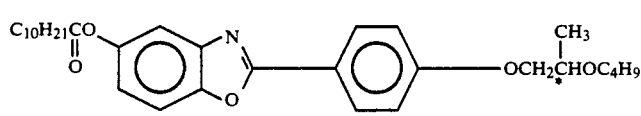 (1-21)
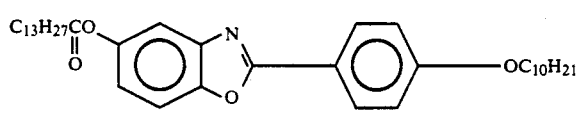 (1-22)
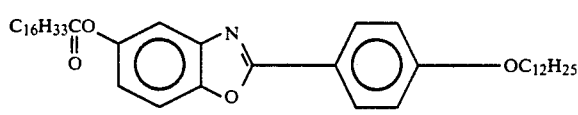 (1-23)
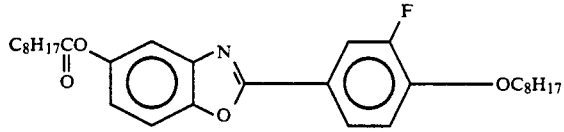 (1-24)
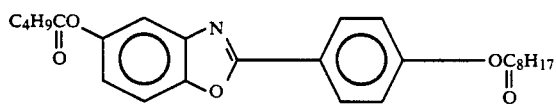 (1-25)
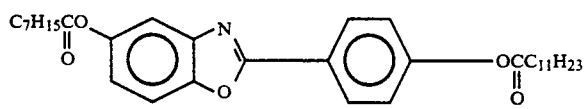 (1-26)
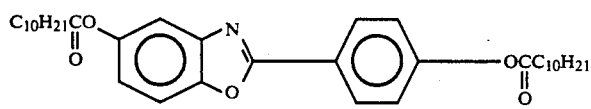 (1-27)
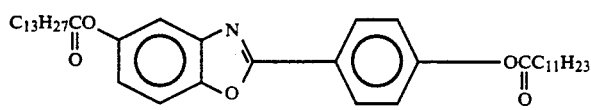 (1-28)
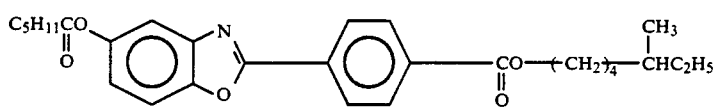 (1-29)

-continued
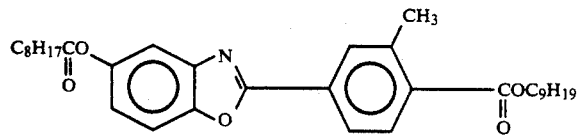 (1-30)
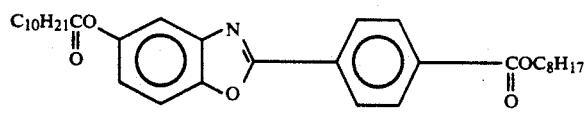 (1-31)
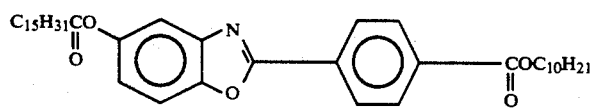 (1-32)
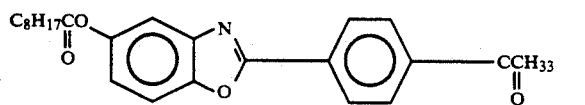 (1-33)
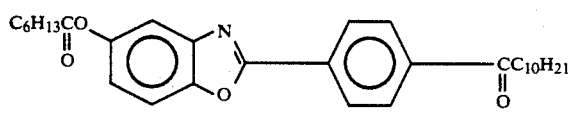 (1-34)
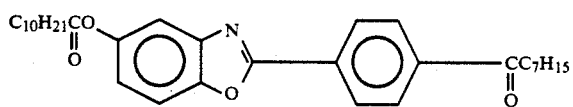 (1-35)
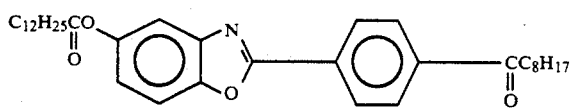 (1-36)
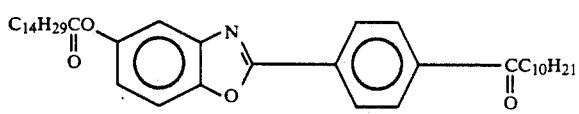 (1-37)
 (1-38)
 (1-39)
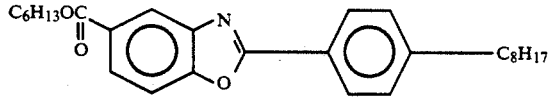 (1-40)
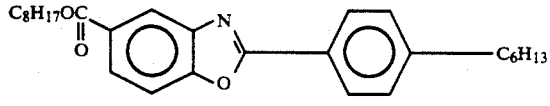 (1-41)
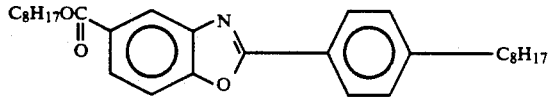 (1-42)
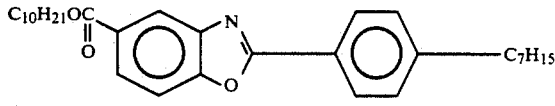

-continued
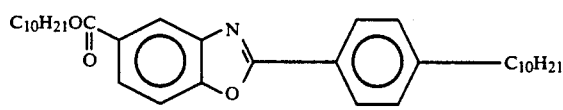 (1-43)
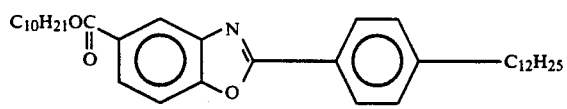 (1-44)
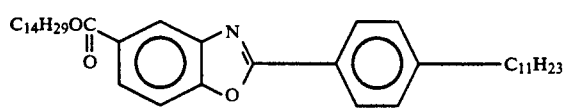 (1-45)
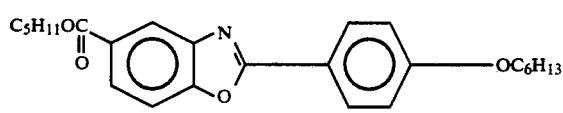 (1-46)
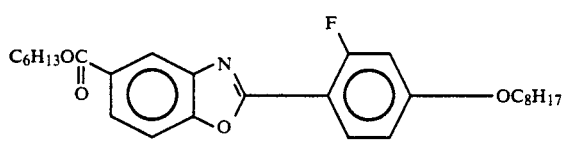 (1-47)
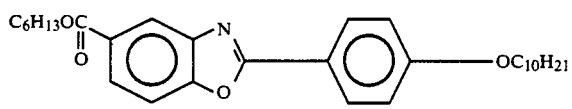 (1-48)
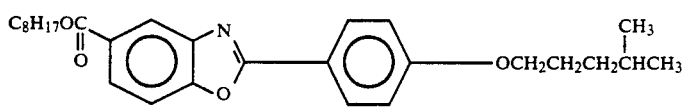 (1-49)
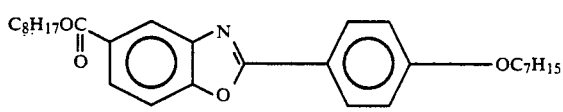 (1-50)
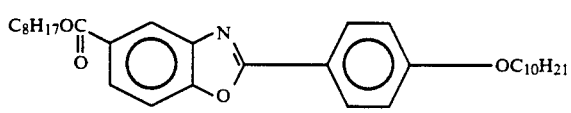 (1-51)
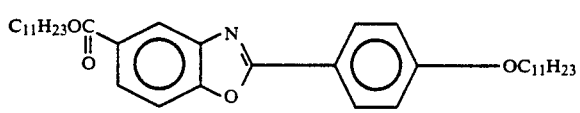 (1-52)
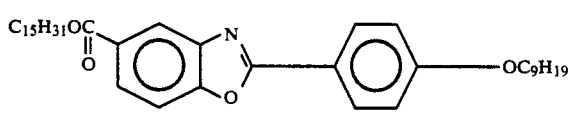 (1-53)
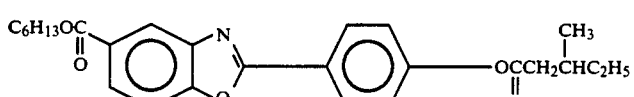 (1-54)
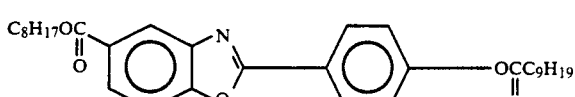 (1-55)

-continued
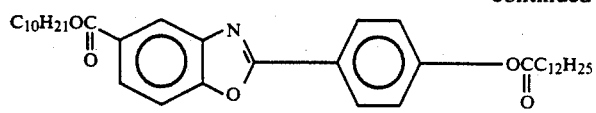 (1-56)
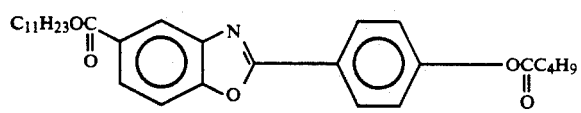 (1-57)
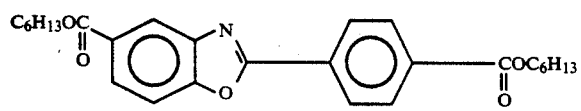 (1-58)
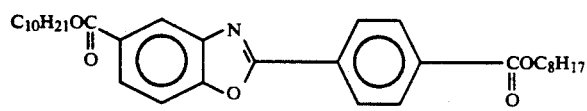 (1-59)
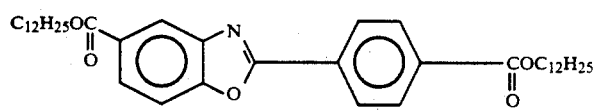 (1-60)
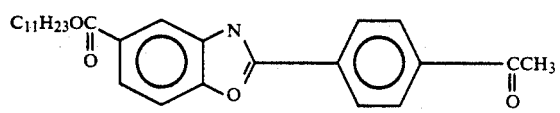 (1-61)
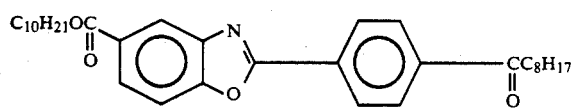 (1-62)
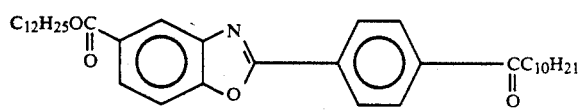 (1-63)
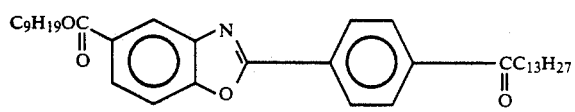 (1-64)
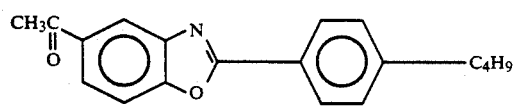 (1-65)
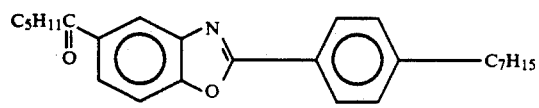 (1-66)
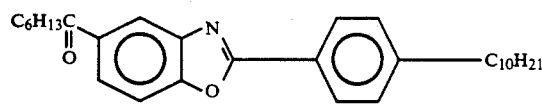 (1-67)
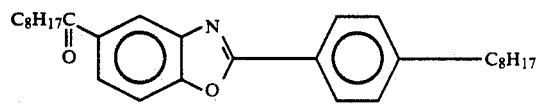 (1-68)
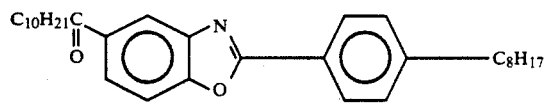 (1-69)

-continued
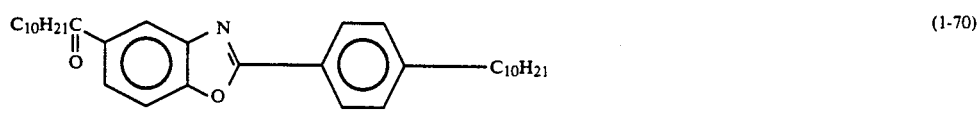 (1-70)
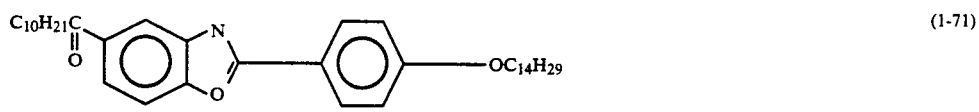 (1-71)
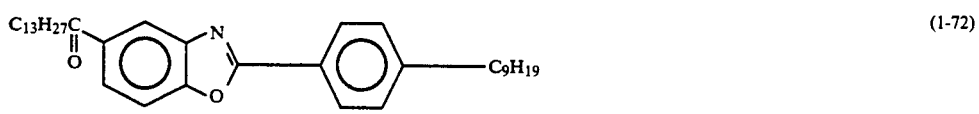 (1-72)
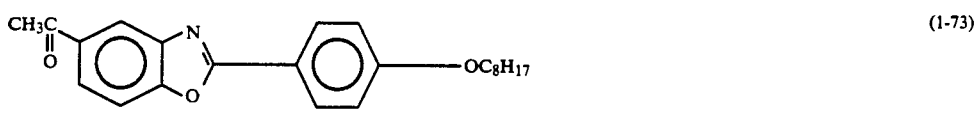 (1-73)
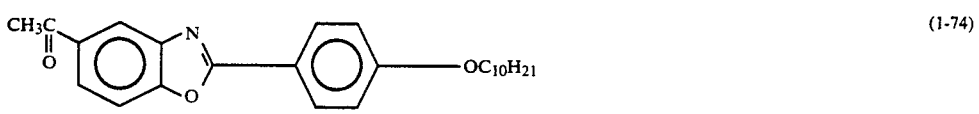 (1-74)
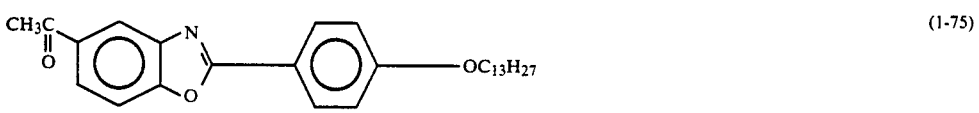 (1-75)
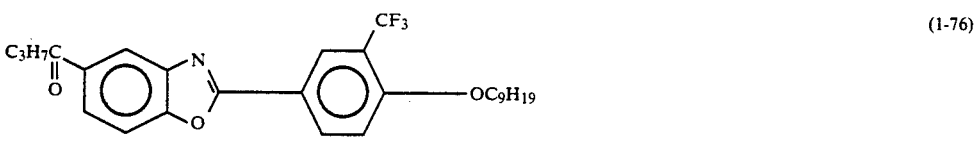 (1-76)
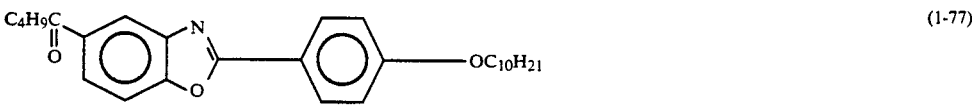 (1-77)
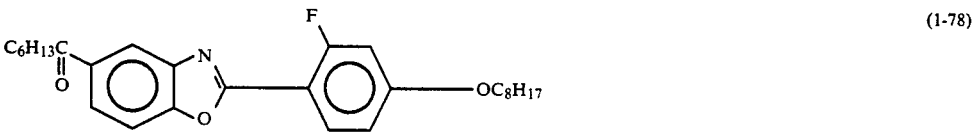 (1-78)
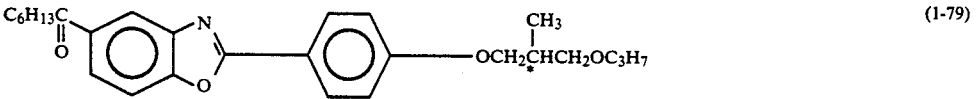 (1-79)
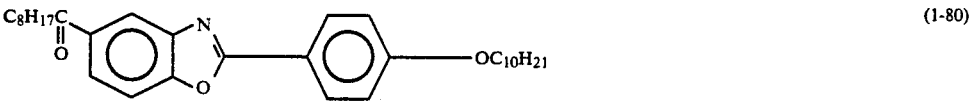 (1-80)
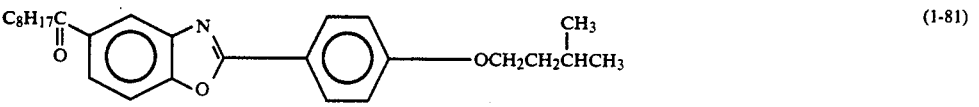 (1-81)
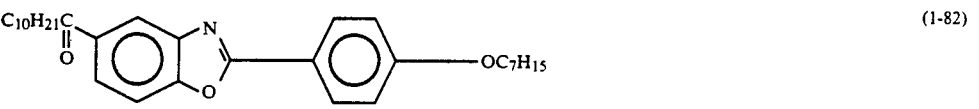 (1-82)

-continued
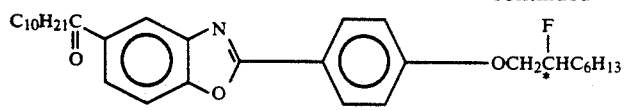 (1-83)
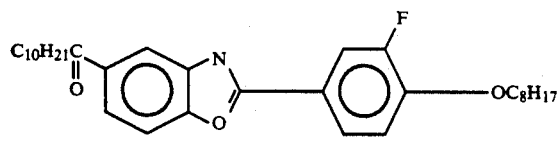 (1-84)
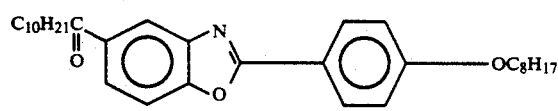 (1-85)
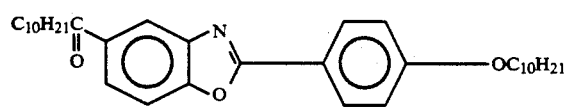 (1-86)
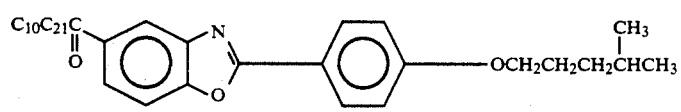 (1-87)
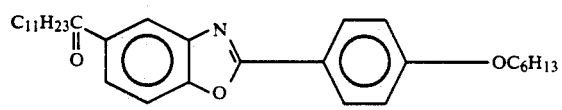 (1-88)
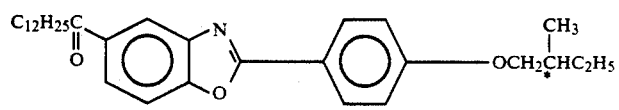 (1-89)
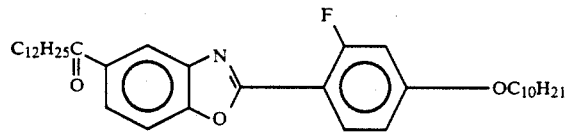 (1-90)
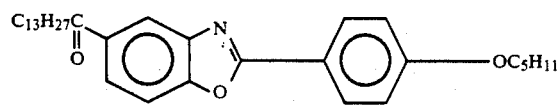 (1-91)
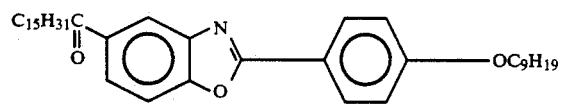 (1-92)
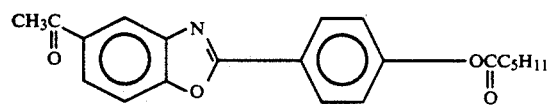 (1-93)
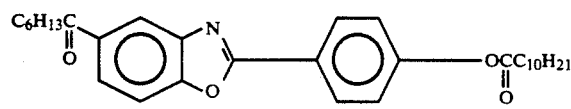 (1-94)
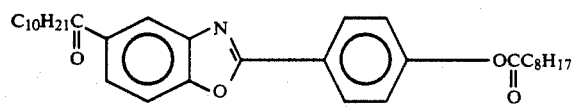 (1-95)

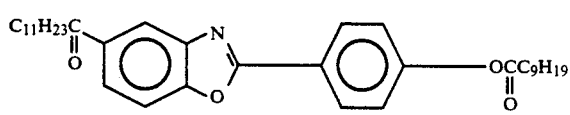 (1-96)
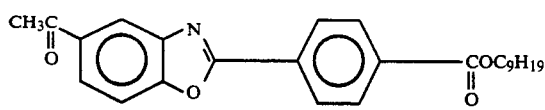 (1-97)
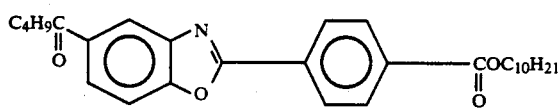 (1-98)
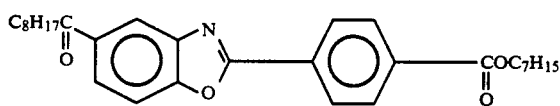 (1-99)
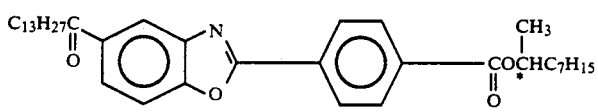 (1-100)
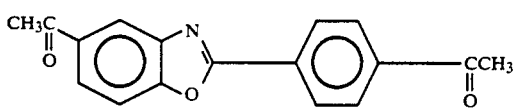 (1-101)
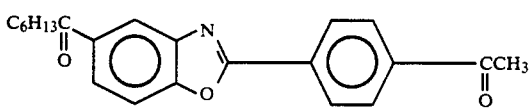 (1-102)
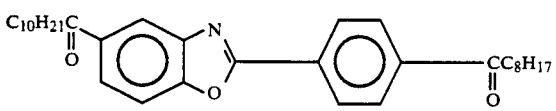 (1-103)
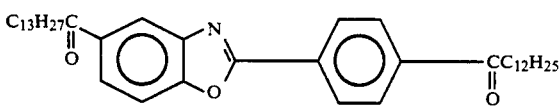 (1-104)
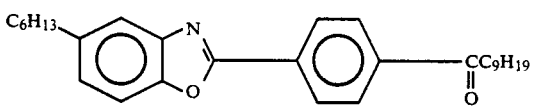 (1-105)
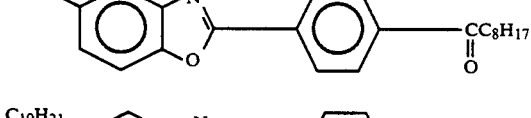 (1-106)
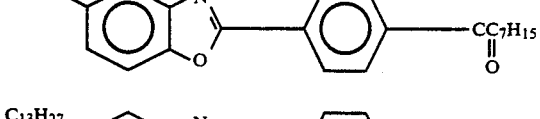 (1-107)
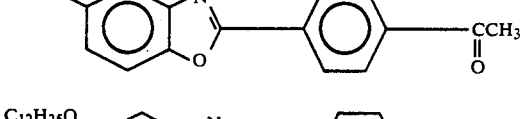 (1-108)
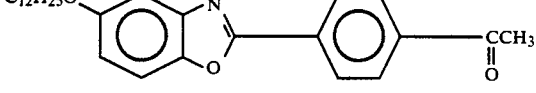 (1-109)

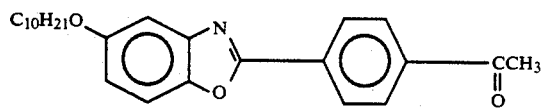
(1-110)
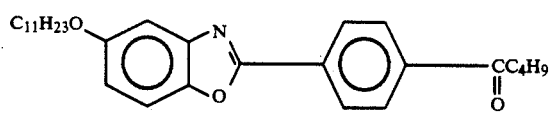
(1-111)
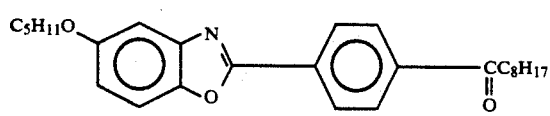
(1-112)
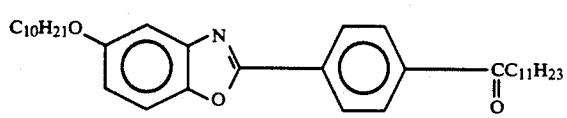
(1-113)
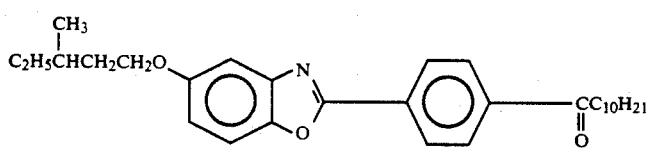
(1-114)
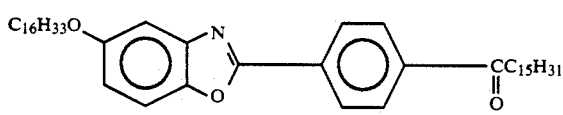
(1-115)
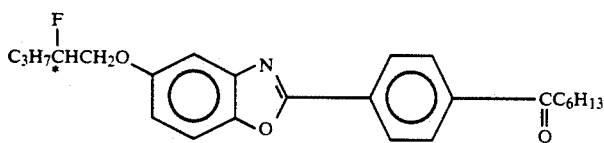
(1-116)
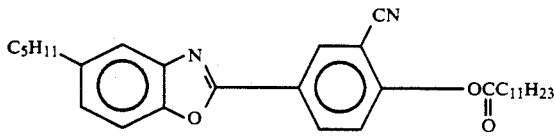
(1-117)
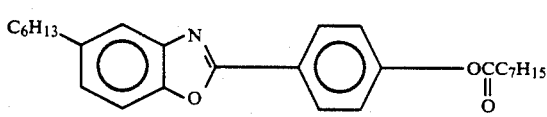
(1-118)
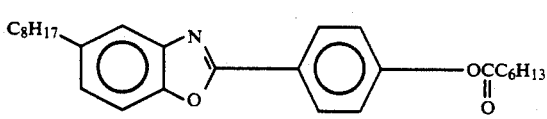
(1-119)
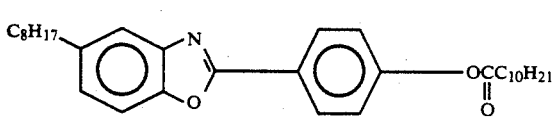
(1-120)
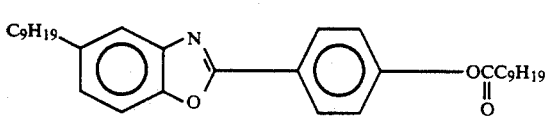
(1-121)
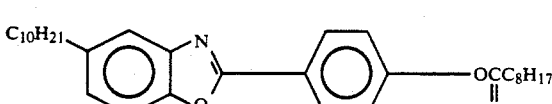
(1-122)

-continued
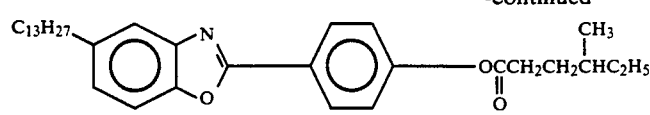 (1-123)
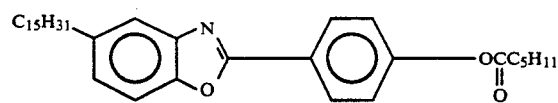 (1-124)
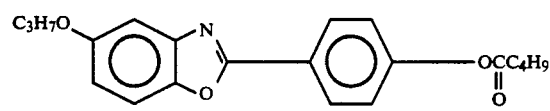 (1-125)
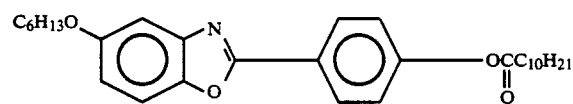 (1-126)
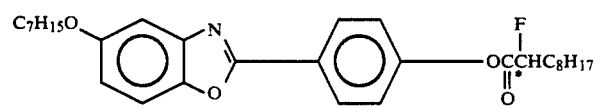 (1-127)
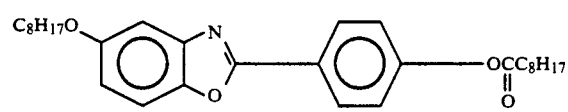 (1-128)
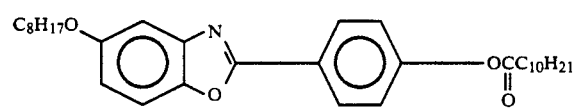 (1-129)
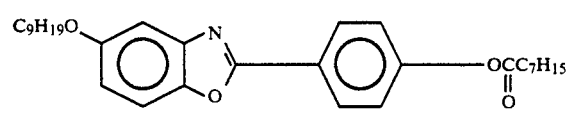 (1-130)
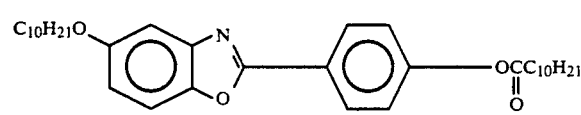 (1-131)
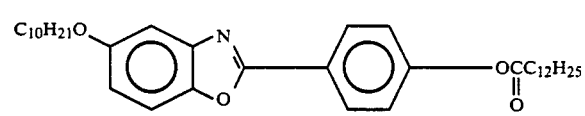 (1-132)
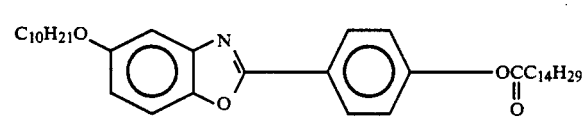 (1-133)
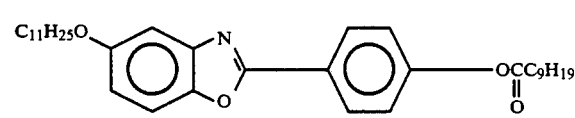 (1-134)
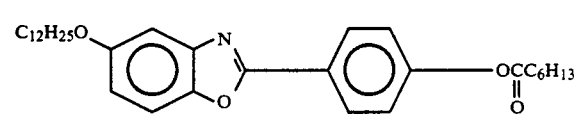 (1-135)
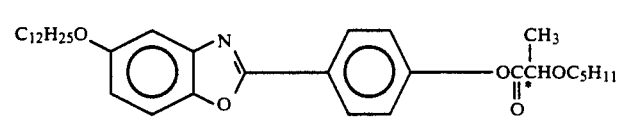 (1-136)

-continued
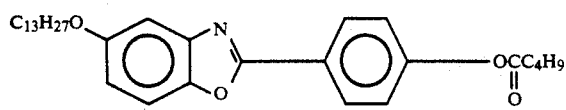 (1-137)
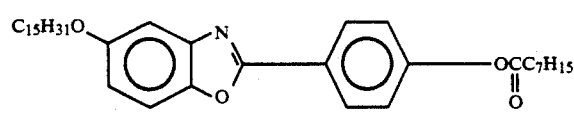 (1-138)
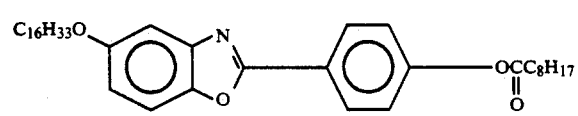 (1-139)
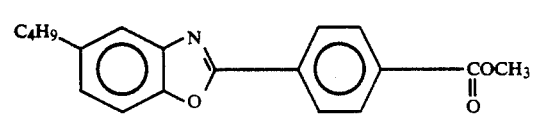 (1-140)
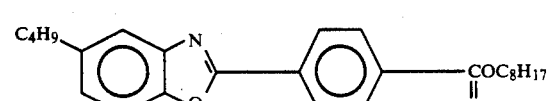 (1-141)
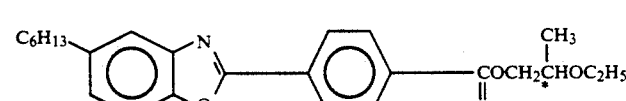 (1-142)
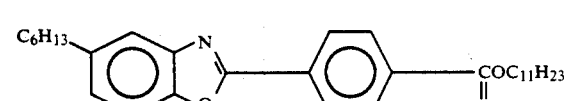 (1-143)
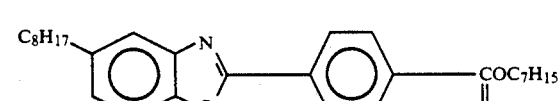 (1-144)
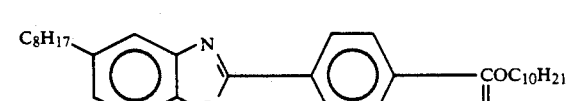 (1-145)
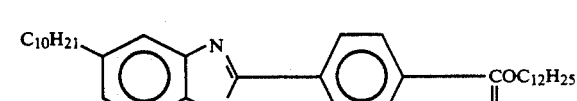 (1-146)
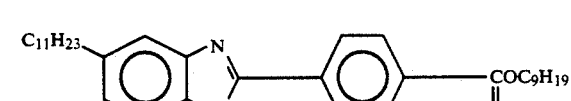 (1-147)
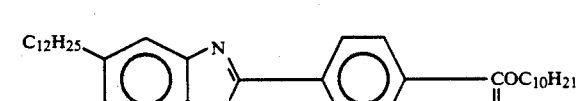 (1-148)
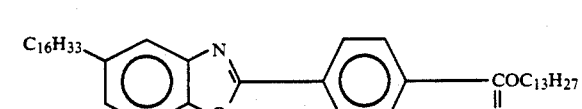 (1-149)

-continued
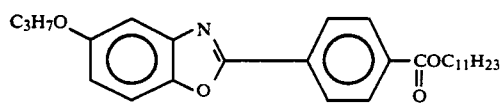 (1-150)
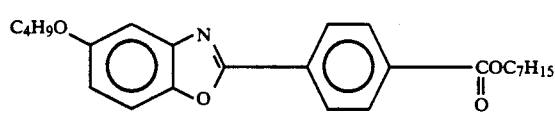 (1-151)
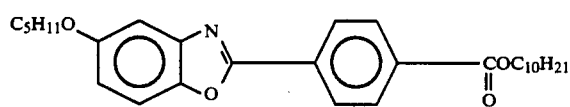 (1-152)
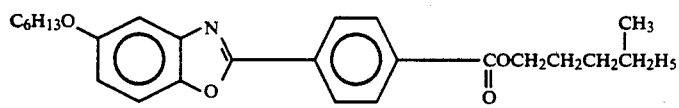 (1-153)
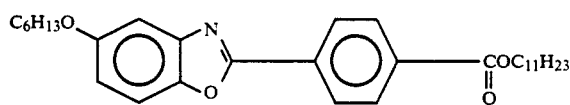 (1-154)
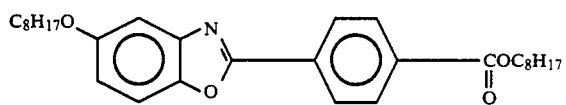 (1-155)
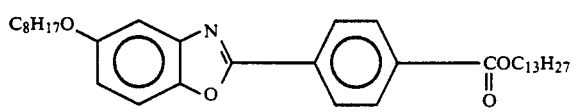 (1-156)
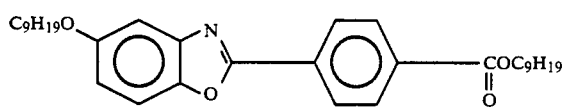 (1-157)
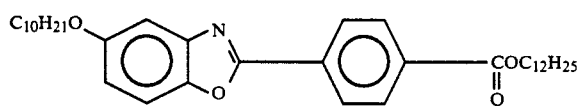 (1-158)
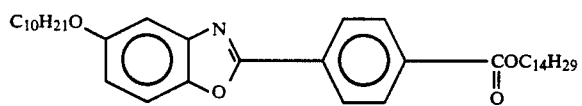 (1-159)
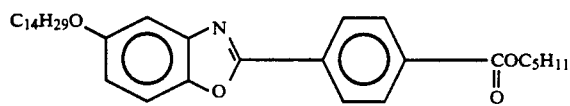 (1-160)
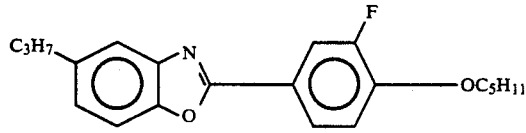 (1-161)
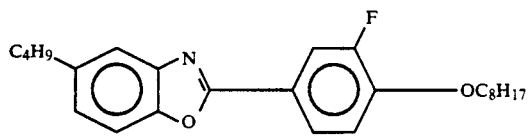 (1-162)

-continued
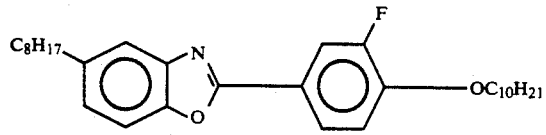 (1-163)
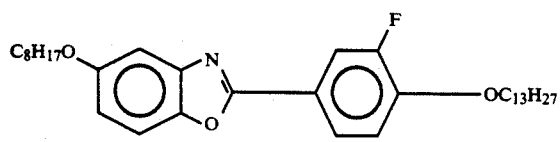 (1-164)
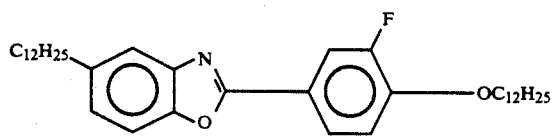 (1-165)
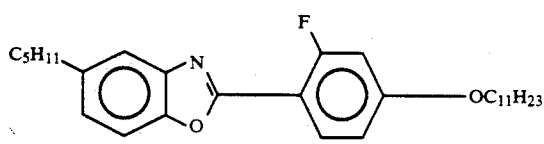 (1-166)
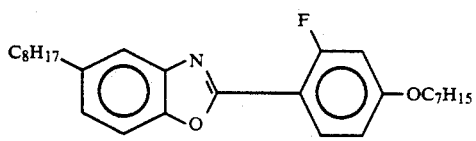 (1-167)
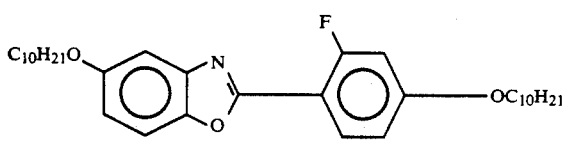 (1-168)
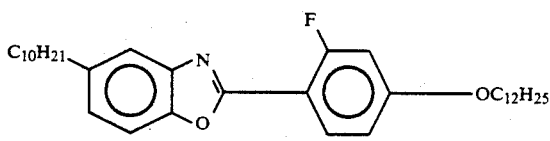 (1-169)
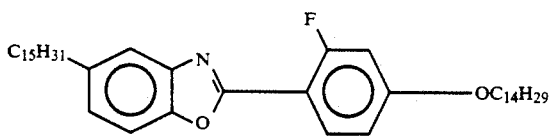 (1-170)
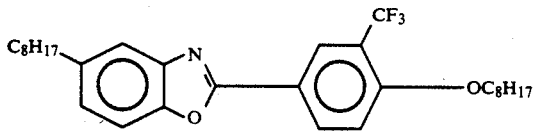 (1-171)
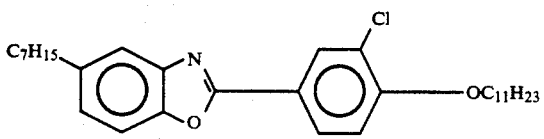 (1-172)
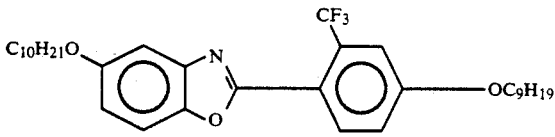 (1-173)

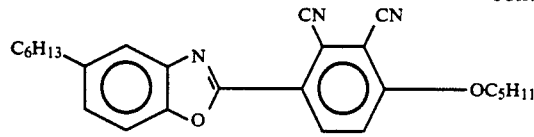
(1-174)
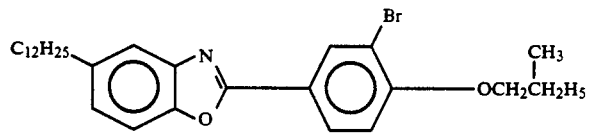
(1-175)
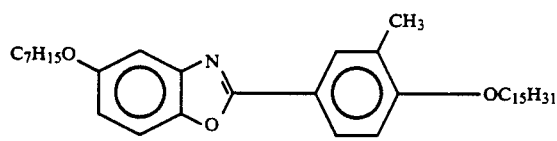
(1-176)
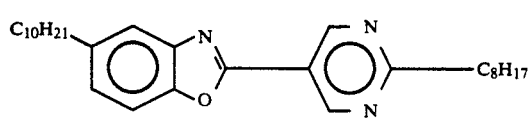
(1-177)
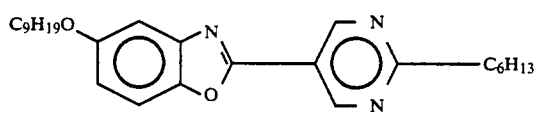
(1-178)
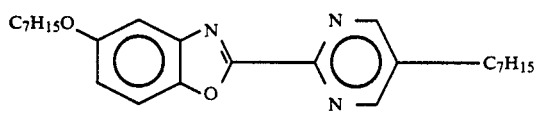
(1-179)
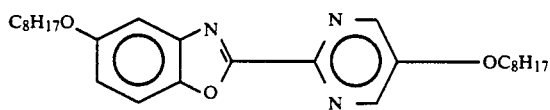
(1-180)
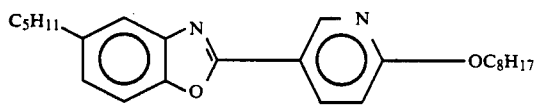
(1-181)
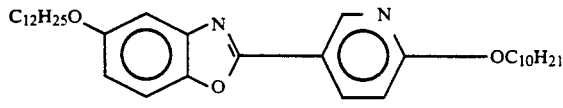
(1-182)
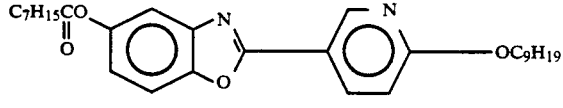
(1-183)
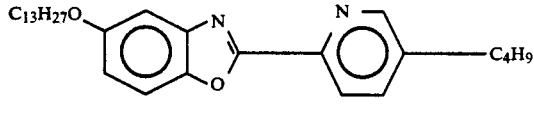
(1-184)
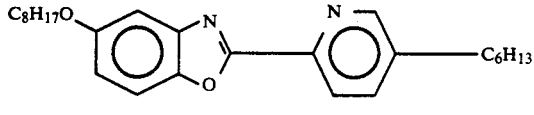
(1-185)
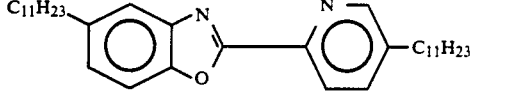
(1-186)

-continued
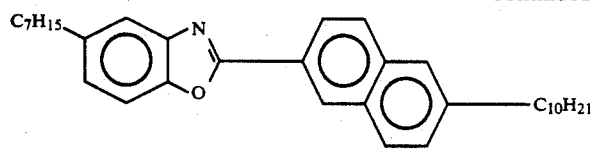 (1-187)
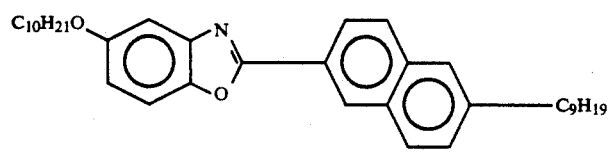 (1-188)
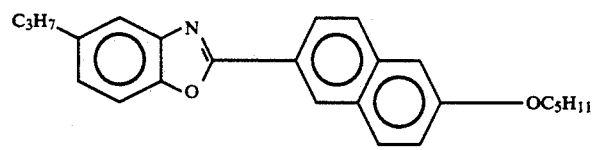 (1-189)
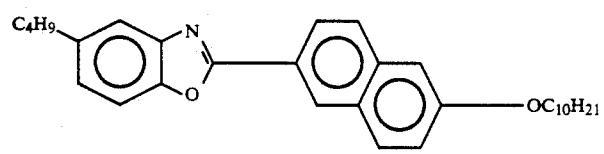 (1-190)
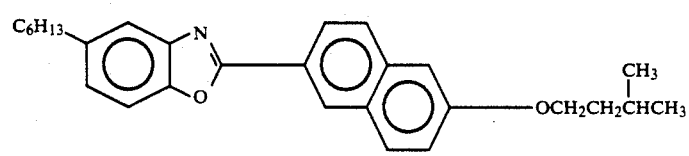 (1-191)
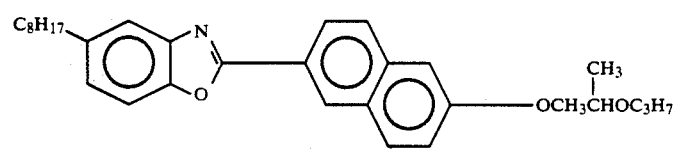 (1-192)
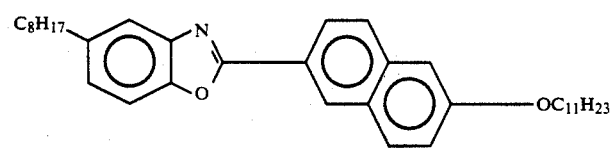 (1-193)
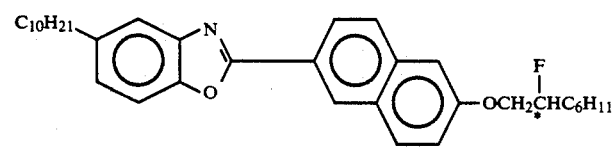 (1-194)
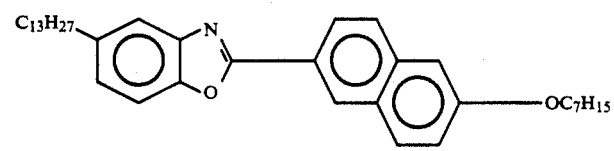 (1-195)
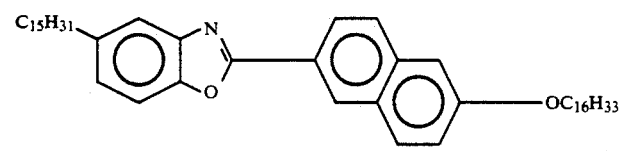 (1-196)

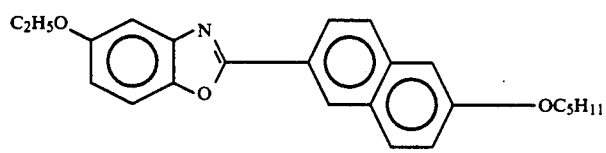 (1-197)
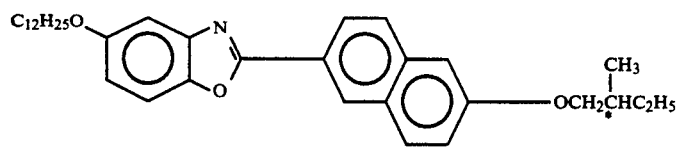 (1-198)
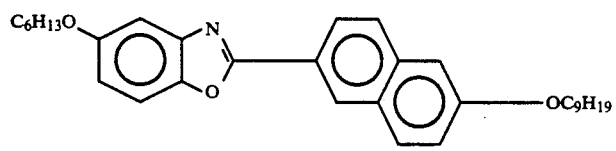 (1-199)
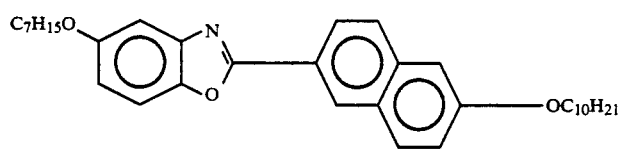 (1-200)
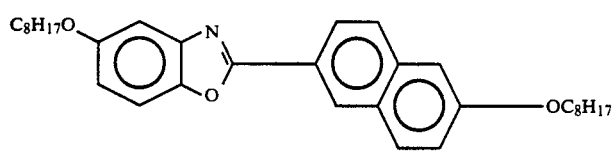 (1-201)
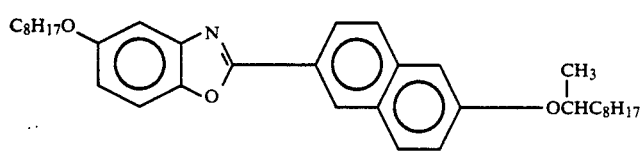 (1-202)
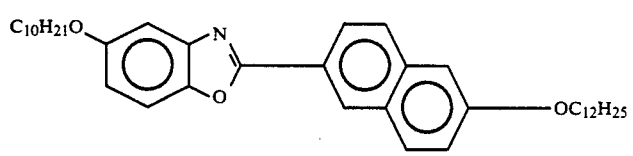 (1-203)
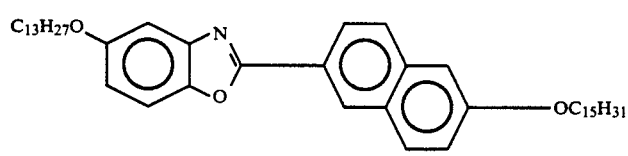 (1-204)
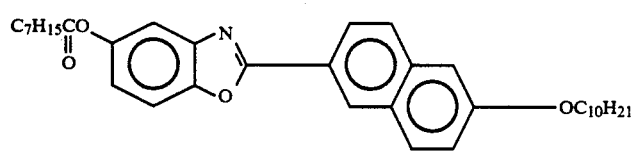 (1-205)
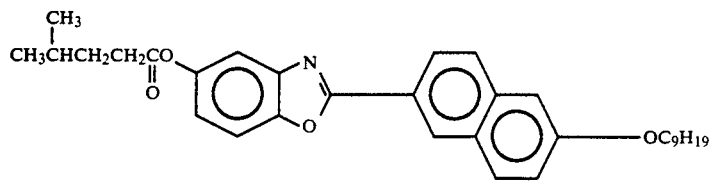 (1-206)

-continued
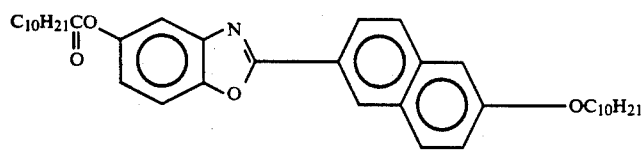 (1-207)
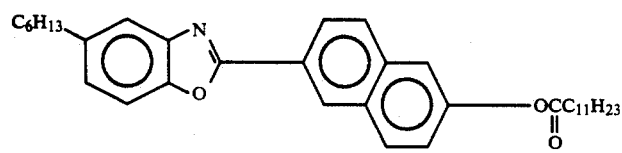 (1-208)
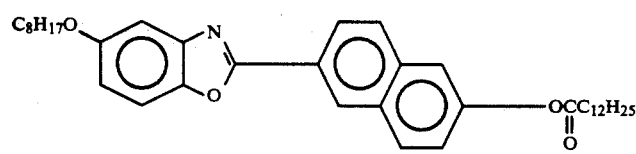 (1-209)
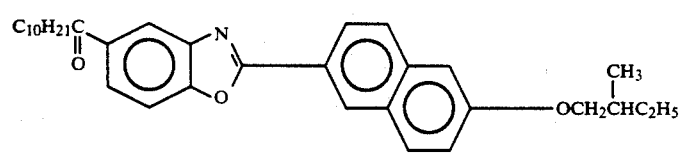 (1-210)
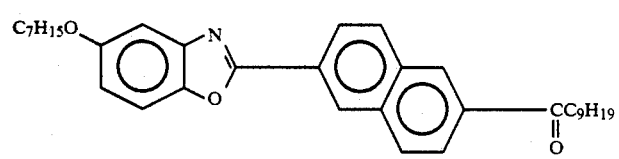 (1-211)
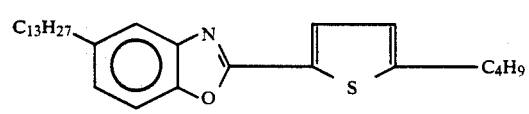 (1-212)
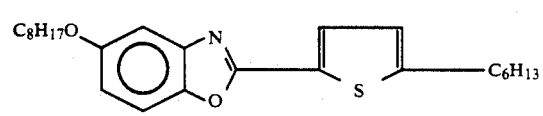 (1-213)
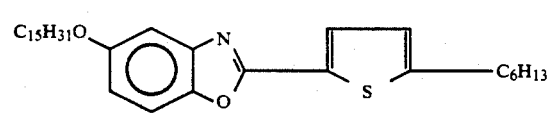 (1-214)
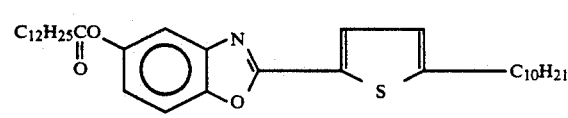 (1-215)
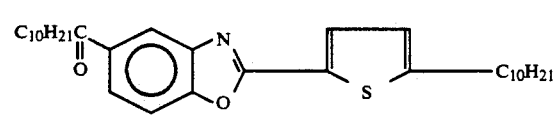 (1-216)
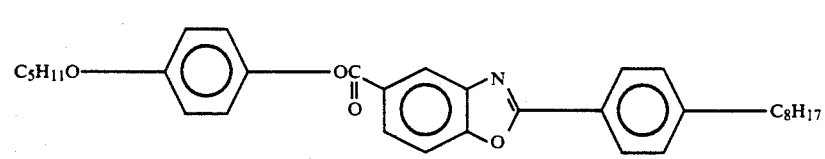 (1-217)

-continued
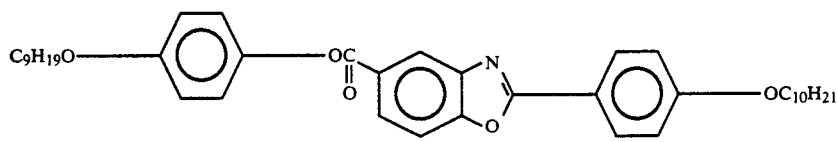 (1-218)
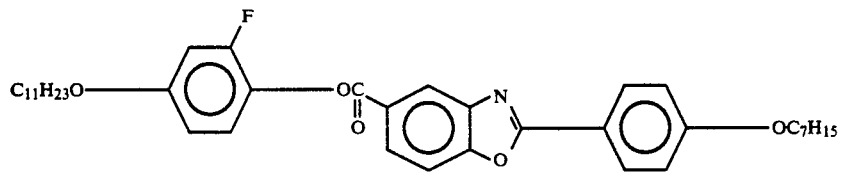 (1-219)
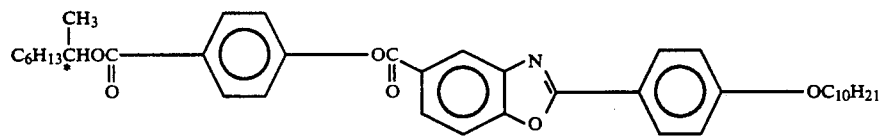 (1-220)
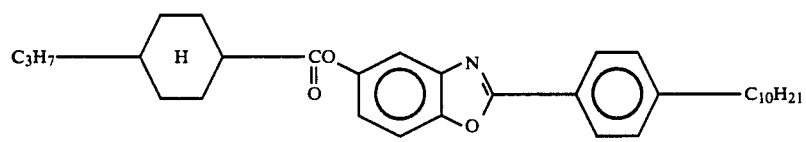 (1-221)
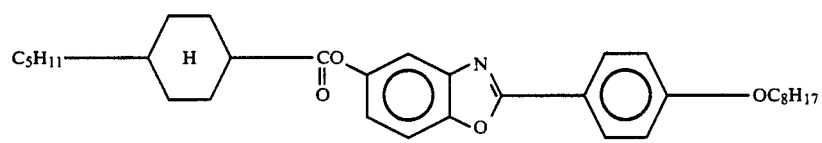 (1-222)
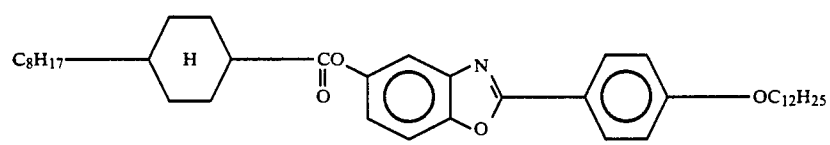 (1-223)
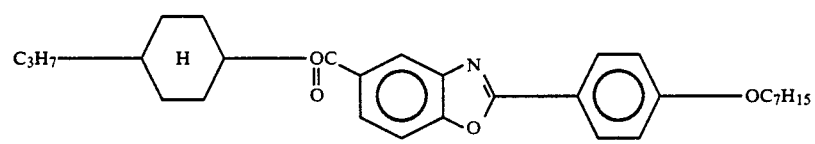 (1-224)
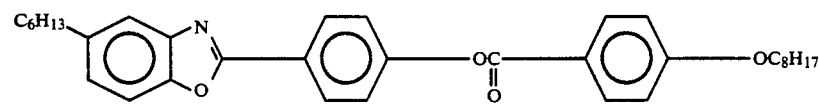 (1-225)
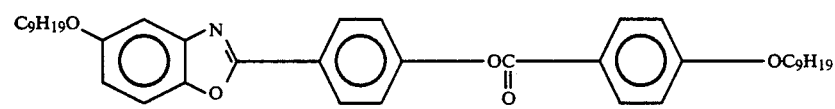 (1-226)
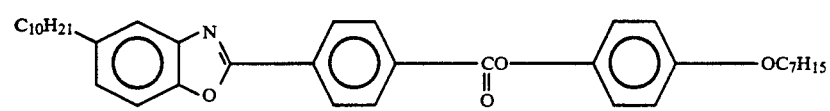 (1-227)
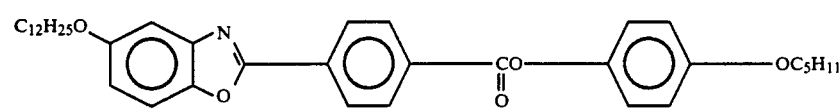 (1-228)

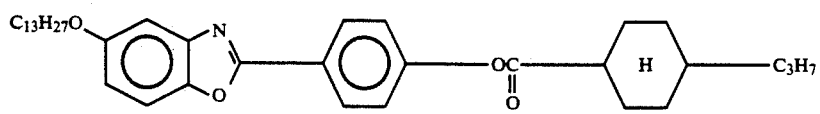 (1-229)
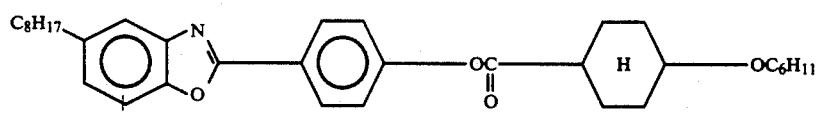 (1-230)
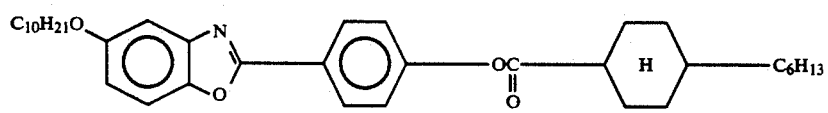 (1-231)
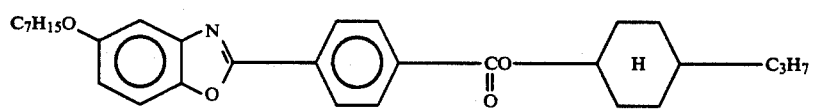 (1-232)
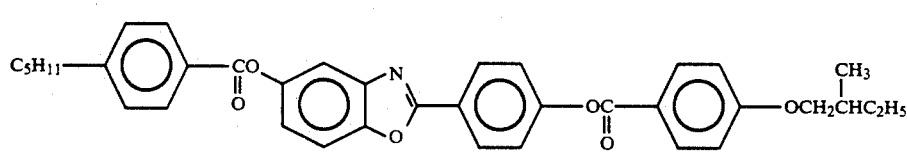 (1-233)
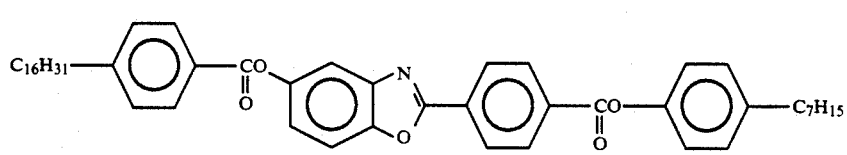 (1-234)
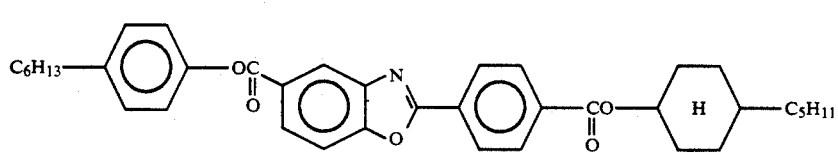 (1-235)
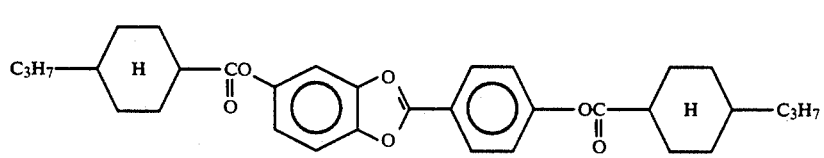 (1-236)
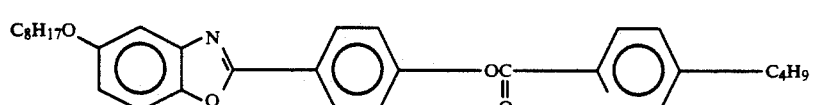 (1-237)
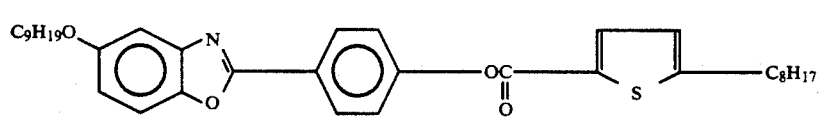 (1-238)
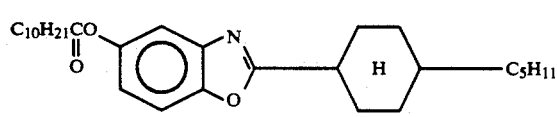 (1-239)
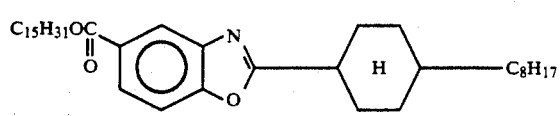 (1-240)

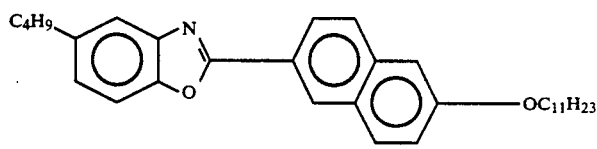 (1-241)
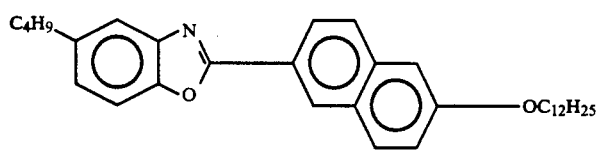 (1-242)
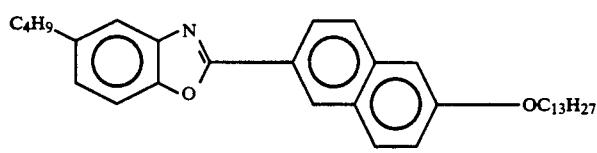 (1-243)
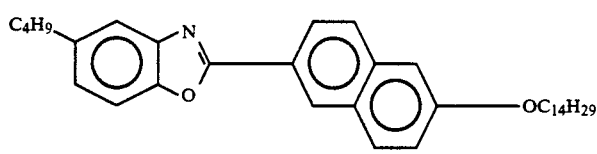 (1-244)
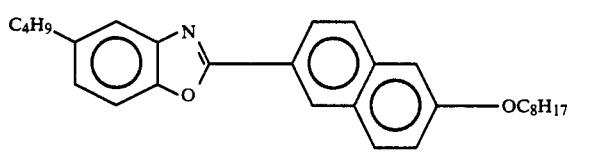 (1-245)
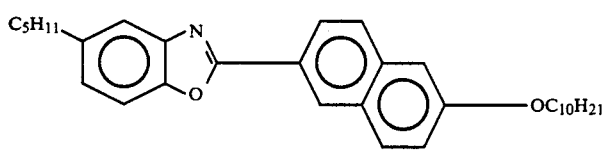 (1-246)
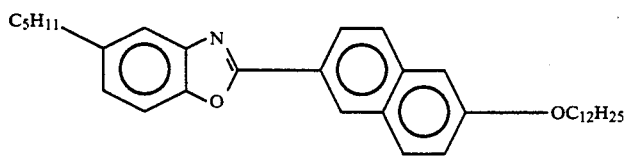 (1-247)
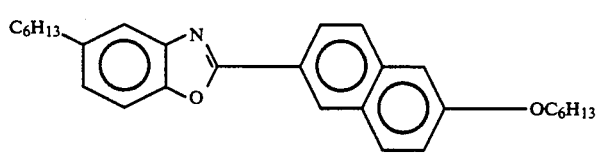 (1-248)
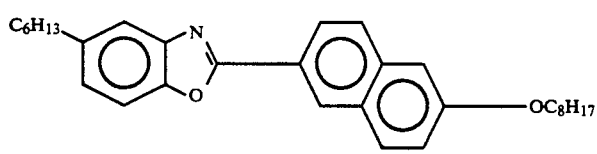 (1-249)
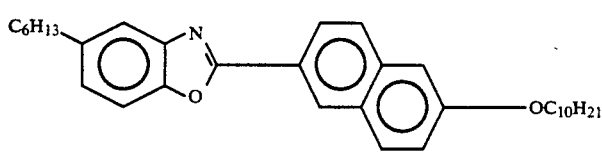 (1-250)

-continued
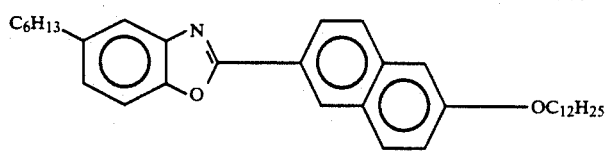  (1-251)
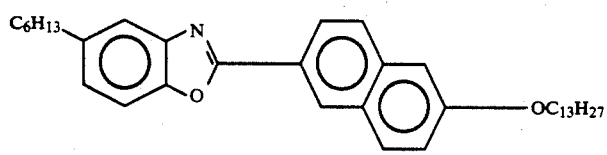  (1-252)
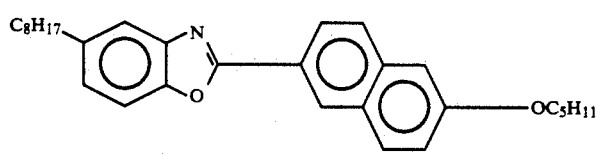  (1-253)
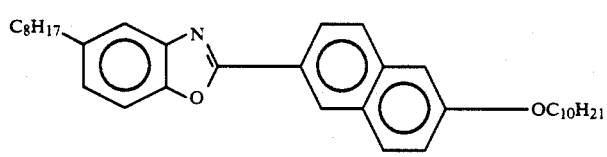  (1-254)
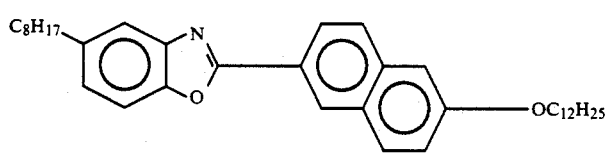  (1-255)
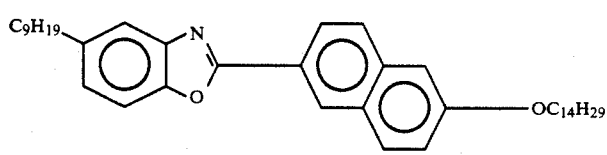  (1-256)
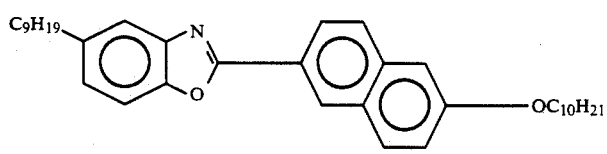  (1-257)
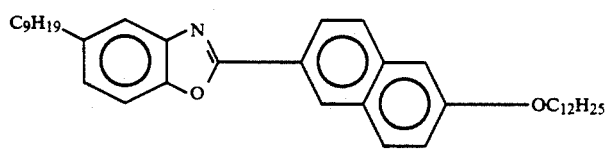  (1-258)
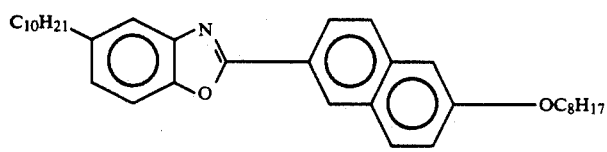  (1-259)
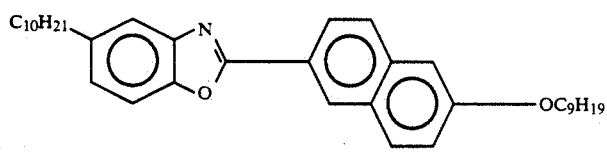  (1-260)

-continued
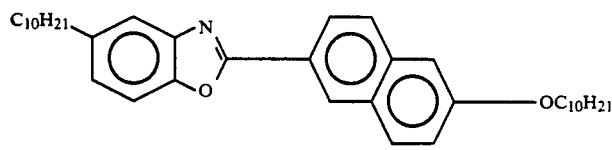 (1-261)
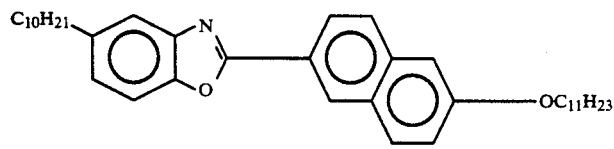 (1-262)
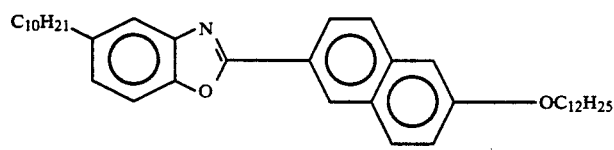 (1-263)
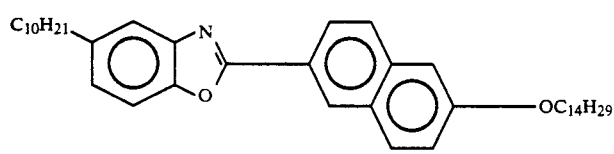 (1-264)
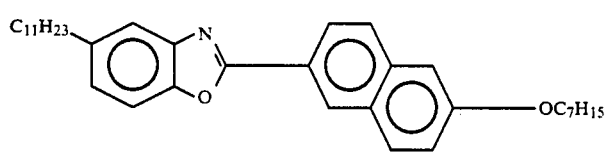 (1-265)
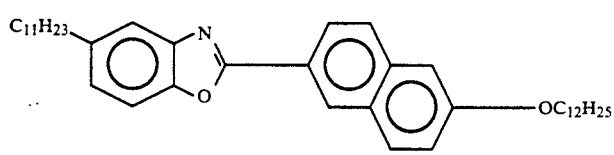 (1-266)
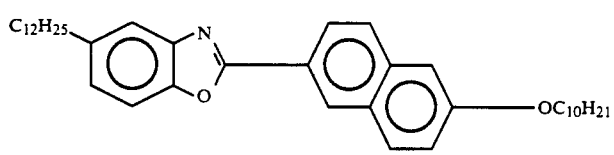 (1-267)
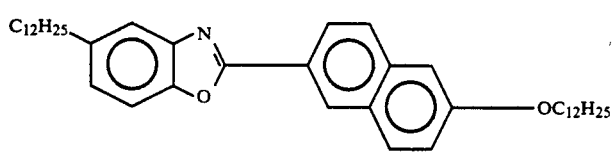 (1-268)
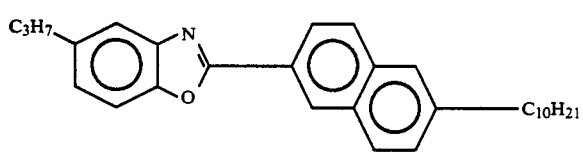 (1-269)
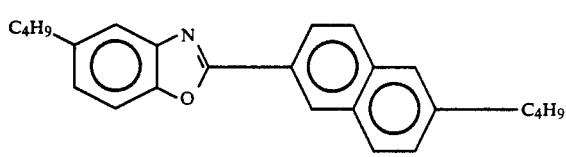 (1-270)

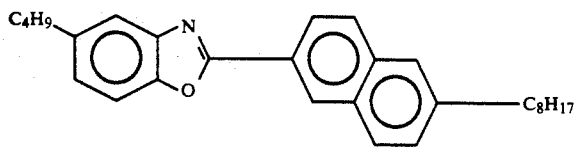 (1-271)
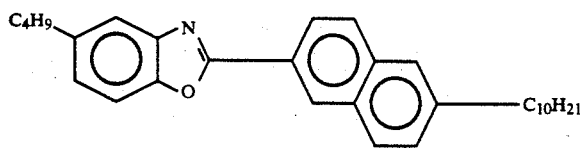 (1-272)
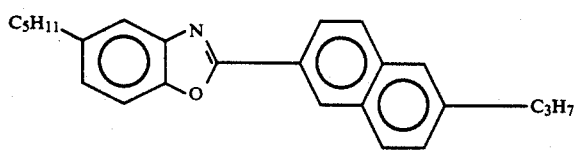 (1-272-1)
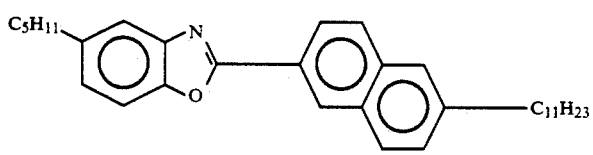 (1-273)
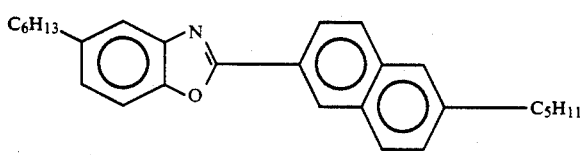 (1-274)
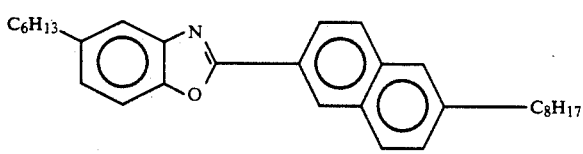 (1-275)
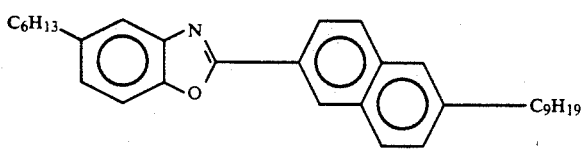 (1-276)
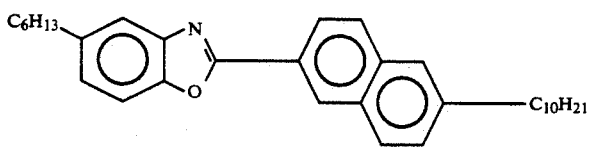 (1-277)
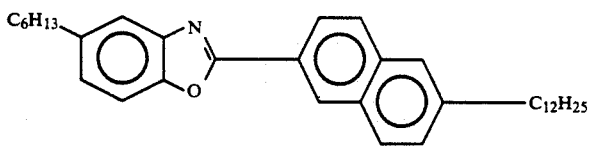 (1-278)
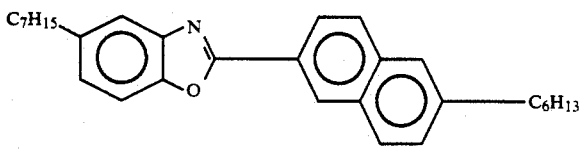 (1-279)

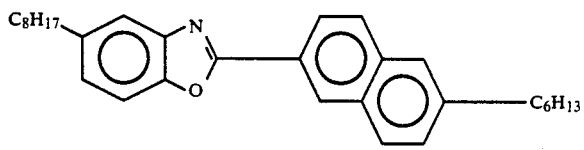 (1-280)
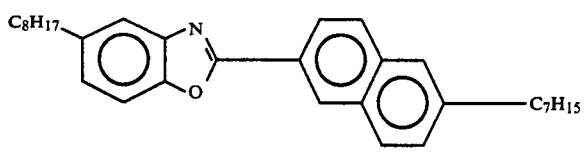 (1-281)
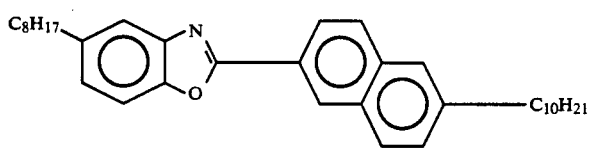 (1-282)
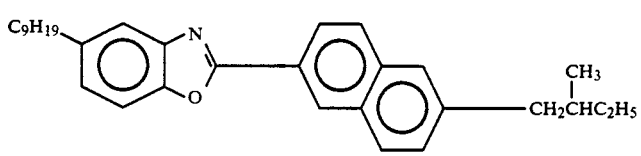 (1-283)
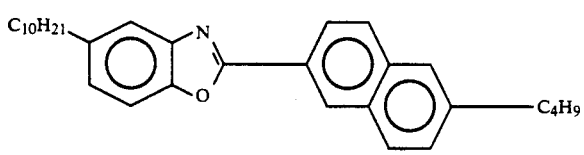 (1-284)
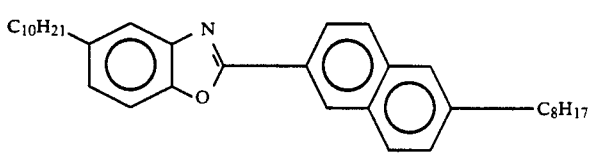 (1-285)
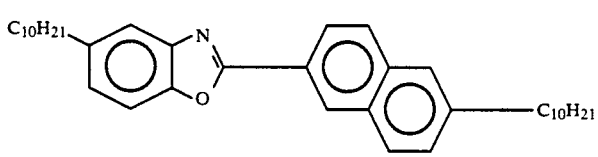 (1-286)
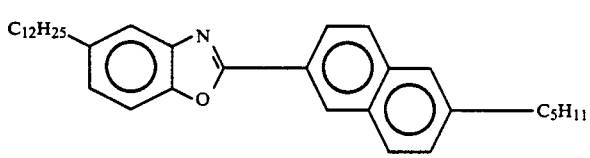 (1-287)
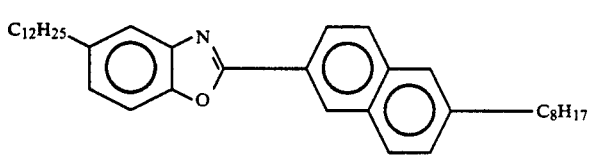 (1-288)
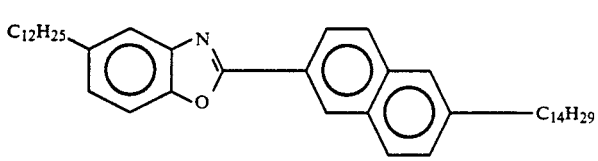 (1-289)

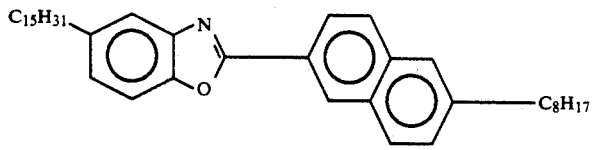
(1-290)

The liquid crystal composition of the present invention comprises at least one species of the mesomorphic compound represented by Formula [I] and a second mesomorphic compound. The liquid crystal composition according to the present invention may preferably be formulated as a liquid crystal composition showing a chiral smectic phase.

Specific examples of the second mesomorphic compound as described above may include those denoted by the following Formulae (II) to (X).

In Formula (II), preferred compounds thereof include those represented by the following Formulae (IIa) to (IId):

(IIa)

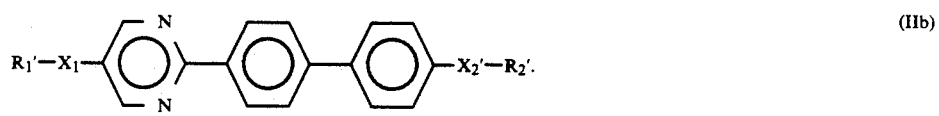
(IIb)

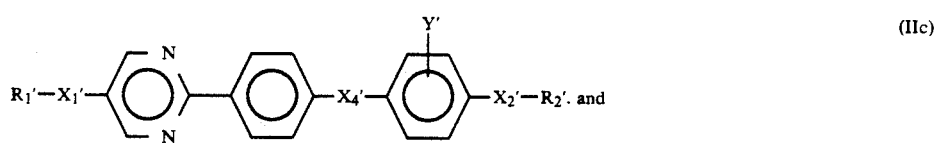
(IIc)

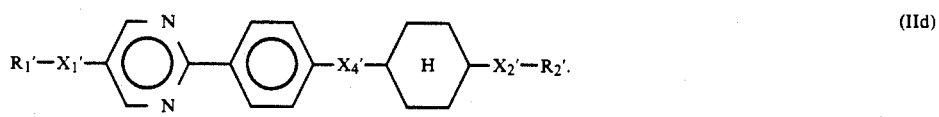
(IId)

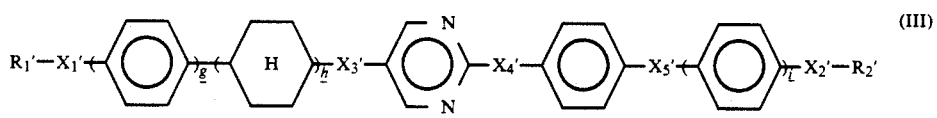
(III)

wherein g and h denote 0 or 1 with the proviso that g+h=1; i denotes 0 or 1; $X_1'$ and $X_2'$ denote a single bond,

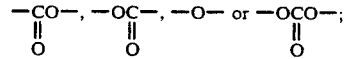

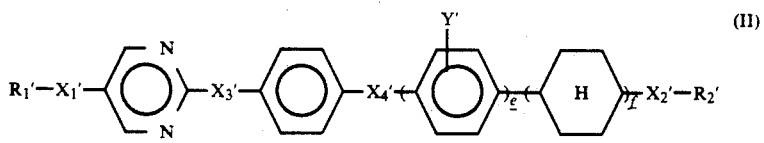
(II)

wherein e denotes 0 or 1 and f denotes 0 or 1 with proviso that 3+f=0 or 1; Y' denotes H, halogen, CH$_3$ or CF$_3$; $X_1'$ and $X_2'$ respectively denote a single bond,

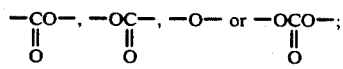

and $X_3'$ and $X_4'$ respectively denote a single bond,

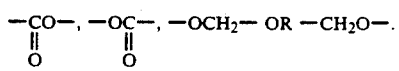

and $X_3'$, $X_4'$ and $X_5'$ denote a single bond,

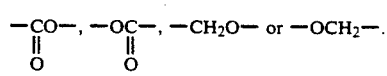

In the formula (III), preferred compounds thereof include those represented by the following Formulae (IIIa) to (IIIc):

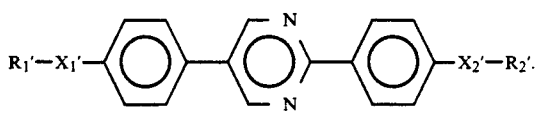
(IIIa)

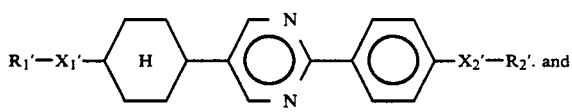
(IIIb)

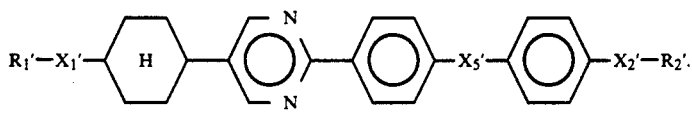
(IIIc)

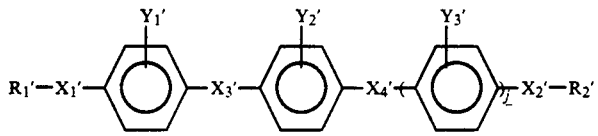
(IV)

wherein j denotes 0 or 1; $Y_1'$, $Y_2'$ and $Y_3'$ denote H, halogen, $CH_3$ or $CF_3$; $X_1'$ and $X_2'$ denote a single bond,

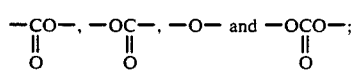

and $X_3'$ and $X_4'$ denote a single bond,

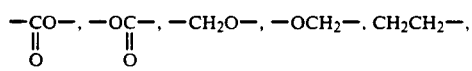

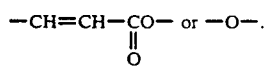

In formula (IV), preferred compounds thereof may include those represented by the following Formulae (IVa) and (IVb):

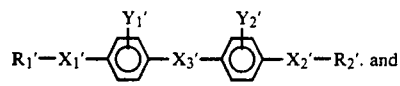
(IVa)

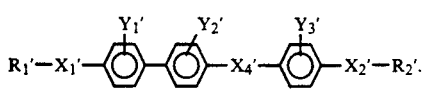
(IVb)

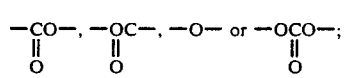
(V)

wherein k, l and m denote 0 or 1 with the proviso that k+l+m=0, 1 or 2; $X_1'$ and $X_2'$ denote a single bond,

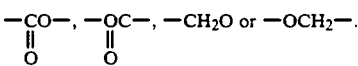

and $X_3'$ and $X_4'$ denote a single bond,

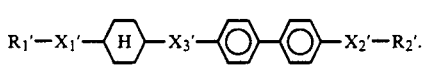

In Formula (V), preferred compounds thereof may include those represented by the following Formulae (Va) to (Vf);

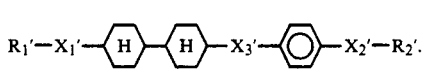
(Va)

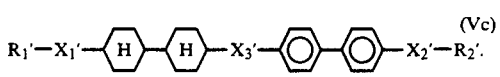
(Vb)

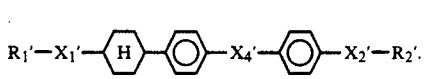
(Vc)

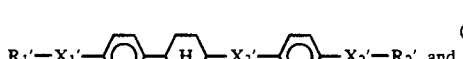
(Vd)

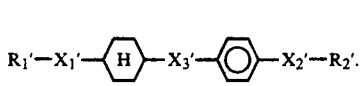
(Ve)

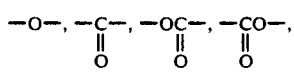
(Vf)

Herein, $R_1'$ and $R_2'$ denote a linear or branched alkyl group having 1-18 carbon atoms capable of including one or two or more non-neighboring methylene groups which can be replaced with —CHX— (wherein x is halogen) and capable of further including one or two or more non-neighboring methylene groups other than those directly connected to $X_1'$ or $X_2'$ which can be replaced with at least one species of

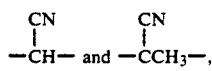

with proviso that $R_1'$ and $R_2'$ do not connect to a ring structure when $R_1'$ and $R_2'$ denote a halogenated alkyl group containing one methylene group replaced with —CHX— (wherein X is halogen).

Preferred examples of $R_1'$ and $R_2'$ include those represented by the following groups (i) or (vii):

i) a linear alkyl group having 1-15 carbon atoms;

ii) 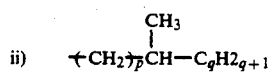

(optically active or inactive) wherein p denotes an integer of 0-5 and g denotes an integer of 1-11;

iii) 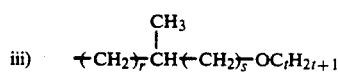

(optically active or inactive) wherein r denotes an integer of 0-6, s denotes 0 to 1, and t denotes an integer of 1-14;

iv) 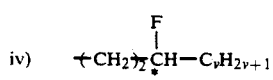

wherein u denotes 0 or 1 and v denotes an integer of 1-16;

v) 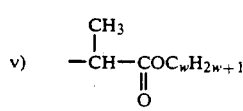

(optically active or inactive) wherein w denotes an integer of 1-15;

vi) 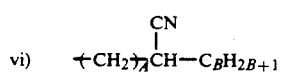

(optically active or inactive) wherein A denotes an integer of 0-2 and B denotes an integer of 1-15;

vii) 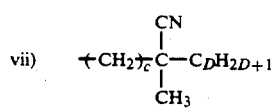

(optically active or inactive) wherein C denotes an integer of 0-2 and D denotes an integer of 1-15.

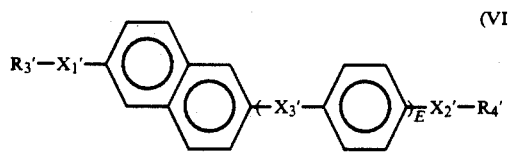
(VI)

wherein E denotes 0 or 1; $X_1'$ and $X_2'$ denote a single bond,

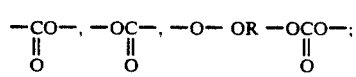

$X_3'$ denotes a single bond, —CO—, —OC—, —CH$_2$O— or —OCH$_2$—.

In the above Formula (VI), preferred compounds thereof include those represented by the following Formulae (VIa) and (VIb):

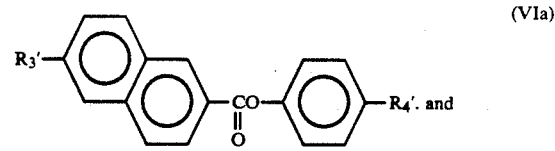
(VIa)

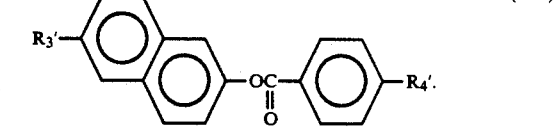
(VIb)

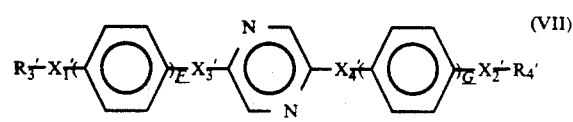
(VII)

wherein F and G denote 0 or 1; $X_1'$ and $X_2'$ respectively denote a single bond,

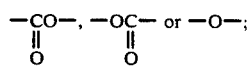

and $X_3'$ and $X_4'$ denote a single bond,

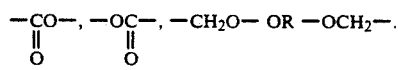

In the above Formula (VII), preferred compounds thereof include those represented by the following Formulae (VIIa) and (VIIb).

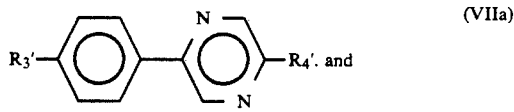
(VIIa)

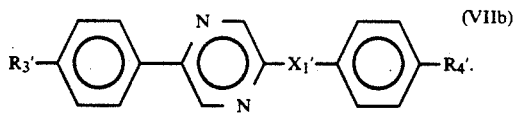
(VIIb)

Herein, $R_3'$ and $R_4'$ respectively denote a linear or branched alkyl group having 1-18 carbon atoms capable of including one or two more non-neighboring methylene groups which can be replaced with —CHX— (wherein X is halogen) and capable of further including one or two or more non-neighboring methylene groups other than those directly connected to $X_1'$ or $X_2'$ which can be replaced with at least one species of

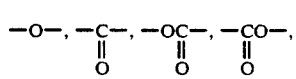

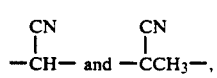

with proviso that $R_3'$ and $R_4'$ do not connect to a ring structure when $R_3'$ and $R_4'$ denote a halogenated alkyl group containing one methylene group replaced with —CHX— (wherein X is halogen).

Further, preferred examples of $R_3'$ and $R_4'$ include those represented by the following groups (i) to (vii):

i) a linear alkyl group having 1-15 carbon atoms;

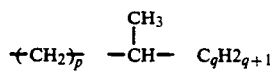   ii)

(optically active or inactive) wherein p denotes an integer of 0-5 and g denotes an integer of 1-11;

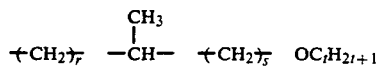   iii)

(optically active or inactive) wherein r denotes an integer of 0-6; s denotes 1 to 1, and t denotes an integer of 1-14;

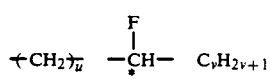   iv)

wherein u denotes an integer of 0-5 and v denotes an integer of 1-16;

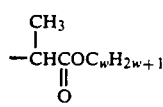   v)

(optically active or inactive) wherein 2 denotes an integer of 1-15;

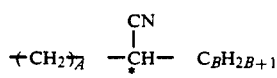   vi)

(optically active or inactive) wherein A denotes an integer of 0-2 and B denotes an integer of 1-15; and

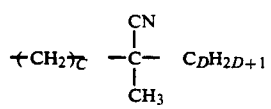   vii)

(optically active or inactive) wherein C denotes an integer of -2 and D denotes an integer of 1-15.

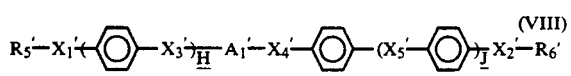   (VIII)

wherein H and J denote 0 to 1 with proviso that $H+J=0$ or 1; $X_1'$— and $X_2'$ respectively denote a single bond,

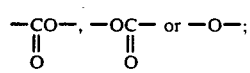

$A_1'$ denotes

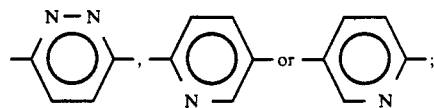

and $X_3'$ and $X_4'$ denote a single bond,

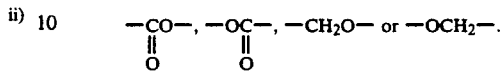

In the above Formula (VIII), preferred compounds thereof include those represented by the following Formulae (VIIIa) and (VIIIc):

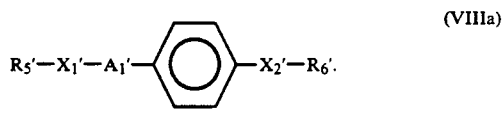   (VIIIa)

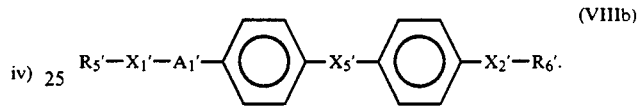   (VIIIb)

and

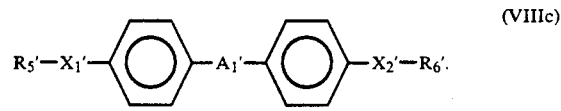   (VIIIc)

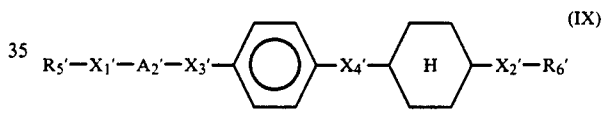   (IX)

wherein $X_1'$ and $X_2'$ denote a single bond,

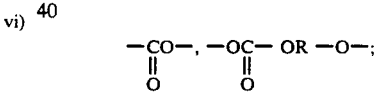

$A_2'$, denotes

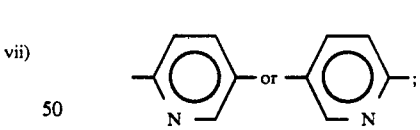

and $X_3'$ and $X_4'$ denote a single bond,

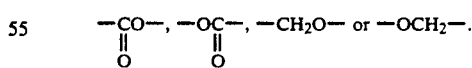

In the above Formula (IX), preferred compounds thereof include those represented by the following Formulae (IXa) and (IXb):

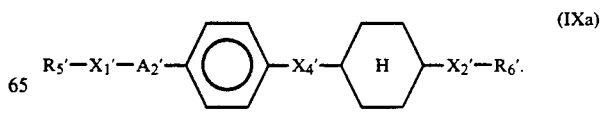   (IXa)

and

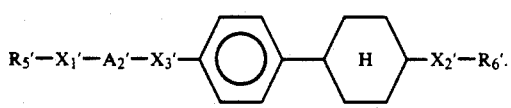 (IXb)

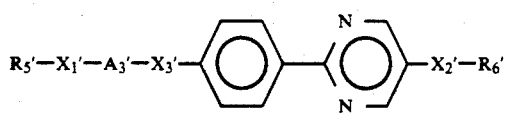 (X)

wherein $X_1'$ and $X_2'$ denote a single bond,

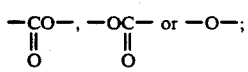

$A_3'$ denotes

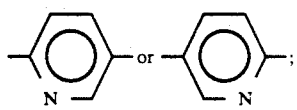

and $X_3'$ denotes a single bond,

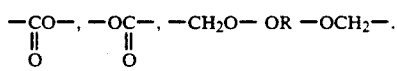

In the above Formula (X), preferred compounds thereof include those represented by the following Formulae (Xa) to (Xg):

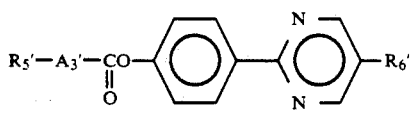 (Xa)

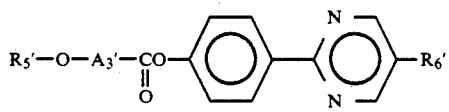 (Xb)

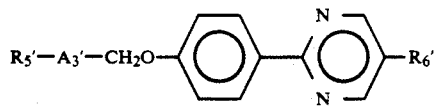 (Xc)

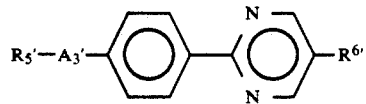 (Xd)

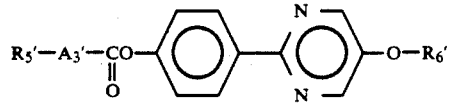 (Xe)

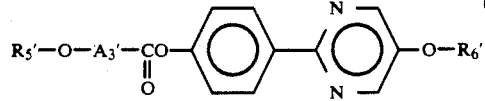 (Xf)

and

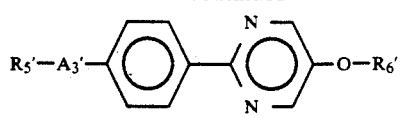 (Xg)

Herein, $R_5'$ and $R_6'$ denote a linear or branched alkyl group having 1-18 carbon atoms capable of including one or two or more non-neighboring methylene groups other than those directly connected to $X_1'$ or $X_2'$ which can be replaced with at least one species of

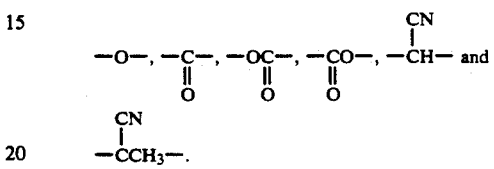

Further, preferred examples of $R_5'$ and $R_6'$ include those represented by the following groups (i) to (vi):

i) a linear alkyl group having 1-15 carbon atoms;

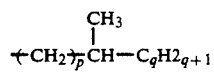 ii)

(optically active or inactive) wherein p denotes an integer of 0-5 and g denotes an integer of 1-11;

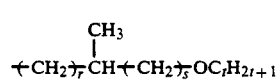 iii)

(optically active or inactive) wherein r denotes an integer of 0-6, s denotes 0 to 1, and t denotes an integer of 1-14;

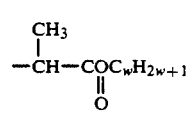 iv)

(optically active or inactive) wherein w denotes an integer of 1-15;

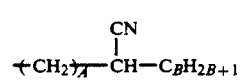 v)

(optically active or inactive) wherein A denotes an integer of 0-2 and B denotes an integer of 1-15; and

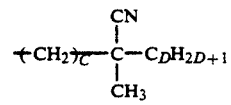 vi)

(optically active or inactive) wherein C denotes an integer of 0-2 and D denotes an integer of 1-15.

In the above-mentioned Formulae (IIa) to (IId), more preferred compounds thereof include those represented by the Formulae (IIaa) to (IIdc):

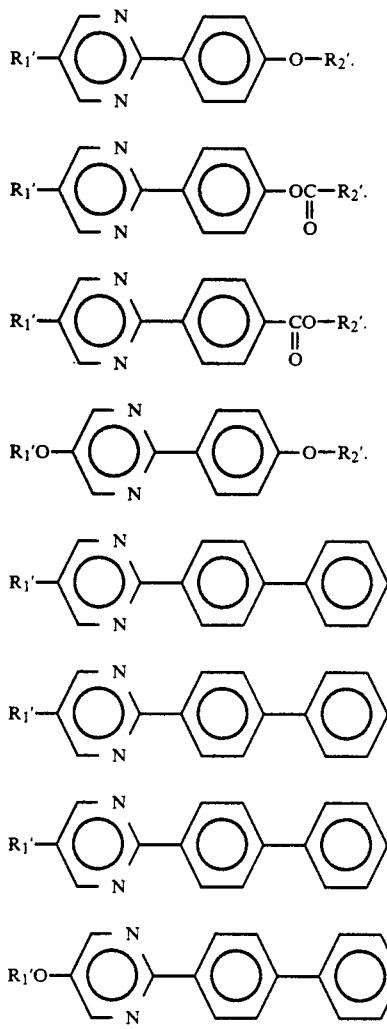
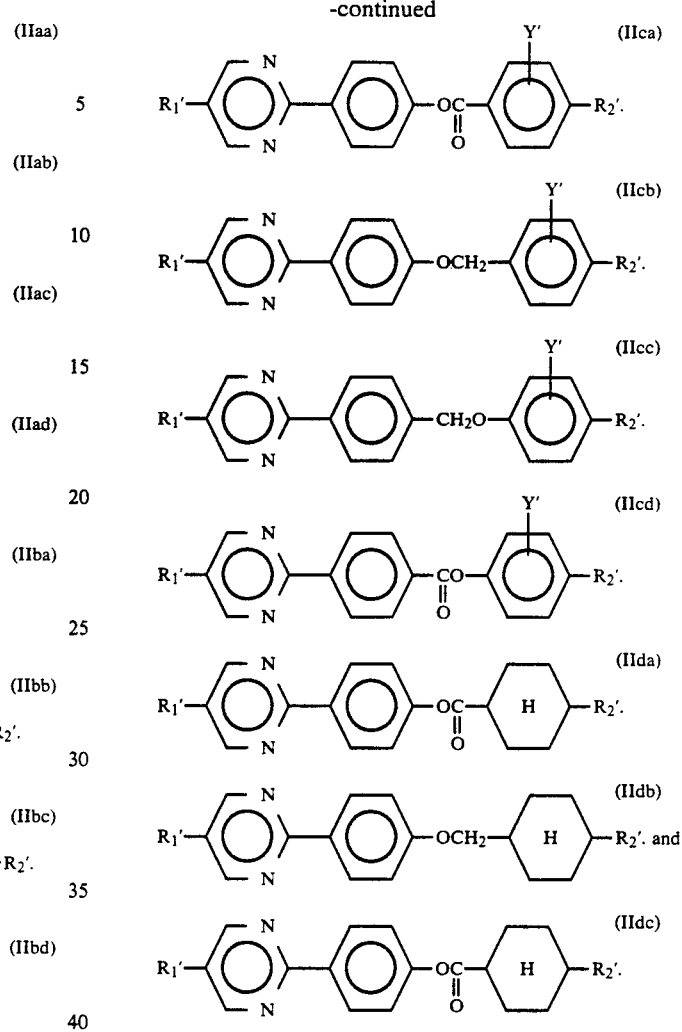
In the above-mentioned Formulae (IIIa) to (IIIc), more preferred compounds thereof include those represented by the Formulae (IIIaa) to (IIIIcd);
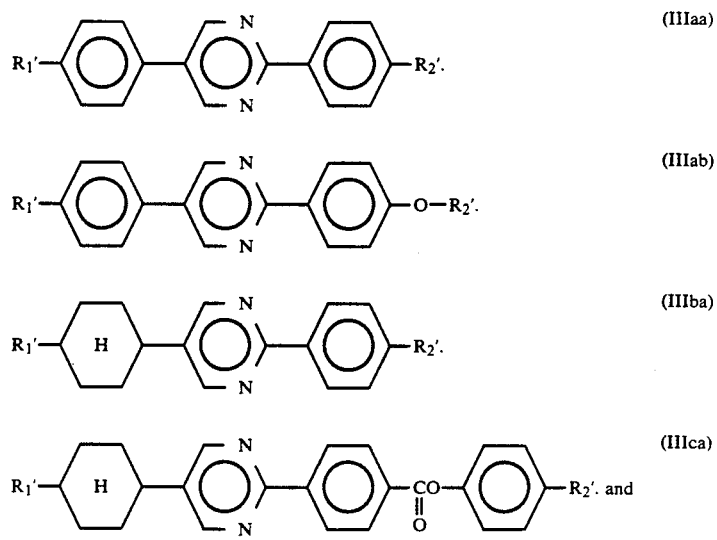

-continued

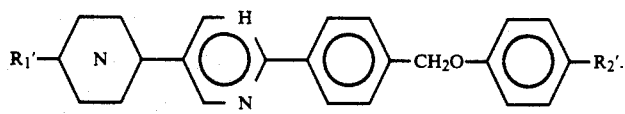 (IIIcb)

In the above-mentioned Formulae (IVa) to (IVb), more preferred compounds thereof include those represented by the Formulae (IVaa) to (IVbf):

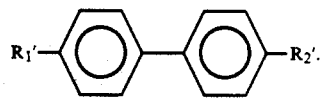 (IVaa)

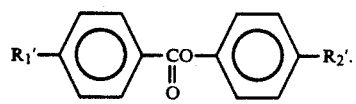 (IVab)

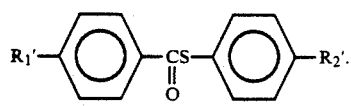 (IVac)

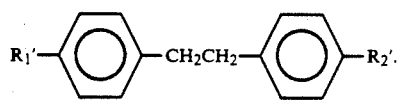 (IVad)

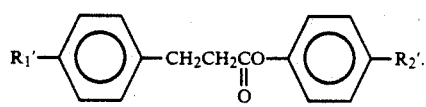 (IVae)

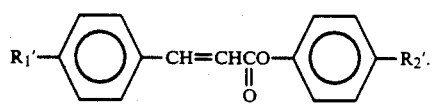 (IVaf)

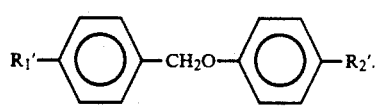 (IVag)

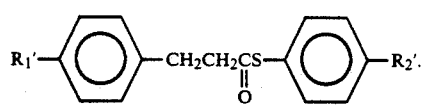 (IVah)

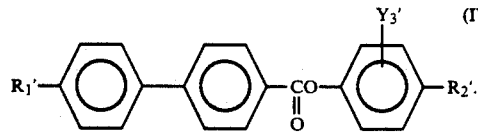 (IVba)

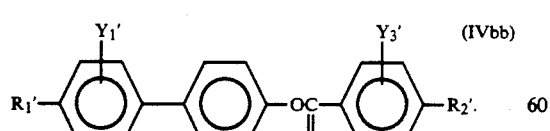 (IVbb)

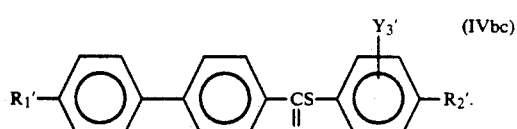 (IVbc)

-continued

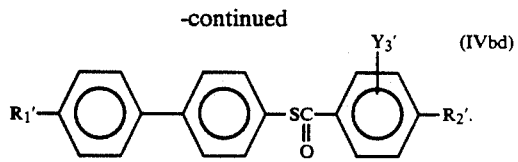 (IVbd)

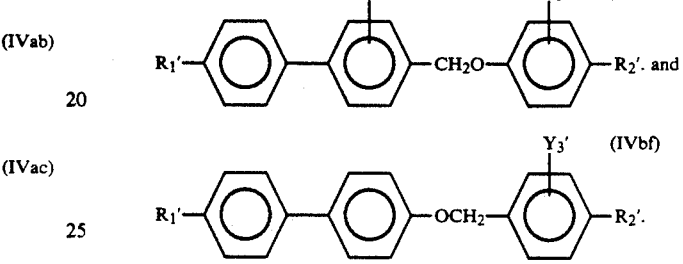

(VIbe)

(IVbf)

In the above-mentioned Formulae (Va) to (Vf), more preferred compounds thereof include those represented by the Formulae (Vaa) to (Vfa):

(Vaa)

(Vab)

(Vba)

(Vbb)

(Vda)

(Vea)

(Vfa)

More preferred compounds of Formula (VIIa) to (VIIb) may include those represented by the Formulae (VIIaa) to (VIIbb):

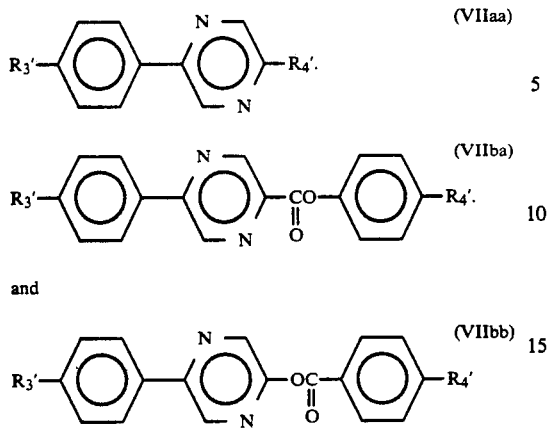

(VIIaa)

(VIIba)

and (VIIbb)

In the above-mentioned Formula (VIIIa) to (VIIIc), more preferred compounds thereof include those represented by the Formulas (VIIIaa) to (VIIIcc):

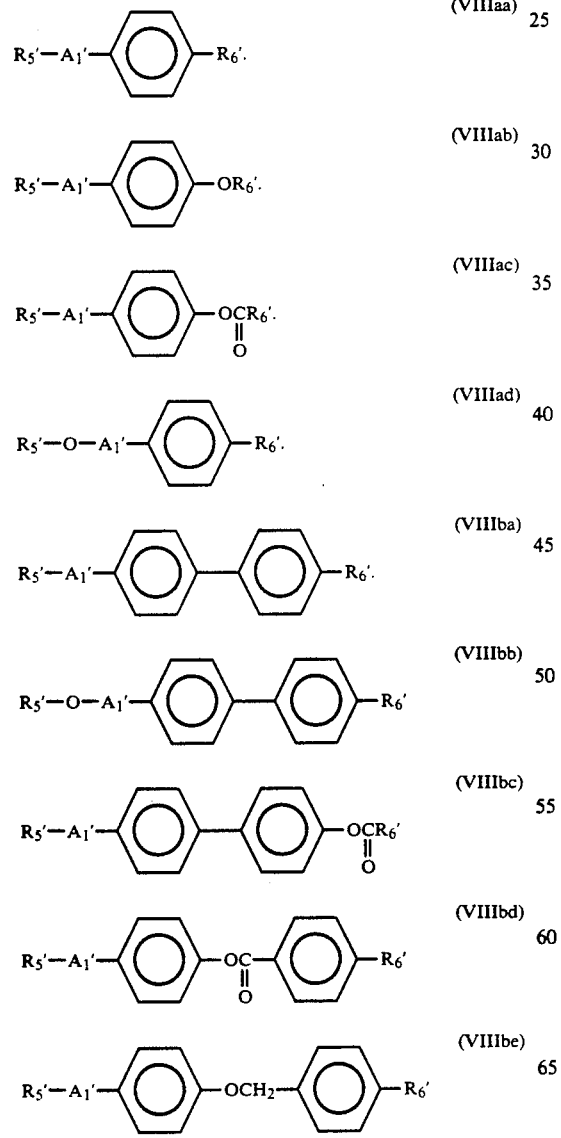

(VIIIaa)

(VIIIab)

(VIIIac)

(VIIIad)

(VIIIba)

(VIIIbb)

(VIIIbc)

(VIIIbd)

(VIIIbe)

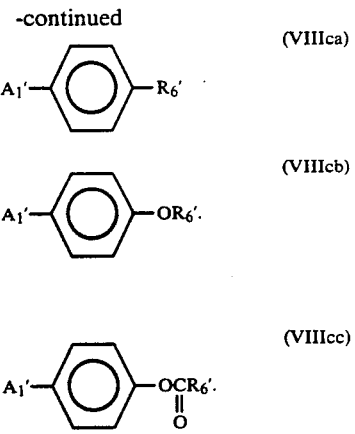

(VIIIca)

(VIIIcb)

and (VIIIcc)

In the above-mentioned Formula (IXa) to (IXb), more preferred compounds thereof include those represented by the Formulae (IXaa) to (IXbb):

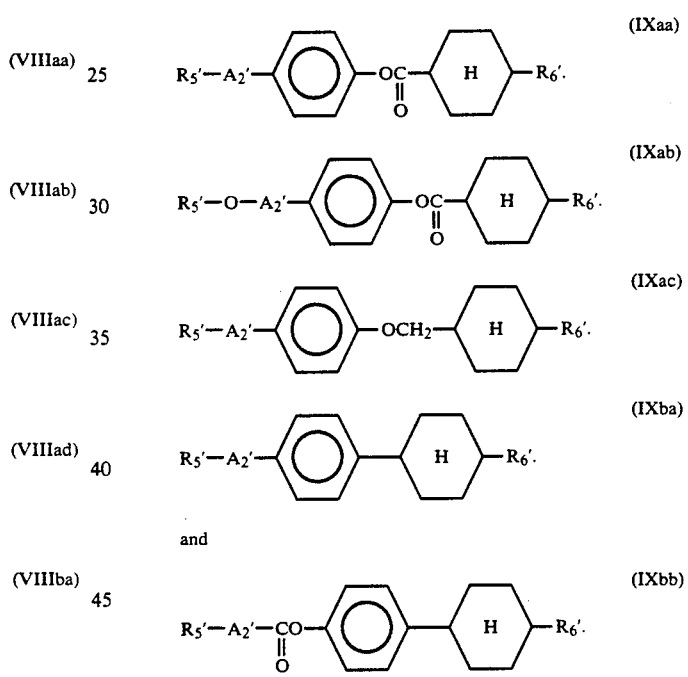

(IXaa)

(IXab)

(IXac)

(IXba)

and (IXbb)

In formulation the liquid crystal composition according to the present invention, the liquid crystal composition may desirably contain 1–80 wt. %, preferably 1–60 wt. %, more preferably 1–40 wt. % of a mesomorphic compound represented by the Formula (I) together with another mesomorphic compound.

Further, when two or more species of the compounds represented by the Formula (I) are used, the liquid crystal composition may desirably contain 1–80 wt. %, preferably 1–60 wt. %, more preferably 1–40 wt. %, of the two or more species of the compounds represented by the Formula (I).

The liquid crystal device according to the present invention may preferably be prepared under vacuum by heating the liquid crystal composition into an isotropic state, filling a blank cell comprising a pair of oppositely spaced electrodes with the composition, gradually cooling the cell to form a liquid crystal layer and restoring the normal pressure. FIG. 1 is a partial sectional view of an embodiment of the ferroelectric liquid crystal device prepared as described above.

Referring to FIG. 1, the liquid crystal device includes a liquid crystal layer 1 assuming a chiral smectic phase disposed between a pair of glass substrates 2 each having thereon a plurality of transparent stripe electrodes 3 and an insulating alignment control layer 4. Lead wires 6 are connected to the electrodes so as to apply a driving voltage to the liquid crystal layer 1 from a power supply 7. Outside the substrates 2, a pair of polarizers 8 and disposed so as to modulate incident light $I_0$ from a light source 9 in cooperation with the liquid crystal 1 to provide modulated light I.

Each of two glass substrates 2 is coated with a transparent electrodes 3 comprising stripes of $In_2O_3$, $SnO_2$ or ITO (indium-tin-oxide) to form stripe electrodes. Further thereon, an insulating alignment control layer 4 is formed by rubbing a film of a polymer such as polyimide with gauze or acetate fiber-woven cloth so as to align the liquid crystal molecules in the rubbing direction. Further, it is possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin.

Alternatively, it is also possible to use a single layer of inorganic or organic insulating alignment control layer. A suitable inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating, etc.). The insulating alignment control layer may have a thickness of ordinarily 30 Å–1 micron, preferably 30–3000 Å, more preferably 50–1000 Å. The two glass substrates 2 with transparent stripe electrodes 3 and insulating alignment control layers 4 are held to a prescribed (but arbitrary) gap with a spacer 5. For example, such a cell structure with a prescribed gap may be formed by sandwiching spacers of silica or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed so as to provide a liquid crystal layer 1 in a thickness of generally 0.5 to 20 microns, preferably 1 to 5 microns.

The liquid crystal provided by the composition of the present invention may desirably assume a SmC* phase (chiral smectic C phase) in a wide temperature range including room temperature (particularly, broad in a lower temperature side) and also shows wide margins of drive voltage and drive temperature when contained in a device.

Particularly, in order to show a good alignment characteristic and form a uniform monodomain, the liquid crystal may show a phase transition series comprising isotropic phase—Ch phase (cholesteric phase)—SmA (smectic A phase)—SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
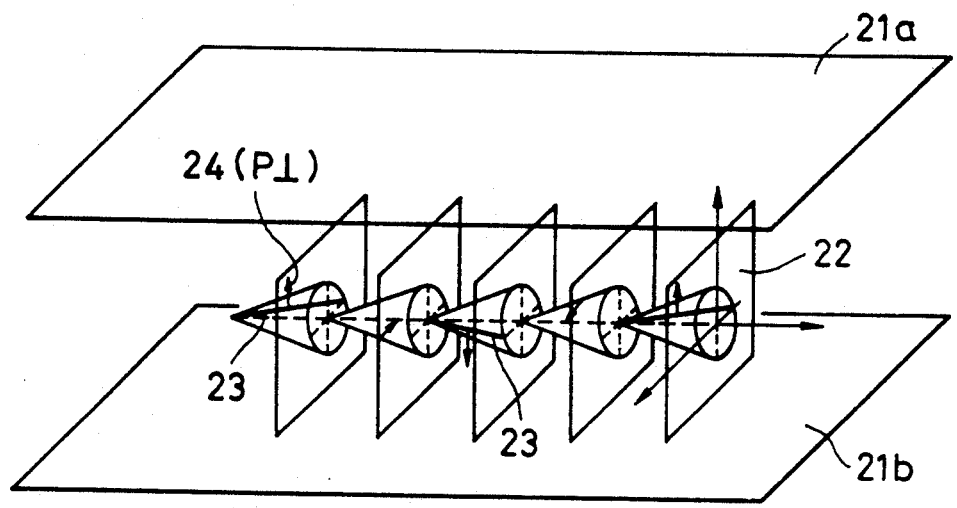
FIGS. 2 and 3 illustrate the orientation of the liquid crystal material in the liquid crystal cell of FIG. 1.

FIG. 2 explains the operation of a ferroelectric liquid crystal cell (device). Reference numerals 21a and 21b denote substrates (glass plates) on which a transparent electrodes of, e.g., $In_2O_3$, $SnO_2$, ITO (indium-tin-oxide), etc., are disposed. A liquid crystal of an SmC*-phase (chiral smectic C phase) or SmH*-phase (chiral smectic H phase) in which liquid crystal molecular layers 22 are aligned perpendicular to surfaces of the glass plates is hermetically sealed therebetween. Full lines 23 show liquid crystal molecules wherein each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are directed in the direction of the electric field. The liquid crystal molecules 23 have an elongated shape and show refractive anisotropy between their long and short axes. Accordingly, it is easily understood that when, for instance, polarizers arranged in a cross nicol relationship (i.e., with their polarizing directions crossing each other) are disposed on the upper and the lower surfaces of the glass plates, the liquid crystal cell functions as a liquid crystal optical modulation device (i.e., an optical shutter) having optical characteristics which vary depending upon the polarity of an applied voltage.

Figure 3:
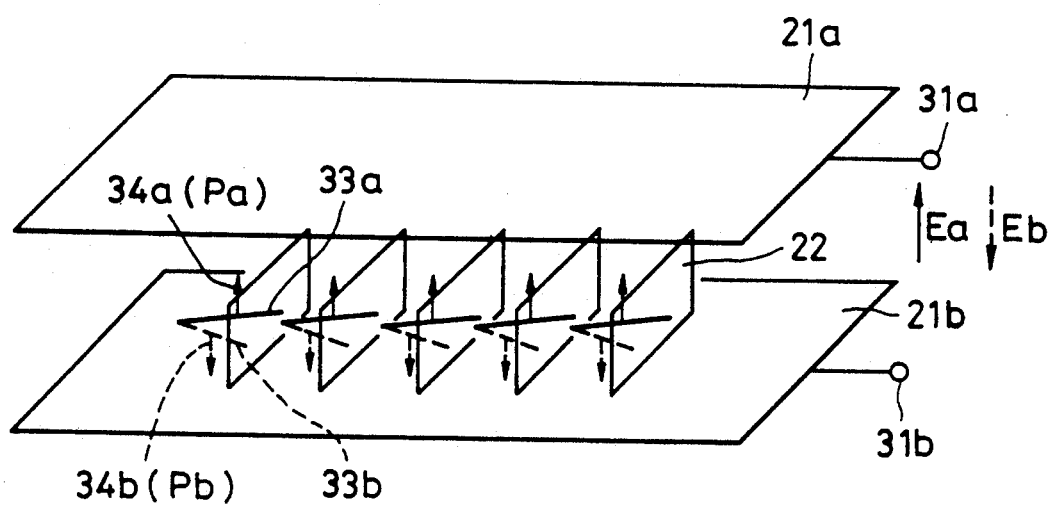

Further, when the liquid crystal cell is made sufficiently thin (e.g., on the order of less than about 10 microns), the helical structure of the liquid crystal molecules is unwound to provide a non-helical structure even in the absence of an electric field, whereby the dipole element assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage applications means 31a and 31b, the dipole moment is directed either in the upper direction 34a or in the lower direction Eb. In correspondence with this, the liquid crystal molecules are thus oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are change. This state is also stably retained even if the electric field is removed. Further, as long as the magnitude of the electric field Ea or Eb being applied is not above a certain threshold value, the liquid crystal molecules remain in their respective orientation states.

Figure 4:
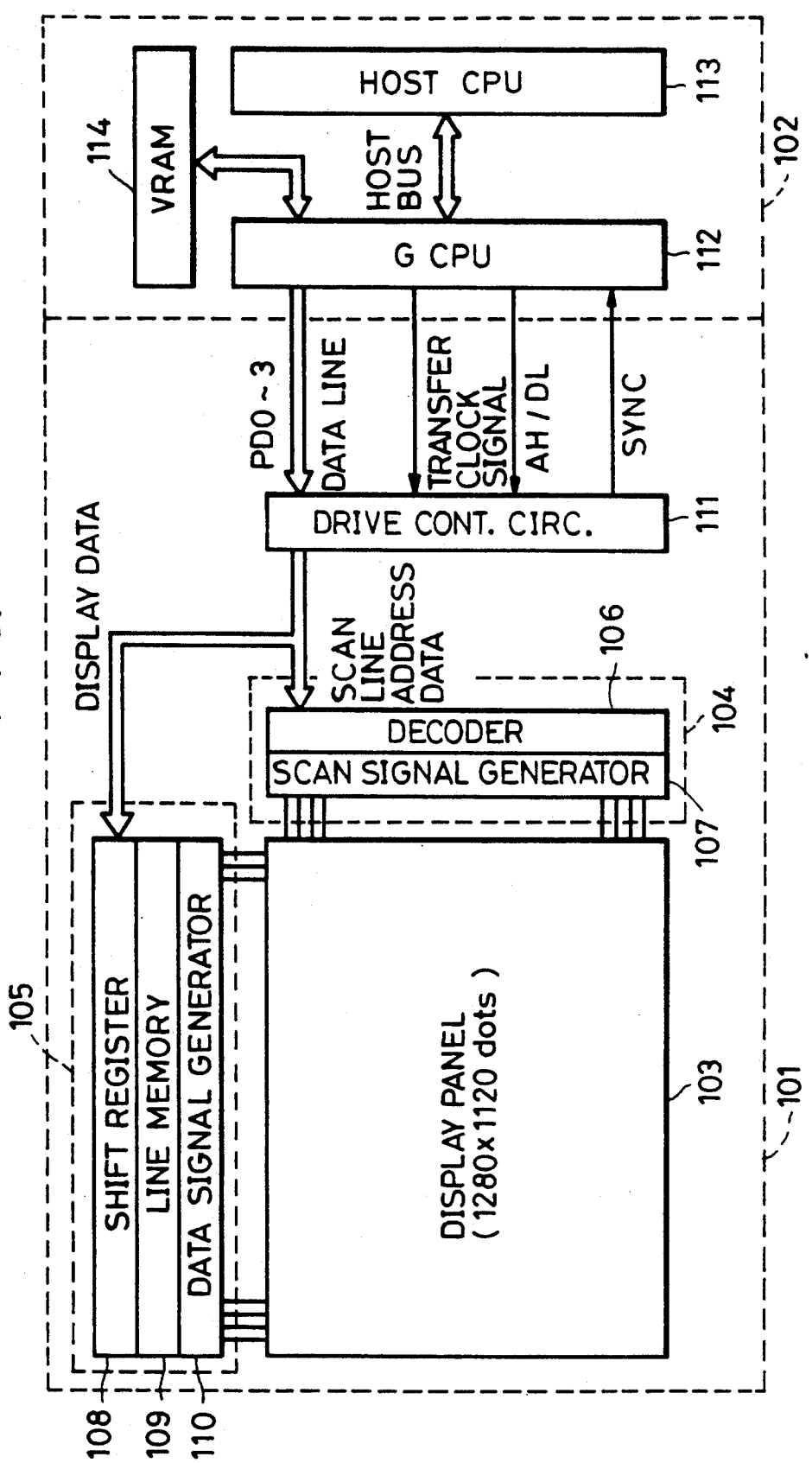
FIG. 4 is a block diagram showing a display apparatus comprising a liquid crystal device utilizing the liquid crystal cell of FIG. 1.
Figure 5:
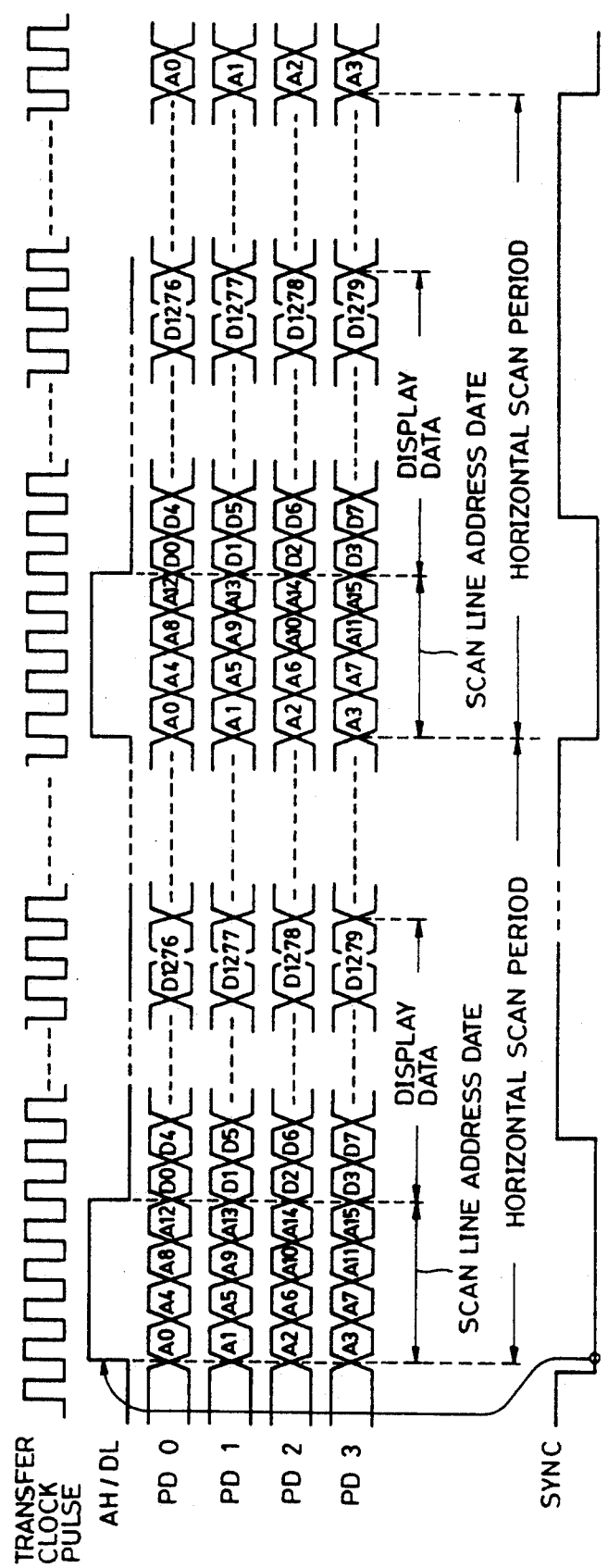
FIG. 5 is a time chart of image data communication showing time correlation between signal transfer and driving with respect to the liquid crystal display apparatus of FIG. 4 and a graphic controller.

Based on the arrangement and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Image data are generated in a graphic controller 102 in an apparatus body and transferred to a display panel 103 by signal transfer means shown in FIG. 4 and 5. The graphic controller 102 principally comprises a CPU (central processing unit, hereinafter referred to as "GCPU") 112 and a VRAM (video-RAM, image data storage memory 114 and is in charge of management and communication of image data between a host CPU 113 and the liquid crystal display apparatus (FLCD) 101. The control method according to the present invention is principally realized in the graphic controller 102. A light source is disposed at the back of the display panel 103.

Hereinbelow, the present invention will be explained more specifically with reference to the following Examples. It is however to be understood that the present invention is not restricted to these Examples.

"Parts" indicates "Parts by Weight" in the following examples.

EXAMPLE 1

Example compound I-119 was synthesized through the following steps:

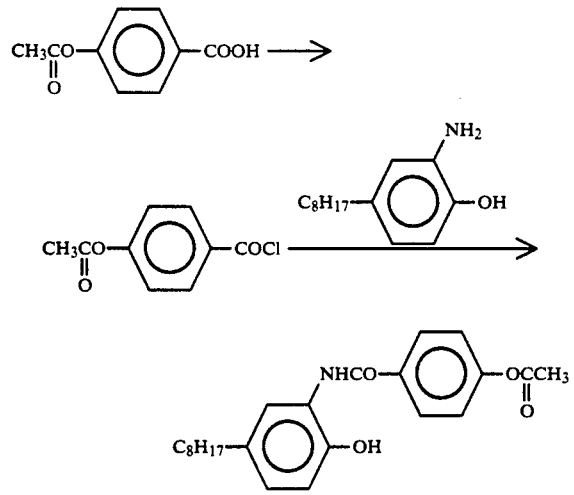

In a 20 ml round-bottom flask, 2.90 g (16.1 m mole) of 4-acetoxybenzoic acid and 3.7 ml of thionyl chloride were placed. To the mixture two drops of N,N-dimethylformamide was added at room temperature under stirring followed by refluxing and stirring for 20 minutes. After the reaction, dry benzene was added into the reaction mixture. Excessive thionyl chloride was distilled off under reduced pressure, followed by distilling-off thereof with benzene. This operation was repeated twice.

In a 100 ml round-bottom flask, the resultant 4-acetoxybenzoic chloride, 3.10 g (15.1 m mole) of 2-amino-4-octylphenol and 40 ml of dioxane were placed and heated to keep inner temperature 85 to 88.5° C. To the mixture, 5.5 ml of pyridine was added dropwise under stirring, followed by heating and stirring for 20 minutes at 85 to 88.5° C. After the reaction, the reaction mixture was cooled with ice and poured into ca. 200 ml of ice water to precipitate a crystal. The crystal was filtered, washed and recrystallized from methanol to obtain 4.10 g of 2-(4-acetoxybenzoylamino)-4-octylphenol (Yield: 70.8%).

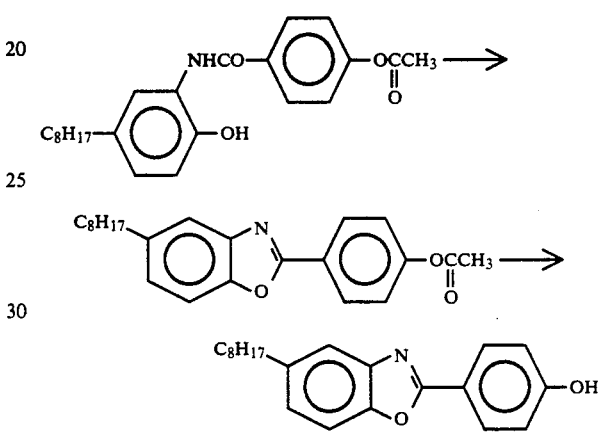

In a 200 ml round-bottom flask, 4.00 g (10.4 m mole) of 2-(4-acetoxybenzoylamino)-4-octylphenol, 0.40 g of p-toluenesulfonic acid monohydrate and 40 ml of 0-dichlorobenzene were placed, followed by heating and stirring for a hour at 188-192° C.

After the reaction, O-dichlorobenzene was distilled off under reduced pressure. To the resultant 1.98 g (30.0 m mole) of potassium hydroxide and 60 ml of ethanol were added, followed by heating and stirring on a water bath kept the temperature at about 75° C. After the reaction, ethanol was distilled off under reduced pressure and water was added to the resultant. To the resultant solution, 6.0 ml (34.0 m mole) of concentrate sulfuric acid was added to precipitate a crystal. Then the crystal was filtered, washed and recrystallized from ethanol to obtain 2.70 g of 2-(4-hydroxyphenyl)-5-octylbenzooxazole (Yield: 80%).

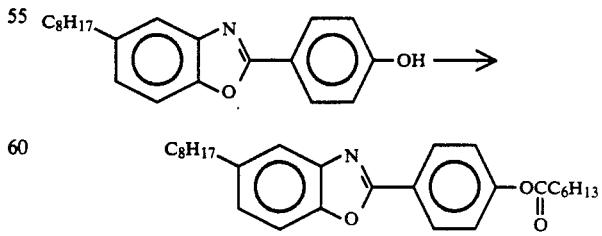

In a 30 ml round-bottom flask, 0.50 g (1.55 m mole) of 2-(4-hydroxyphenyl)-5-octylbenzooxazole, 0.22 g (1.69 m mole) of heptanoic acid and 10 ml of dichloromethane were placed, followed by adding 0.32 g (1.55 m mole) of N,N-dicyclohexylcarbodiimide and 0.04 g of 4-pyrrodinopyridine in order at room temperature under stirring, and stirring at room temperature for 85 minutes. The resultant N,N'-dicyclohexylurea was filtered off and the filtrate was dried under reduced pressure to precipitate a resultant. The resultant was purified by silica gel column chromatography (eluent: toluene) and recrystallized from acetone to obtain 0.41 g of 2-(4-heptanoyloxyphenyl)-5-octylbenzooxazole (Yield: 60.9%).

Phase Transition Temperature (°C.)

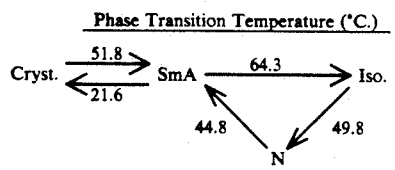

EXAMPLE 2

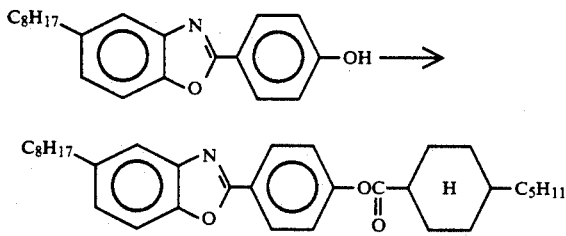

0.47 g of 2-[4-(4-pentylcyclohexylcarbonyloxy) phenyl]-5-octylbenzooxazole (Example Compound IO-230) was prepared by using 0.50 g (1.55 m mole) of 2-(4-hydroxyphenol)-5-octylbenzooxazole and 0.33 g (1.66 m mole) of 4-pentylcyclohexanecarboxylic acid in the same manner as in Example 1. (Yield: 60.4%).

Phase Transition Temperature (°C.)

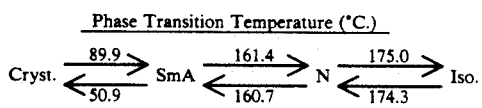

EXAMPLE 3

Example Compound I-74 was synthesized through the following steps.

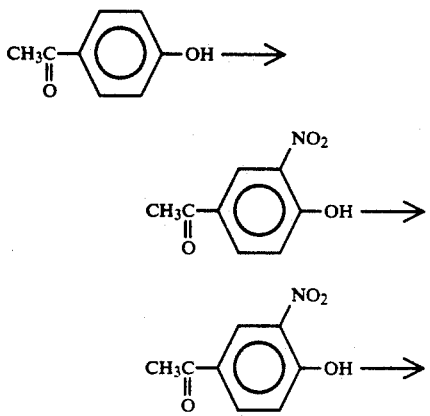

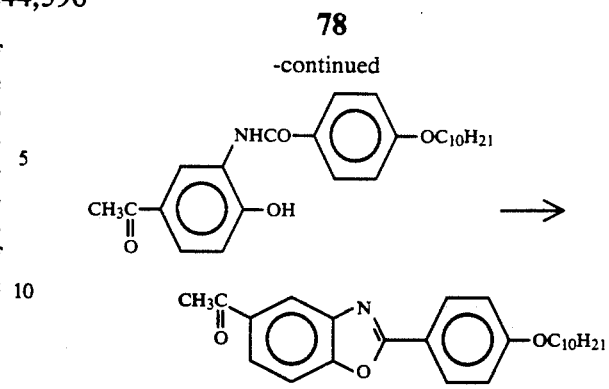

5.00 g (36.7 m mole) of 4-acetylphenol was dissolved in 50 ml of sulfuric acid. To the mixture solution 3.10 ml (40.7 m mole) of nitric acid (60%, d=1.38) was gradually added dropwise, keeping the reaction temperature at 2–10° C. and cooling with ice under stirring.

Then the mixture solution was stirred at the same temperature. After the reaction, the reaction mixture was poured into ice water to precipitate a crystal. The crystal was filtered, washed with water and recrystallized from methanol to obtain 5.84 g of 2-nitro-4-acetylphenol (Yield: 79.8%).

In a 300 ml three-neck flask, 5.00 g (27.6 m mole) of 2-nitro-4-acetylphenol and 75 ml of 2N-sodium hydroxide solution were placed. To the mixture solution, a solution, which 25.00 g of sodium hydrosulfite was dissolved in 75 ml to water, was added dropwise in 10 minutes. Then the mixture solution was stirred for 20 minutes at room temperature to precipitate a crystal. The crystal was filtered and recrystallized from a mixture solvent of methanol-water to obtain 1.63 g of 2-amino-4-acetylphenol (Yield: 39.1%).

3.10 g (11.1 m mole) of 4-decyloxybenzoic acid was acid-chlorined by thionyl chloride, dissolved in 15 ml of dioxane and poured into a 100 ml three-neck flask. To the mixture solution, 1.60 g (10.6 m mole) of 2-amino-4-acetylphenol and 15 ml of dioxane was added in order, followed by heating until about 80° C. and stirring. Then 3.7 ml of pyridine was gradually added dropwise to the mixture solution. After adding, the mixture solution was heated and stirred for 20 minutes at 86–89.5° C.

After the reaction, the reaction solution was poured into 100 ml of water to precipitate a crystal. The crystal was filtered, washed with water and dried with milabilite by dissolving in a mixture solvent of ethyl acetate-toluene. The solvent was dried under reduced pressure to precipitate a resultant. To the resultant, 40 ml of O-dichlorobenzene and 0,40 g of p-toluenesulfuric acid monohydrate were added, followed by heating and stirring at 188–193° C.

After the reaction, O-dichlorobenzene was distilled off under reduced pressure to precipitate a resultant. The resultant was purified by silica gel column chromatography (eluent: toluene/ethyl acetate: 100/1) and recrystallized from a mixture solvent of toluenemethanol to obtain 3.11 g of 2-(4-decyloxyphenyl)-5-acetylbenzooxazole (Yield: 74.5%).

Phase Transition Temperature (°C.)

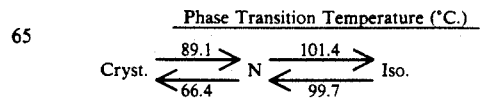

EXAMPLE 4

2-(4-butylphenyl)-5-acetylbenzooxazole (Example Compound I-65) was prepared in the same manner as in Example 3.

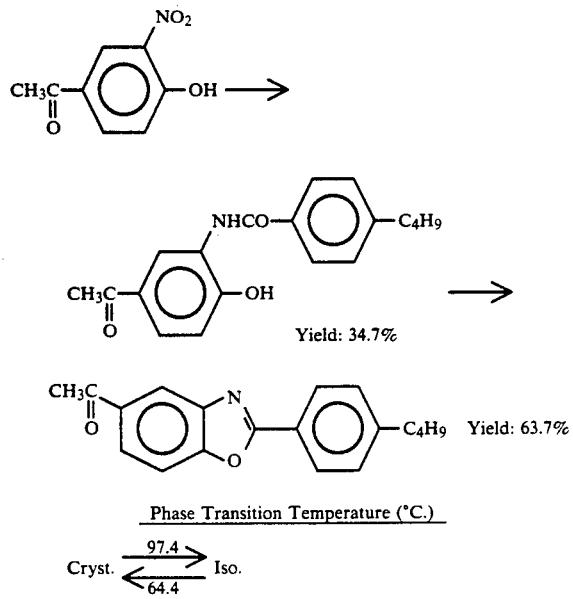

Phase Transition Temperature (°C.)

Cryst. $\xrightleftharpoons[64.4]{97.4}$ Iso.

EXAMPLE 5

2-(4-octyloxyphenyl)-5-undecanoylbenzooxazole (Example Compound I-85) was prepared in the same manner as in Example 3.

$C_{10}H_{21}\underset{O}{\overset{\|}{C}}$—⟨⟩—OH $\xrightarrow{82.4\%}$ $C_{10}H_{21}\underset{O}{\overset{\|}{C}}$—⟨NO₂⟩—OH $\xrightarrow{60.0\%}$ $C_{10}H_{21}\underset{O}{\overset{\|}{C}}$—⟨NO₂⟩—OH $\xrightarrow{78.5\%}$ $C_{10}H_{21}\underset{O}{\overset{\|}{C}}$—⟨NHCO—⟨⟩—OC₈H₁₇ / OH⟩ $\xrightarrow[\text{Yield}]{74.6\%}$ $C_{10}H_{21}\underset{O}{\overset{\|}{C}}$—⟨benzoxazole⟩—⟨⟩—OC₈H₁₇

Phase Transition Temperature (°C.)

-continued

Cryst. $\xrightarrow{106.9}$ SmA $\xrightleftharpoons[119.2]{120.4}$ Iso.

$\underset{96.9}{\searrow}$ $\swarrow{103.8}$

SmC

EXAMPLE 6

Example Compound I-51 was synthesized through the following steps:

$CH_3\underset{O}{\overset{\|}{C}}$—⟨benzoxazole⟩—⟨⟩—OC₁₀H₂₁ →

$HO\underset{O}{\overset{\|}{C}}$—⟨benzoxazole⟩—⟨⟩—OC₁₀H₂₁ →

$C_8H_{17}O\underset{O}{\overset{\|}{C}}$—⟨benzoxazole⟩—⟨⟩—OC₁₀H₂₁

1.61 g (40.3 m mole) of sodium hydroxide was dissolved in 10.7 ml of water, followed by cooling at −7.5—5° C. on ice-common salt bath. To the solution, 0.66 ml (25.6 m mole) of bromic acid was added dropwise under stirring, followed by cooling at ca. −5° C. To the mixture solution, 4.2 ml of dioxane was added dropwise under stirring to prepare sodium hypobromite solution. In a 200 ml three-neck flask, 1.50 g (3.81 m mole) of (4-decyloxyphenyl)-5-acetylbenzooxazole synthesized in Example 3, 30 ml of dioxane and 2.5 ml of water were placed, followed by keeping inner temperature below 5° C. under cooling with ice and stirring. To the mixture solution, the above-mentioned sodium hypobromite solution was added dropwise, and the reaction temperature was raised up to 45° C. and maintained for 90 minutes. After the reaction, the reaction mixture was poured into 150 ml of water. To the resultant reaction mixture, 3.2 ml of chloric acid was added to show pH=1 to precipitate a crystal. The crystal was filtered and washed with water, followed by recrystallizing from a mixture solvent of acetone-methanol to obtain 1.13 g of 2-(4-decyloxyphenyl)-5-carboxybenzooxazole (Yield: 75.0%).

In a 30 ml round-bottom flask, 0.30 g (0.76 m mole) of 2-(4-decyloxyphenyl)-5-carboxybenzooxazole, 0.11 g (0,84 m mole) of octanol and 8 ml of dichloromethane were placed. To the mixture solution 0.16 g (0.78 m mole) of N,N'-dicyclohexycarbodiimide and 0.04 g of 4-pyrrolidinopyridine were added in order under stirring at room temperature, followed by stirring for 8 hours at room temperature to precipitate N,N'-dicyclohexylurea. The resultant N,N'-dicyclohexylurea was filtered off and the filtrate was dried under reduced pressure. The resultant was purified by silica gel column chromatography (eluent: toluene) and recrystallized twice from acetone to obtain 0.19 g of 2-(4-decyloxyphenyl)-5-octyloxycarbonyl benzooxazole (Yield: 49.3%).

Phase Transition Temperature (°C.)

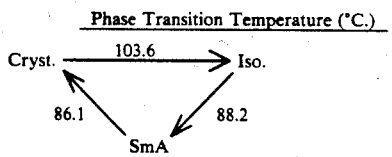

EXAMPLE 7

Example Compound I-190 was synthesized through the following steps.

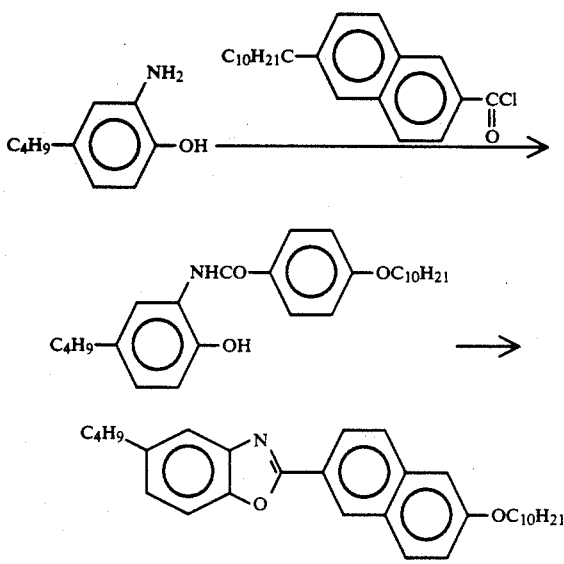

In a 50 ml three-neck flask, 0.40 g (2.42 m mole) of 2-amino-4-butylphenol, 0.85 g (2.74 m mole) of 6-decyloxy-2-naphthoic acid chloride and 10 ml of dioxane were placed. To the mixture, 0.81 ml of pyridine was added dropwise under stirring at ca. 75° C. of mixture temperature. After the reaction, the reaction mixture was poured into 80 ml of water to precipitate a crystal. The crystal was filtered, washed with water and recrystallized from acetone to obtain 1.00 g of 2-(6-decyloxy-2-naphthoylamino)-4-butylphenol (Yield: 86.5%).

0.95 g (2.00 m mole) of 2-(6-decyloxy-2-naphthoylamino)-4-butylphenol, 0.07 g of P-toluenesulfuric acid monohydrate and 8 ml of O-dichlorobenzene were placed in a 20 ml round-bottom flask, followed by heating and stirring for 30 minutes at 200–203° C. After the reaction, O-dichlorobenzene was distilled off under reduced pressure. The resultant was recrystallized from ethyl acetate to obtain a crystal. The crystal was refined by silica gel column chromatography (eluent: toluene/-hexane=1/1), and recrystallized from acetone to obtain 0.56 g of 2-(6-decyloxy-2-naphthyl)-5-butylbenzooxazole (Yield: 61.3%).

Phase Transition Temperature (°C.)

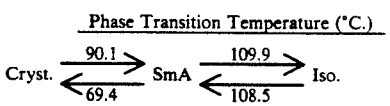

EXAMPLE 8

2-(3-fluoro-4-octyloxyphenyl)-5-butylbenzooxazole (Example Compound I-162) was prepared in the same manner as in Example 7.

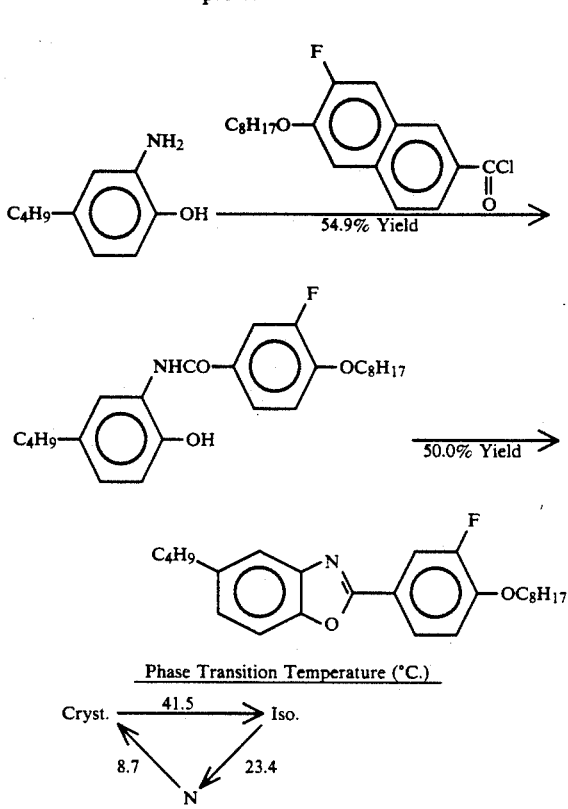

EXAMPLE 9

2-(4-decyloxyphenyl)-5-[4-(S-(+)-2-octyloxycarbonyl)phenyl oxycarbonylbenzooxazole (Example I-220) was prepared in the same manner as in Example 6 by using p-hydroxyphenylbenzoic acid s-(+)-2-octylester, which was synthesized through the following steps and 2-(4-decyloxyphenyl)-5-carboxybenzooxazole synthesized in Example 6.

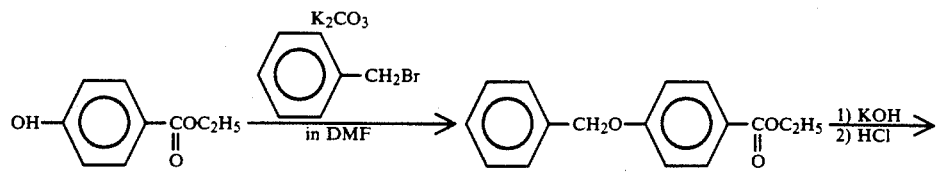

-continued

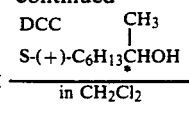
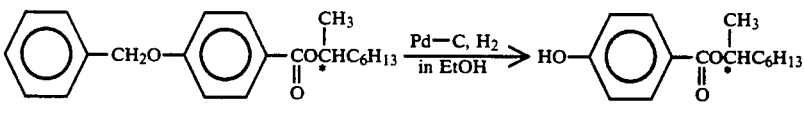
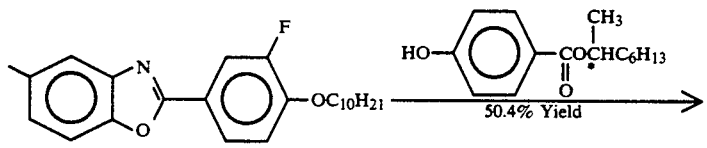
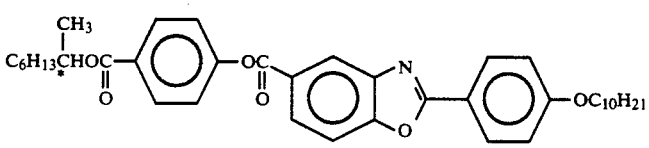

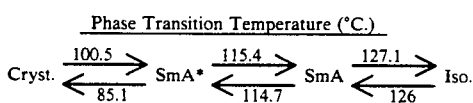

EXAMPLE 10

2-(4-methoxycarbonylphenyl)-5-butylbenzooxazole was synthesized through the following steps in the same manner as in Example 7.

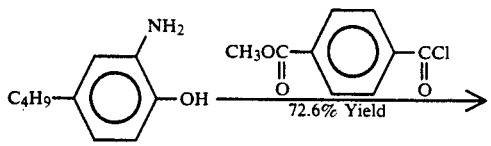

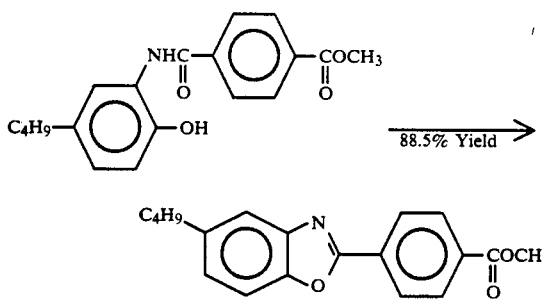

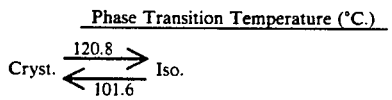

EXAMPLE 11

Example Compound I-141 was synthesized in the following manner.

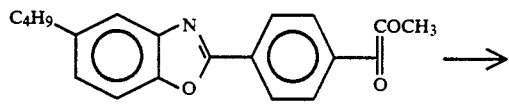
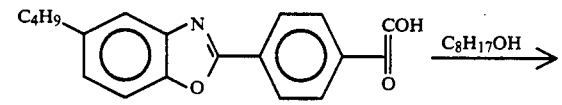
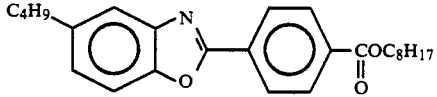

0.47 of potassium hydroxide and 30 ml of ethanol were placed in a 100 ml round-bottom flask, followed by heating to dissolve. To the mixture, 0.90 g (2.91 m mole) of 2-(4-methoxy-carbonyl(phenyl)-5-butylbenzooxazole synthesized in Example 10 was added, followed by refluxing and stirring for 1 hour to obtain a crystal. The crystal was filtered and dissolved in 30 ml of water at room temperature, followed by addition of chloric acid to precipitate a crystal. The crystal was filtered, washed with water, then with acetone to obtain 0.75 g of 2-(4-carboxy-phenyl 2-5-butylbenzooxazole (Yield: 87.3%).

0.20 g (0.68 m mole) of 2-(4-carboxyphenyl)-5-butyl-benzooxazole was esterized in the same manner as in Example 6 to obtain 0.22 g of 2-(4-octyl-oxycarbonyl-phenyl)-5-butylbenzooxazole (Yield: 79.7%).

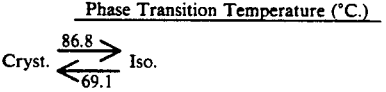

EXAMPLE 12

A liquid crystal composition A was prepared by mixing the following compounds in respectively indicated proportions.

| Structural formula | wt. parts |
|---|---|
| C₆H₁₃O—⟨⟩—(N=N)—C₈H₁₇ | 46.14 |
| C₉H₁₉O—⟨⟩—(N=N)—C₈H₁₇ | 23.07 |
| C₈H₁₇O—⟨⟩—(N=N)—C₁₀H₂₁ | 11.54 |
| C₃H₇—⟨H⟩—CO·O—⟨⟩—(N=N)—C₁₁H₂₃ | 3.56 |
| C₄H₉—⟨H⟩—CO·O—⟨⟩—(N=N)—C₁₁H₂₃ | 3.56 |
| C₅H₁₁—⟨H⟩—CO·O—⟨⟩—(N=N)—C₂₂H₂₃ | 7.13 |
| C₁₂H₂₅—(N=N)—⟨⟩—OCH₂C*HFC₆H₁₃ | 2.50 |
| C₁₀H₂₁—(N=N)—⟨⟩—OCH₂C*HFC₆H₁₃ | 2.50 |

The liquid crystal composition A was further mixed with the following Example Compound No. I-190 in the proportions indicated below to provide a liquid crystal composition B.

| Ex. Comp. No. | Structural formula | wt. parts |
|---|---|---|
| I-190 | 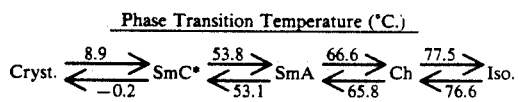 | 5 |
| | Composition A | 95 |

The liquid crystal composition B showed the following phase transition series.

Phase Transition Temperature (°C.)

$$\text{Cryst.} \underset{-0.2}{\overset{8.9}{\rightleftarrows}} \text{SmC*} \underset{53.1}{\overset{53.8}{\rightleftarrows}} \text{SmA} \underset{65.8}{\overset{66.6}{\rightleftarrows}} \text{Ch} \underset{76.6}{\overset{77.5}{\rightleftarrows}} \text{Iso.}$$

EXAMPLE 13

Two 0.7 mm-thick glass plates were provided and respectively coated with an ITO file to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 seconds and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then the liquid crystal composition B prepared in Example 12 was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of the magnitude of spontaneous polariziation Ps and an optical response time (time from voltage application until the transmittance change reaches 90% of the maximum under the application of a peak-to-peak voltage Vpp of 20 V in combination with right-angle cross-nicol polarizers).

The results are shown below.

| | 10° C. | 30° C. | 45° C. |
|---|---|---|---|
| Response time (μsec) | 438 | 205 | 124 |
| Ps (nC/cm²) | 3.49 | 2.61 | 1.60 |

EXAMPLE 14

A liquid crystal composition C was prepared in the same manner as in Example 12.

| Structural formula | wt. parts |
|---|---|
| C₆H₁₃O—⟨⟩—(N=N)—C₈H₁₇ | 51.57 |
| C₉H₁₉O—⟨⟩—(N=N)—C₈H₁₇ | 25.79 |

-continued

| Structural formula | wt. parts |
|---|---|
| C$_8$H$_{17}$O—⬡—[pyrimidine]—C$_{10}$H$_{21}$ | 12.89 |
| C$_3$H$_7$—[H]—COO—⬡—[pyrimidine]—C$_{11}$H$_{23}$ | 1.19 |
| C$_4$H$_9$—[H]—COO—⬡—[pyrimidine]—C$_{11}$H$_{23}$ | 1.19 |
| C$_5$H$_{11}$—[H]—COO—⬡—[pyrimidine]—C$_{11}$H$_{23}$ | 2.37 |
| C$_{12}$H$_{26}$—[pyrimidine]—⬡—OCH$_2$C*HC$_6$H$_{13}$ (F) | 2.50 |
| C$_{10}$H$_{21}$—[pyrimidine]—⬡—OCH$_2$C*HC$_6$H$_{13}$ (F) | 2.50 |

The liquid crystal composition C was further mixed with the following Example Compound No. I-230 in the proportions indicated below to provide a liquid crystal composition D.

| Ex. Comp. No. | Structural formula | wt. parts |
|---|---|---|
| I-230 | C$_8$H$_{17}$—[benzoxazole]—⬡—OC(O)—[H]—C$_5$H$_{11}$ | 10 |
| | Composition C | 90 |

The liquid crystal composition D showed the following phase transition series.

Phase Transition Temperature (°C.)

$$\text{Cryst.} \xrightarrow{8.4} \text{SmC*} \xrightarrow{53.2} \text{SmA} \xrightarrow{68.4} \text{Ch} \xrightarrow{76.8} \text{Iso.}$$

A ferroelectric liquid crystal device was prepared in the same manner as in Example 13 except for using the composition D. The ferroelectric liquid crystal device was subjected to measurement of the magnitude of spontaneous polarization Ps and optical response time in the same manner as in Example 13, whereby the following results were obtained.

| | 10° C. | 30° C. | 45° C. |
|---|---|---|---|
| Response time (μsec) | 512 | 225 | 110 |
| Ps (nC/cm$^2$) | 3.03 | 2.02 | 1.25 |

EXAMPLE 15

A liquid crystal composition E was prepared by mixing the following compounds in respectively indicated proportions.

| Structural formula | wt. parts |
|---|---|
| C$_7$H$_{15}$—[pyrimidine]—⬡—OC$_9$H$_{19}$ | 12 |
| C$_{11}$H$_{23}$—[pyrimidine]—⬡—OC$_6$H$_{13}$ | 10 |
| C$_8$H$_{17}$—[pyrimidine]—⬡—O(CH$_2$)$_3$C*HC$_2$H$_5$ (CH$_3$) | 10 |
| C$_{10}$H$_{21}$—[pyrimidine]—⬡—O(CH$_2$)$_4$C*HOCH$_3$ (CH$_3$) | 3 |
| C$_8$H$_{17}$—[pyrimidine]—⬡—⬡—OC$_6$H$_{13}$ | 8 |

| Structural formula | wt. parts |
|---|---|
| C₆H₁₃O–⌬–O–CO–⌬⌬–OC₉H₁₉ | 4 |
| C₃H₇–[H]–CO–O–⌬–⌬(N,N pyrazine)–C₁₁H₂₃ | 6 |
| C₈H₁₇–[H]–CO–O–⌬–⌬(N,N pyrazine)–C₁₁H₂₃ | 2 |
| C₅H₁₁–[H]–CO–O–⌬–⌬(N,N pyrazine)–C₁₁H₂₃ | 8 |
| C₁₀H₂₁O–⌬–CO–O–⌬–OCH₂C*H(CH₃)C₂H₅ | 15 |
| C₄H₉–[H]–CH₂O–⌬–⌬(N,N pyrazine)–C₆H₁₃ | 7 |
| C₅H₁₁–[H]–CH₂O–⌬–⌬(N,N pyrazine)–C₆H₁₃ | 7 |
| C₉H₁₉O–⌬–OCH₂–⌬–⌬–C₇H₁₅ | 4 |
| C₆H₁₃C*H(CH₃)O–⌬–CO–O–⌬–⌬–OC*(CH₃)(CO)C₄H₉ | 2 |
| C₁₂H₂₅–⌬(N,N pyrazine)–⌬–OCC*H(Cl)–C*H(CH₃)C₂H₅ | 2 |

The liquid crystal composition E was further mixed with the following Example Compounds in the proportions indicated below to provide a liquid crystal composition F.

| Ex. Comp. No. | Structural formula | wt. parts |
|---|---|---|
| 1-5 | C₁₀H₂₁CO(O)–⌬(benzoxazole)–⌬–C₁₂H₂₅ | 2 |
| 1-18 | C₈H₁₇CO(O)–⌬(benzoxazole)–⌬–OC₁₂H₂₅ | 2 |
| 1-71 | C₁₀H₂₁C(O)–⌬(benzoxazole)–⌬–OC₁₄H₂₉ | 2 |
| | Composition E | 94 |

A ferroelectric liquid crystal device was prepared in the same manner as in Example 13 except for using the composition F. The ferroelectric liquid crystal device was subjected to measurement of optical response time in the same manner as in Example 13, whereby the following results were obtained.

|  | 10° C. | 25° C. | 40° C. |
| --- | --- | --- | --- |
| Response time ($\mu$sec) | 738 | 358 | 195 |

COMPARATIVE EXAMPLE 1

A ferroelectric liquid crystal device was prepared in the same manner as in Example 13 except that the liquid crystal composition F prepared in Example 15 was injected into a cell. The measured values of the response time of the device were as follows:

|  | 10° C. | 25° C. | 40° C. |
| --- | --- | --- | --- |
| Response time ($\mu$sec) | 784 | 373 | 197 |

EXAMPLE 16

A liquid crystal composition G was prepared by mixing the following Example Compounds in place of Example Compound I-5, I-18 and I-71 used in Example 15 in the indicated proportions.

| Ex. Comp. No. | Structural formula | wt. parts |
| --- | --- | --- |
| I-105 | $C_6H_{13}$—[benzoxazole]—[phenyl]—$CC_9H_{19}$ (C=O) | 2 |
| I-131 | $C_{10}H_{21}O$—[benzoxazole]—[phenyl]—$OCC_{10}H_{21}$ (C=O) | 2 |
| I-170 | $C_{15}H_{31}$—[benzoxazole]—[phenyl with F]—$OC_{14}H_{29}$ | 3 |
| Composition E | | 93 |

A ferroelectric liquid crystal device was prepared in the same manner as in Example 13 except that the above liquid crystal composition G was used, and the device was subjected to measurement of optical response time. The results of the measurement are shown below.

|  | 10° C. | 25° C. | 40° C. |
| --- | --- | --- | --- |
| Response time ($\mu$sec) | 732 | 354 | 193 |

EXAMPLE 17

A liquid crystal composition H was prepared by mixing the following Example Compounds in place of Example Compound I-105, I-131 and I-170 used in Example 16 in the indicated proportions.

| Ex. Comp. No. | Structural formula | wt. parts |
| --- | --- | --- |
| I-127 | $C_7H_{15}O$—[benzoxazole]—[phenyl]—$OCCHC_8H_{17}$ with F, =O | 2 |
| I-180 | $C_8H_{17}O$—[benzoxazole]—[pyridine N,N]—$OC_8H_{17}$ | 3 |
| I-198 | $C_{12}H_{25}O$—[benzoxazole]—[naphthyl]—$OCH_2CHC_2H_5$ with $CH_3$ | 3 |
| Composition E | | 92 |

A ferroelectric liquid crystal device was prepared in the same manner as in Example 13 except that the above liquid crystal composition H was used, and the device was subjected to measurement of optical response time. The results of the measurement are shown below.

|  | 10° C. | 25° C. | 40° C. |
| --- | --- | --- | --- |
| Response time ($\mu$sec) | 695 | 340 | 186 |

EXAMPLE 18

A liquid crystal composition I was prepared by mixing the following Example Compounds in respectively indicated proportions.

| Structural formula | wt. parts |
|---|---|
| 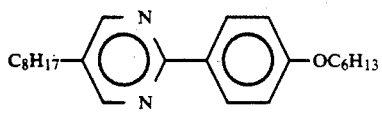 C$_8$H$_{17}$—[pyrazine]—[phenyl]—OC$_6$H$_{13}$ | 10 |
| 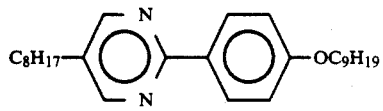 C$_8$H$_{17}$—[pyrazine]—[phenyl]—OC$_9$H$_{19}$ | 5 |
| 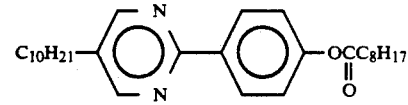 C$_{10}$H$_{21}$—[pyrazine]—[phenyl]—OCC$_8$H$_{17}$ ‖ O | 7 |
| 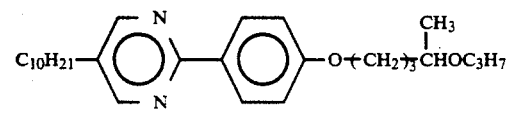 C$_{10}$H$_{21}$—[pyrazine]—[phenyl]—O(CH$_2$)$_3$CHOC$_3$H$_7$ with CH$_3$ | 7 |
| 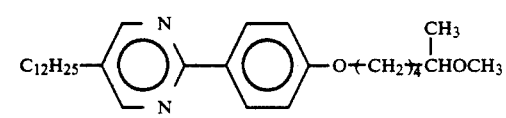 C$_{12}$H$_{25}$—[pyrazine]—[phenyl]—O(CH$_2$)$_4$CHOCH$_3$ with CH$_3$ | 6 |
| 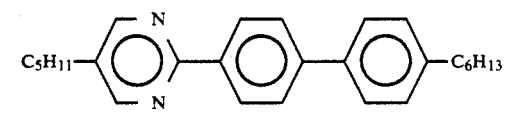 C$_5$H$_{11}$—[pyrazine]—[phenyl]—[phenyl]—C$_6$H$_{13}$ | 5 |
| 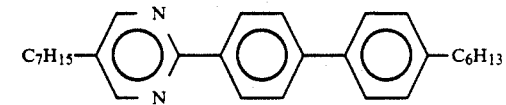 C$_7$H$_{15}$—[pyrazine]—[phenyl]—[phenyl]—C$_6$H$_{13}$ | 5 |
| 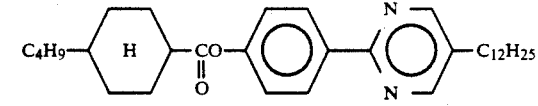 C$_4$H$_9$—[cyclohexyl-H]—CO—O—[phenyl]—[pyrimidine]—C$_{12}$H$_{25}$ | 8 |
| 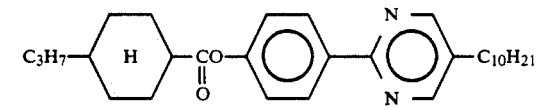 C$_3$H$_7$—[cyclohexyl-H]—CO—O—[phenyl]—[pyrimidine]—C$_{10}$H$_{21}$ | 8 |
| 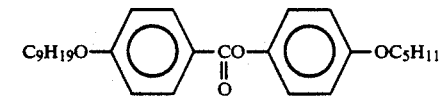 C$_9$H$_{19}$O—[phenyl]—CO—O—[phenyl]—OC$_5$H$_{11}$ | 20 |
| 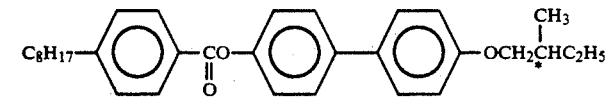 C$_8$H$_{17}$—[phenyl]—CO—O—[phenyl]—[phenyl]—OCH$_2$CHC$_2$H$_5$* with CH$_3$ | 5 |
| 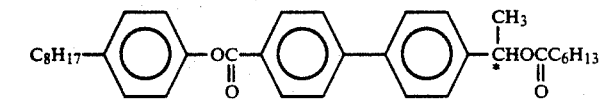 C$_8$H$_{17}$—[phenyl]—O—CO—[phenyl]—[phenyl]—CHOCC$_6$H$_{13}$* with CH$_3$, ‖O | 5 |
| 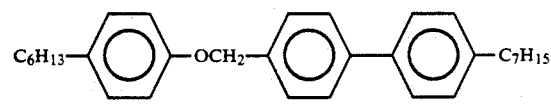 C$_6$H$_{13}$—[phenyl]—OCH$_2$—[phenyl]—[phenyl]—C$_7$H$_{15}$ | 6 |

| Structural formula | wt. parts |
|---|---|
| 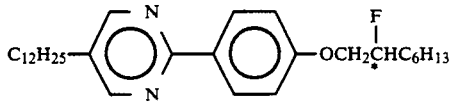 | 3 |

The liquid crystal composition I was further mixed with the following Example Compounds in the proportions indicated below to provide a liquid crystal composition J.

| Ex. Comp. No. | Structural formula | wt. parts |
|---|---|---|
| I-79 | 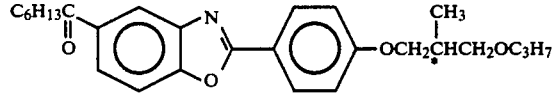 | 2 |
| I-154 | 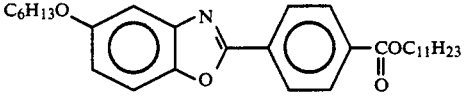 | 2 |
| I-185 | 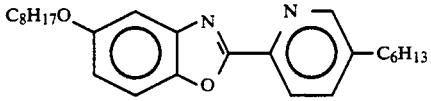 | 3 |
| | Composition I | 93 |

A ferroelectric liquid crystal device was prepared in the same manner as in Example 13 except for using the composition J. The ferroelectric liquid crystal device was subjected to measurement of response time and observation of a switching state etc. in the same manner as in Example 13.

In the ferroelectric liquid crystal device, a monodomain with a good and uniform alignment characteristic was observed. The following results were obtained.

| | 10° C. | 25° C. | 40° C. |
|---|---|---|---|
| Response time (μsec) | 587 | 292 | 151 |

A clear switching motion was observed during driving and a good bistability was shown when the electric field was removed.

COMPARATIVE EXAMPLE 2

A ferroelectric liquid crystal device was prepared in the same manner as in Example 13 except that the liquid crystal composition I prepared in Example 18 was injected into a cell. The measured values of the response time of the device were as follows:

| | 10° C. | 25° C. | 40° C. |
|---|---|---|---|
| Response time (μsec) | 653 | 317 | 159 |

EXAMPLE 19

A liquid crystal composition K was prepared by mixing the following example compounds in place of Example Compound I-79, I-154 and I-185 used in Example 18 in the indicated proportions.

| Ex. Comp. No. | Structural formula | wt. parts |
|---|---|---|
| I-164 | 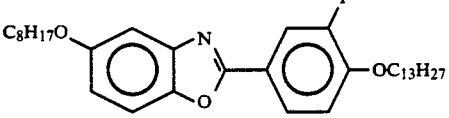 | 3 |
| I-194 | 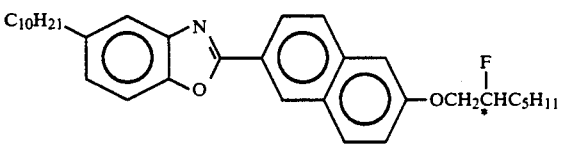 | 2 |

-continued

| Ex. Comp. No. | Structural formula | wt. parts |
|---|---|---|
| I-225 | $C_6H_{13}$—[benzoxazole]—[phenyl]—OC(=O)—[phenyl]—$C_8H_{17}$ | 2 |
| | Composition I | 93 |

A ferroelectric liquid crystal device was prepared in the same manner as in Example 13 except that the above liquid crystal composition K was used, and the device was subjected to measurement of optical response time and observation of a switching state, etc. In the ferroelectric liquid crystal device, a monodomain with a good and uniform alignment characteristic was observed. The following results were obtained.

| | 10° C. | 25° C. | 40° C. |
|---|---|---|---|
| Response time (μsec) | 568 | 282 | 146 |

EXAMPLE 20

A liquid crystal composition L was prepared by mixing the following example compounds in place of Example Compound I-164, I-194 and I-225 used in Example 19 in the indicated proportions.

A ferroelectric liquid crystal device was prepared in the same manner as in Example 13 except that the above liquid crystal composition L was used, and the device was subjected to measurement of optical response time and observation of a switching state, etc. In the ferroelectric liquid crystal device, a monodomain with a good and uniform alignment characteristic was observed.
The following results were obtained.

| | 10° C. | 25° C. | 40° C. |
|---|---|---|---|
| Response time (μsec) | 598 | 295 | 152 |

EXAMPLE 21

A liquid crystal composition M was prepared by mixing the following Example Compounds in respectively indicated proportions.

| Ex. Comp. No. | Structural formula | wt. parts |
|---|---|---|
| I-171 | $C_8H_{17}$—[benzoxazole]—[phenyl with $CF_3$]—$OC_8H_{17}$ | 3 |
| I-213 | $C_8H_{17}O$—[benzoxazole]—[thiophene(S)]—$C_6H_{13}$ | 3 |
| I-232 | $C_7H_{15}O$—[benzoxazole]—[phenyl]—CO(=O)—[cyclohexyl H]—$C_3H_7$ | 1.5 |
| | Composition I | 92.5 |

| Structural formula | wt. parts |
|---|---|
| $C_9H_{19}$—[pyrimidine(N,N)]—[phenyl]—$OC_9H_{19}$ | 6 |
| $C_{10}H_{21}$—[pyrimidine(N,N)]—[phenyl]—$OC_8H_{17}$ | 6 |
| $C_8H_{17}$—[pyridine(N)]—[phenyl]—$O$—$(CH_2)_2$—$\overset{*}{C}H(CH_3)C_2H_5$ | 7 |

-continued

| Structural formula | wt. parts |
|---|---|
| C₁₁H₂₃O–[pyrimidine]–[phenyl]–O(CH₂)₂*CH(CH₃)C₂H₅ | 14 |
| C₁₀H₂₁–[pyridine]–[phenyl]–C₆H₁₃ | 8 |
| C₆H₁₃–[pyrimidine]–[phenyl]–[phenyl]–C₄H₉ | 4 |
| C₈H₁₇–[phenyl]–[pyridine]–[phenyl]–OC₅H₁₁ | 2 |
| C₃H₇–[H cyclohexyl]–CO-O–[phenyl]–[pyrimidine]–C₁₂H₂₅ | 10 |
| C₅H₁₁–[H cyclohexyl]–CO-O–[phenyl]–[pyrimidine]–C₁₂H₂₅ | 5 |
| C₁₀H₂₁O–[phenyl]–CS(=O)–[phenyl]–OC₈H₁₇ | 10 |
| C₆H₁₃–[phenyl]–CO-O–[phenyl]–[phenyl]–OCH₂CH(CH₃)C₂H₅ | 7 |
| C₃H₇–[H cyclohexyl]–CH₂O–[phenyl]–[pyrimidine]–C₈H₁₇ | 7 |
| C₁₀H₂₁–[phenyl]–[phenyl]–OCH₂–[phenyl]–C₇H₁₅ | 5 |
| C₁₂H₂₅–[pyrimidine]–[phenyl]–OCH₂*CHF–C₅H₁₁ | 2 |
| C₅H₁₁–[H cyclohexyl]–CO-O–[phenyl]–OCH₂*CHF–C₆H₁₃ | 2 |
| C₁₂H₂₅O–[phenyl]–[pyridine]–CO-O(CH₂)₃*CH(CH₃)C₂H₅ | 2 |

-continued

| Structural formula | wt. parts |
|---|---|
| C$_{12}$H$_{25}$O—⟨C$_6$H$_4$⟩—⟨pyridine(N,N)⟩—O(CH$_2$)$_3$CH(CH$_3$)OC$_3$H$_7$ | 3 |

The liquid crystal composition M was further mixed with the following Example Compounds in the proportions indicated below to provide a liquid crystal composition N.

| Ex. Comp. No. | Structural formula | wt. parts |
|---|---|---|
| 1-55 | C$_8$H$_{17}$OC(O)—⟨benzoxazole⟩—⟨C$_6$H$_4$⟩—OCC$_9$H$_{19}$(O) | 2 |
| 1-78 | C$_6$H$_{13}$C(O)—⟨benzoxazole⟩—⟨C$_6$H$_3$F⟩—OC$_8$H$_{17}$ | 2 |
| 1-202 | C$_8$H$_{17}$O—⟨benzoxazole⟩—⟨naphthalene⟩—OCH(CH$_3$)C$_8$H$_{17}$ | 3 |
| Composition M | | 93 |

A ferroelectric liquid crystal device was prepared in the same manner as in Example 13 except for using the composition N. The ferroelectric liquid crystal device was subjected to measurement of response time and observation of a switching state etc., in the same manner as in Example 13.

In the ferroelectric liquid crystal device, a monodomain with a good and uniform alignment characteristic was observed. The following results were obtained.

|  | 10° C. | 25° C. | 40° C. |
|---|---|---|---|
| Response time (μsec) | 625 | 322 | 175 |

COMPARATIVE EXAMPLE 3

A ferroelectric liquid crystal device was prepared in the same manner as in Example 13 except that the liquid crystal composition M prepared in Example 21 was injected into a cell. The measured values of the response time of the device were as follows:

|  | 10° C. | 25° C. | 40° C. |
|---|---|---|---|
| Response time (μsec) | 668 | 340 | 182 |

EXAMPLE 22

A liquid crystal composition O was prepared by mixing the following example compounds in place of Example Compound I-55, I-78 and I-202 used in Example 21 in the indicated proportions.

| Ex. Comp. No. | Structural formula | wt. parts |
|---|---|---|
| I-136 | C$_{12}$H$_{25}$O—⟨benzoxazole⟩—⟨C$_6$H$_4$⟩—OCC(O)CH(CH$_3$)OC$_5$H$_{11}$* | 2 |
| I-176 | C$_7$H$_{15}$O—⟨benzoxazole⟩—⟨C$_6$H$_3$(CH$_3$)⟩—OC$_{15}$H$_{31}$ | 3 |
| I-210 | C$_{10}$H$_{21}$C(O)—⟨benzoxazole⟩—⟨naphthalene⟩—OCH$_2$CH(CH$_3$)CH$_2$C$_2$H$_5$ | 3 |
| Composition M | | 92 |

A ferroelectric liquid crystal device was prepared in the same manner as in Example 13 except that the above liquid crystal composition O was used, and the device was subjected to measurement of optical response time and observation of a switching state, etc. In the ferroelectric liquid crystal device, a monodomain with a good and uniform alignment characteristic was observed. The following results were obtained.

|  | 10° C. | 25° C. | 40° C. |
|---|---|---|---|
| Response time (μsec) | 613 | 316 | 176 |

EXAMPLE 23

A liquid crystal composition P was prepared by mixing the following example compounds in place of Example Compound I-136, I-176 and I-210 in the indicated proportions.

| Ex. Comp. No. | Structural formula | wt. parts |
|---|---|---|
| I-52 | $C_{11}H_{23}OC$—[benzoxazole]—[phenyl]—$OC_{11}H_{23}$ | 2 |
| I-73 | $CH_3C$—[benzoxazole]—[phenyl]—$OC_8H_{17}$ | 2 |
| I-208 | $C_6H_{13}$—[benzoxazole]—[biphenyl]—$OCC_{11}H_{23}$ | 2 |
| Composition M | | 94 |

A ferroelectric liquid crystal device was prepared in the same manner as in Example 13 except that the above liquid crystal composition P was used, and the device was subjected to measurement of optical response time and observation of a switching state, etc. In the ferroelectric liquid crystal device, a monodomain with a good and uniform alignment characteristic was observed.

The following results of the measurement are shown below.

| | 10° C. | 25° C. | 40° C. |
|---|---|---|---|
| Response time (μsec) | 633 | 327 | 178 |

As is apparent from the results in the above Examples 15–23, the ferroelectric liquid crystal devices containing the liquid crystal composition F to L and N to P showed an improved low-temperature operation characteristic, a high-speed responsiveness, and a decreased temperature dependence of the response speed.

EXAMPLE 24

A blank cell was prepared in the same manner as in Example 16 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition B prepared in Example 13. The liquid crystal device was subjected to measurement of optical response time in the same manner as in Example 13. The results are shown below.

| | 10° C. | 25° C. | 40° C. |
|---|---|---|---|
| Response time (μsec) | 720 | 353 | 193 |

EXAMPLE 25

A blank cell was prepared in the same manner as in Example 13 except for omitting the SiO₂ layer to form an alignment control layer composed of the polyimide resin layer alone on each electrode plate. A ferroelectric liquid crystal device was prepared by filling the blank cell with the liquid crystal composition B prepared in Example 13. The liquid crystal device was subjected to a measurement of optical response time in the same manner as in Example 13. The results are shown below.

| | 10° C. | 25° C. | 40° C. |
|---|---|---|---|
| Response time (μsec) | 703 | 346 | 191 |

As is apparent from the above Examples 24 and 25, also in the cases of different device structures, the devices containing the ferroelectric liquid crystal composition according to the present invention respectively provided a remarkably improved operation characteristic at a lower temperature and also a decreased temperature-dependent of the response speed similar to those in Example 16.

EXAMPLE 26

Example Compound I-245 was prepared in the following manner.

| | 10° C. | 25° C. | 40° C. |
|---|---|---|---|
| Response time (μsec) | 730 | 357 | 192 |

6-hydroxy-2-napthoic acid was altered to 6-acetoxy-2-naphthoe acid by using anhydrous acetic acid under sulfuric acid catalyst and 6-acetoxy-2-naphthoic acid chloride by using thionyl chloride. 8.16 g (32.8 m mole) of the chloride, 4.80 g (29.0 m mole) of 2-amino-4-butylphenol and 120 ml of dioxane were placed in a 300 ml three-neck flask. To the mixture, 9.6 ml of pyrridine was added dropwise with heating of 70° C. under stirring, followed by heating and stirring for 30 minutes at 80–90° C. After the reaction, the reaction mixture was poured into 600 ml of water to precipitate a crystal. The crystal was filtered and washed with water. The crystal was recrystallized from acetone to obtain 6.84 g of the 2-(6-acetoxy-2-naphthoylamine)-4-butylphenol (Yield: 62.4%).

5.40 g (14.3 m mole) of 2-(6-acetoxy-2-naphthoylamino)-4-butylphenol, 0.43 g of p-toluenesulfuric acid monohydrate and 40 ml of O-dichlorobenzene were placed in a 100 ml round-bottom flask, followed by heating and stirring for 30 minutes at 200–203° C. After the reaction, O-dichlorobenzene was distilled off under reduced pressure. To the resultant, 2.00 g (30.3 m mole) of potassium hydroxide and 60 ml of ethanol were added, followed by heating and stirring for 20 minutes at 60° C. After the reaction, the reaction mixture was poured into 600 ml of water. To the reaction mixture, 8 ml of chloric acid was added to precipitate a crystal. The crystal was filtered, washed with water and recrystallized from a mixture solvent of acetoneethanol to obtain 2.18 g of 2-(6-hydroxy-2-naphthyl)-5-butylbenzooxazole (Yield: 42.4%).

In a 30ml round-bottom flask, 0.47 g (1.48 m mole) of 2-(6-hydroxy-2-naphthyl)-5-butylbenzooxazole, 0.43 g (1.79 m mole) of octyl iodide, 0.12 g (1.82 m mole) of potassium hydroxide and 5 ml of butanol were placed, followed by refluxing for 310 minutes. The reaction mixture was poured into water, extracted from ethyl acetate to obtain an organic layer. The organic layer was washed with water dried with mirabilite and dried under reduced pressure to obtain a resultant. The resultant was recrystallized from ethylacetate to obtain a crystal. The crystal was filtered, purified by silica gel column chromatography (eluent: toluene) and recrystallized from acetone to obtain 0.36 g of 2-(6-octyloxy-2-naphthyl)-5-butylbenzooxazole (Yield: 56.6%).

Phase Transition Temperature (°C.)

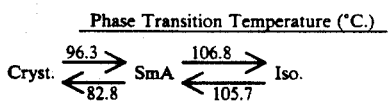

EXAMPLE 27

2-(6-octyloxy-2-naphthyl) 1-5-hexylbenzooxazole (Example Compound I-249) with the following yield was prepared in the same manner as in Example 26.

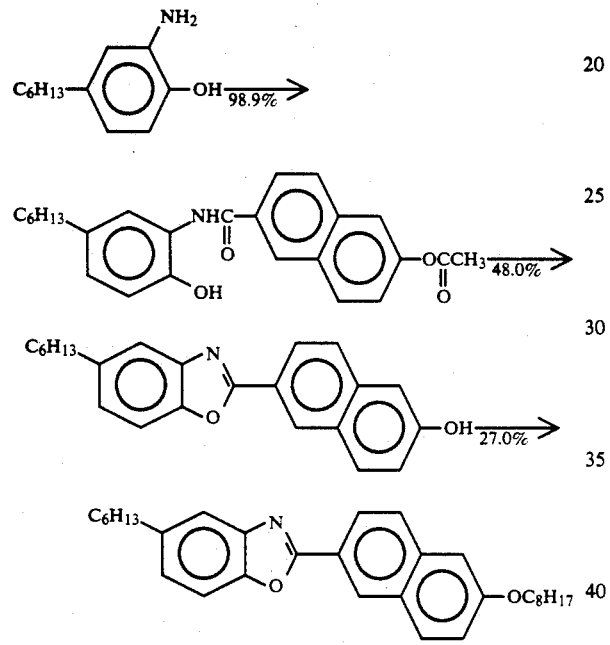

Phase Transition Temperature (°C.)

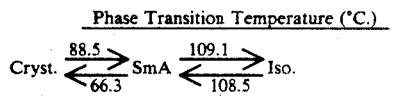

EXAMPLE 28

2-(6-decyloxy-2-naphthyl)-5-hexylbenzooxazole (Example Composition I-250) was prepared by using 2-(6-hydroxy-2-naphthyl)-5-hexylbenzooxazole synthesized in Example 26.

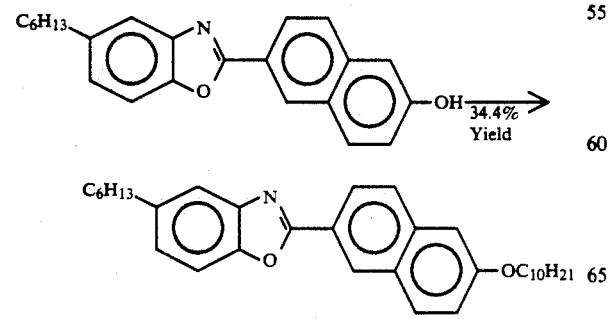

Phase Transition Temperature (°C.)

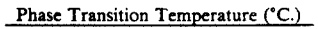

-continued

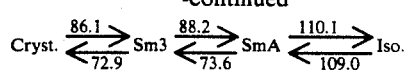

(Sm3 is a high-order smectic phase other than SmA and SmC, and is not otherwise identified).

EXAMPLE 29

2-(6-octyl-2-naphthyl)-5-hexylbenzooxazole (Example Compound I-275) was prepared by using 6-octyl-2-naphthoic acid synthesized in the following steps in the same manner as in Example 7.

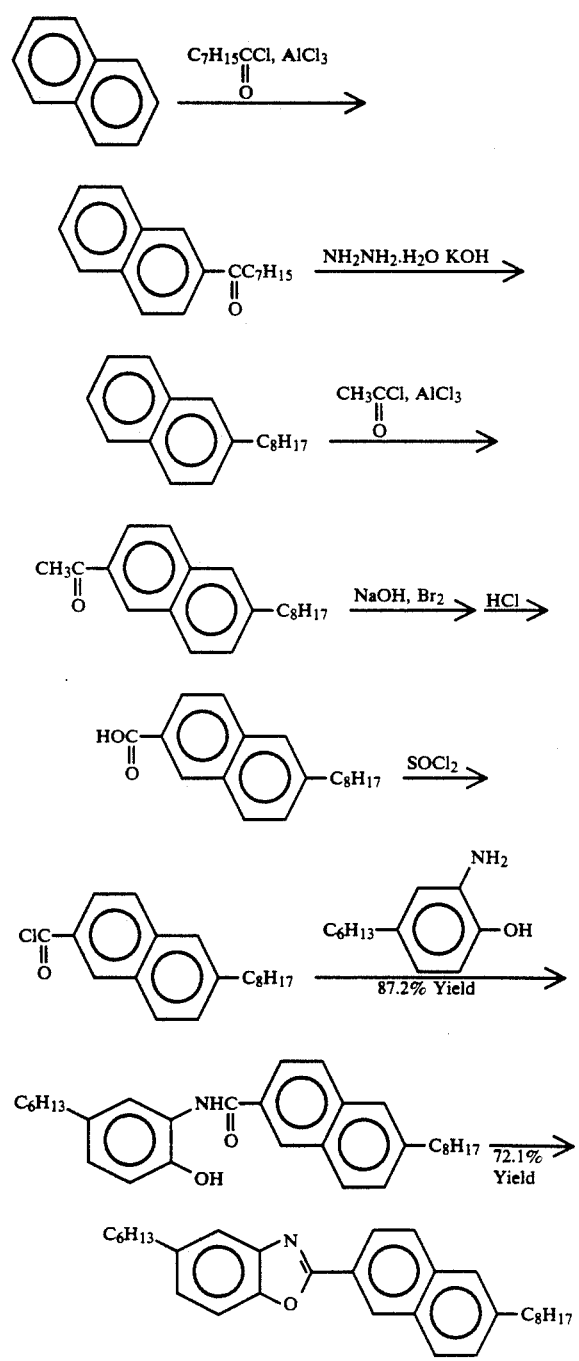

Phase Transition Temperature (°C.)

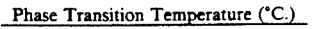

Cryst. $\underset{59.8}{\overset{71.1}{\rightleftarrows}}$ SmA $\underset{71.8}{\overset{73.4}{\rightleftarrows}}$ Iso.

EXAMPLE 30

A liquid crystal composition Q was prepared by mixing the following Example Compounds in place of Example Compounds I-5, I-18 and I-71 used in Example 15, in the indicated proportions.

| Ex. Comp. No. | Structural formula | wt. parts |
|---|---|---|
| I-190 | C$_4$H$_9$—〔benzoxazole〕—〔phenyl〕—OC$_{10}$H$_{21}$ | 2 |
| I-145 | C$_8$H$_{17}$—〔benzoxazole〕—〔phenyl〕—COC$_{10}$H$_{21}$ (C=O) | 2 |
| I-249 | C$_6$H$_{13}$—〔benzoxazole〕—〔naphthyl〕—OC$_8$H$_{17}$ | 2 |
| Composition E | | 94 |

A ferroelectric liquid crystal device was prepared in the same manner as in Example 13 except that the above liquid crystal composition Q was used, and the device was subjected to measurement of optical response time. The results of the measurement are shown below.

| | 10° C. | 25° C. | 40° C. |
|---|---|---|---|
| Response time (μsec) | 730 | 357 | 192 |

EXAMPLE 31

A liquid crystal composition R was prepared by mixing the following Example Compounds in place of Example Compounds I-79, I-154, and I-185 used in Example 18, in the indicated proportions.

| Ex. Comp. No. | Structural formula | wt. parts |
|---|---|---|
| I-250 | C$_6$H$_{13}$—〔benzoxazole〕—〔biphenyl〕—OC$_{10}$H$_{21}$ | 2 |
| I-275 | C$_6$H$_{13}$—〔benzoxazole〕—〔biphenyl〕—C$_8$H$_{17}$ | 3 |
| I-286 | C$_{10}$H$_{21}$—〔benzoxazole〕—〔phenyl〕—C$_{10}$H$_{21}$ | 3 |
| Composition I | | 92 |

A ferroelectric liquid crystal device was prepared in the same manner as in Example 13 except that the above liquid crystal composition R was used, and the device was subjected to measurement of optical response time. The results of the measurement are shown below.

| | 10° C. | 25° C. | 40° C. |
|---|---|---|---|
| Response time (μsec) | 576 | 285 | 150 |

EXAMPLE 32

A liquid crystal composition S was prepared by mixing the following Example Compounds in place of Example Compounds I-55, I-78 and I-202 used in Example 21, in the indicated proportions.

| Ex. Comp. No. | Structural formula | wt. parts |
|---|---|---|
| I-255 | C$_8$H$_{17}$—〔benzoxazole〕—〔phenyl〕—OC$_{12}$H$_{25}$ | 2 |
| I-282 | C$_8$H$_{17}$—〔benzoxazole〕—〔phenyl〕—C$_{10}$H$_{21}$ | 3 |
| I-66 | C$_6$H$_{11}$C(=O)—〔benzoxazole〕—〔phenyl〕—C$_7$H$_{15}$ | 2 |
| Composition M | | 93 |

A ferroelectric liquid crystal device was prepared in the same manner as in Example 13 except that the above liquid crystal composition S was used, and the device was subjected to measurement of optical response time and the observation of a switching state, etc. In the liquid crystal device, a monodomain with a good and uniform alignment characteristic was observed. The results of the measurement are shown below.

| | 10° C. | 25° C. | 40° C. |
|---|---|---|---|
| Response time (μsec) | 618 | 319 | 177 |

As is apparent from the results in the above Examples 30 to 32, the ferroelectric liquid crystal devices containing the liquid crystal compositions Q to S showed an improved low-temperature operation, a high-speed responsiveness, and a decreased temperature dependence of the response speed.

EFFECTS OF THE INVENTION

A mesomorphic compound of the present invention is effectively applicable to a device making use of ferroelectricity in the case that the mesomorphic compound itself shows a chiral smectic phase. A device containing a liquid crystal composition comprising the mesomorphic compound of the present invention is capable of operating by making use of the ferroelectricity the composition shows, in the case that the composition shows a chiral smectic phase.

A ferroelectric liquid crystal device thus used has a good switching characteristic, an improved low-temperature operation characteristic and a decreased temperature dependence of the response speed.

Further, the liquid crystal device of the present invention can be used as a display device and combined with a light source and a driving circuit, etc., to provide a good display apparatus.

What is claimed is:

1. A mesomorphic compound represented by the following Formula [I]:

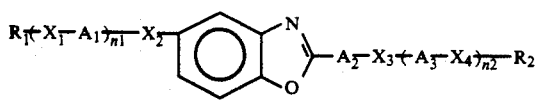

wherein $R_1$ and $R_2$ independently denote an alkyl group having 1-16 carbon atoms capable of having a substituent; $X_1$, $X_2$, $X_3$ and $X_4$ independently denote a single bond,

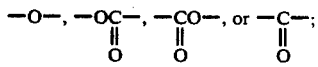

$A_1$, $A_2$ and $A_3$ independently denote

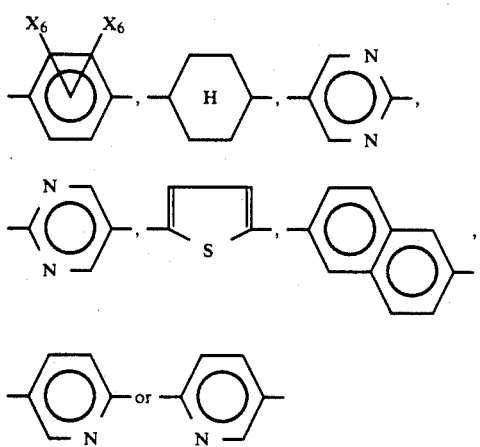

; $X_5$ and $X_6$ denote hydrogen atom, fluorine, chlorine, bromine, $CH_3$, $CN$ or $CF_3$; $n_1$ and $n_2$ are 0 or 1, with provisos that (1) $X_2$ cannot be a single bond when n is 1, (2) $X_3$ cannot be a single bond when $n_2$ is 1 and (3) at least one of $X_2$ and $X_3$ denotes

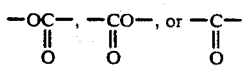

when both $n_1$ and $n_2$ are 0 and $Z_2$ denote

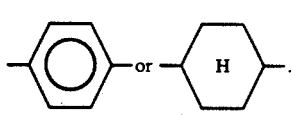

2. A mesomorphic compound according to claim 1, which is represented by any one of the following Formulae [Ia]-[Ik]:

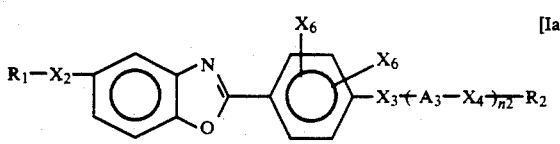

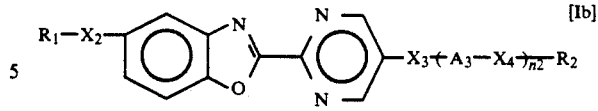

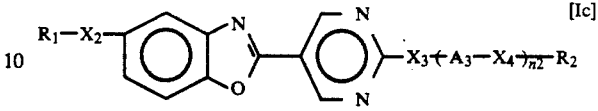

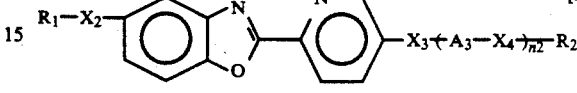

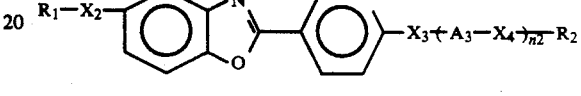

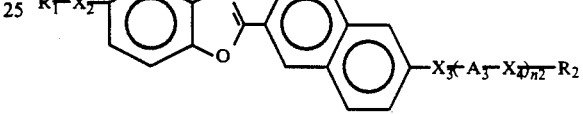

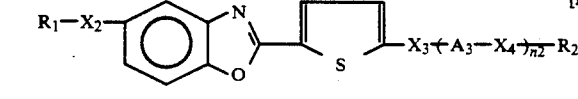

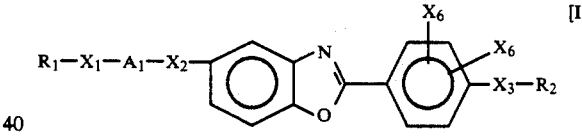

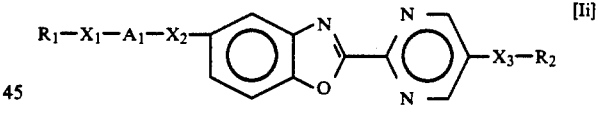

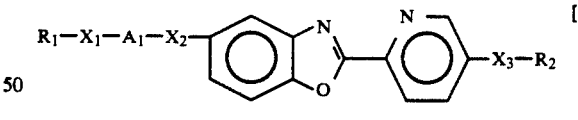

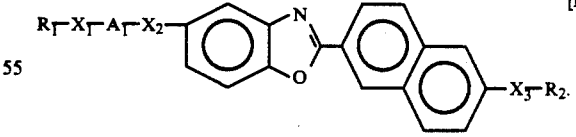

wherein $R_1$ and $R_2$ denote an alkyl group having 1-16 carbon atoms capable of having a substituent; $X_1$, $X_2$, $X_3$ and $X_4$ denote a single bond,

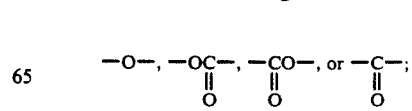

$A_1$ and $A_3$ denote $X_5$ and $X_6$ denote hydrogen, fluorine, chlorine, bromine, $CH_3$, CN or $CF_3$; $n_2$ or 0 or 1, with provisos that (1) $X_2$ cannot be a single bond when $-X_1-A_1-$ exists, (2) $X_3$ cannot be a single bond when $n_2$ is 1 and (3) at least one of $X_2$ and $X_3$ denotes $$-OC-, -CO-, \text{ or } -C- \\ \phantom{-OC}\| \phantom{,-} \| \phantom{CO, or } \| \\ \phantom{-OC}O \phantom{,-} O \phantom{CO, or } O$$

when $n_2$ is 0 and both $X_5$ and $X_6$ denote hydrogen in the formula [Ia].

3. A mesomorphic compound according to claim 2, which is represented by any one of the following Formulae [Iaa]-[Ihb]:

wherein $R_1$ and $R_2$ denote an alkyl group having 1-16 carbon atoms capable of having a substituent; $X_2$, $X_3$, and $X_4$ denote a single bond, $$-O-, -OC-, -CO-, \text{ or } -C-;\\ \phantom{-O-,-} \| \phantom{,-} \| \phantom{CO, or } \| \\ \phantom{-O-,-} O \phantom{,-} O \phantom{CO, or } O$$

$X_5$ and $X_6$ denote hydrogen, fluorine, chlorine, bromine, $CH_3$, CN or $CF_3$; $n_1$ and $n_2$ are 0 or 1, with provisos that (1) $X_2$ cannot be a single bond in the Formulae [Iha] and [Ihb], (2) $X_3$ cannot be a single bond in Formulae [Iab] and [Iac] and (3); at least one of $X_2$ and $X_3$ denotes $$-OC-, -CO-, \text{ or } -C- \\ \phantom{-OC}\| \phantom{,-} \| \phantom{CO, or } \| \\ \phantom{-OC}O \phantom{,-} O \phantom{CO, or } O$$

when both $X_5$ and $X_6$ denote hydrogen.

4. A mesomorphic compounds according to claim 3, wherein $R_1$ and $R_2$ denote any one of the following groups (i)-(iv):

(i) an n-alkyl group having 1-16 carbon atoms;

$$\text{(ii)} \quad \begin{array}{c} CH_3 \\ | \\ +CH_2\!\!+_{\overline{m}}CH-C_nH_{2n+1} \end{array}$$

wherein m is an integer of 0-6 and n is an integer of 1-8;

$$\text{(iii)} \quad \begin{array}{c} CH_3 \\ | \\ +CH_2\!\!+_{\overline{r}}CH+CH_2\!\!+_{\overline{s}}OC_tH_{2t+1} \end{array}$$

wherein r is an integer of 0-6, s is 0 or 1 and t is an integer of 1-12;

$$+CH_2)_{\overline{m}*}^{F}CH-C_xH_{2x+1} \quad (iv)$$

wherein m is 0 or 1 and x is integer of 4-14.

5. A mesomorphic compound according to claim 3, wherein $X_5$ and $X_6$ denote hydrogen, fluorine or $CF_3$.

6. A mesomorphic compound according to claim 4, wherein $X_5$ and $X_6$ denote hydrogen, fluorine or $CF_3$.

7. A liquid crystal composition comprising 1-80% by weight of the mesomorphic compound of any of claims 1-6 and a second mesomorphic compound.

8. A liquid crystal composition according to claim 7, which comprises 1-60% by weight of the mesomorphic compound.

9. A liquid crystal composition according to claim 8, which comprises 1-40% by weight of the mesomorphic compound.

10. A liquid crystal composition according to claim 7, wherein the second mesomorphic compound is selected from the group consisting of the following Formulae (II) to (X):

$$-\overset{\|}{\underset{O}{C}}O-,\ -O\overset{\|}{\underset{O}{C}}-,\ -O-\ \text{or}\ -O\overset{\|}{\underset{O}{C}}O-;$$

and $X_3'$, $X_4'$ and $X_5'$ denote a single bond, $$-\overset{\|}{\underset{O}{C}}O-,\ -O\overset{\|}{\underset{O}{C}}-,\ -CH_2O-\ \text{or}\ -OCH_2-;$$

(IV) $R_1'-X_1'-\underset{Y_1'}{\bigcirc}-X_3'-\underset{Y_2'}{\bigcirc}-X_4'-\underset{Y_3'}{\{\bigcirc\}}_j-X_2'-R_2$ wherein j denotes 0 or 1; $Y_1'$, $Y_2'$ and $Y_3'$ denote H, halogen, $CH_3$ or $CF_3$; $X_1'$ and $X_2'$ denote a single bond, $$-\overset{\|}{\underset{O}{C}}O-,\ -O\overset{\|}{\underset{O}{C}}-,\ -O-\ \text{and}\ -O\overset{\|}{\underset{O}{C}}O-;$$

and $X_3'$ and $X_4'$ denote a single bond, (II) $R_1'-X_1'-\underset{N}{\overset{N}{\bigcirc}}-X_3'-\bigcirc-X_4'-\{\overset{Y}{\bigcirc}\}_e\{H\}_f-X_2'-R_2'$ $$-\overset{\|}{\underset{O}{C}}O-,\ -O\overset{\|}{\underset{O}{C}}-,\ -CH_2O-,\ -OCH_2-,\ -CH_2CH_2-,\ -\overset{\|}{\underset{O}{C}}S-,\ -S\overset{\|}{\underset{O}{C}}-,$$

$$+CH_2)_{\overline{2}}\overset{\|}{\underset{O}{C}}S-,\ +CH_2)\overset{\|}{\underset{O}{C}}O-,\ -CH=CHCO-\ \text{or}\ -O-;$$

(V) $R_1'-X_1'-\{\bigcirc\}_k\{H\}_l\{H\}-X_3'-\{\bigcirc\}_m-X_4'-\bigcirc-X_2'-R_2'$ wherein e denotes 0 or 1 and f denotes 0 or 1 with proviso that e+f=0 or 1; Y' denotes H, halogen, $CH_3$ or $CF_3$; $X_1'$ and $X_2'$ denote a single bond, wherein k, l and m denote 0 or 1 with the proviso that k+l+m=0, 1 or 2; $X_1'$ and $X_2'$ denote a single bond, $$-\overset{\|}{\underset{O}{C}}O-,\ -O\overset{\|}{\underset{O}{C}}-,\ -O-\ \text{or}\ -O\overset{\|}{\underset{O}{C}}O-;$$

and $X_3'$ and $X_4'$ denote a single bond, and $X_3'$ and $X_4'$ denote a single bond, $$-\overset{\|}{\underset{O}{C}}O-,\ -O\overset{\|}{\underset{O}{C}}-,\ -OCH_2-\ \text{or}\ -CH_2O-;$$

(III) $R_1'-X_1'-\{\bigcirc\}_g\{H\}_h-X_3'-\underset{N}{\overset{N}{\bigcirc}}-N_4'-\bigcirc-X_5'-\{\bigcirc\}_i-X_2'-R_2'$ wherein g and h denote 0 or 1 with the proviso that g+h=1; i denotes 0 or 1; $X_1'$ and $X_2'$ denote a single bond, $$-\overset{\|}{\underset{O}{C}}O-,\ -O\overset{\|}{\underset{O}{C}}-,\ -CH_2O-\ \text{or}\ -OCH_2-;$$

-continued

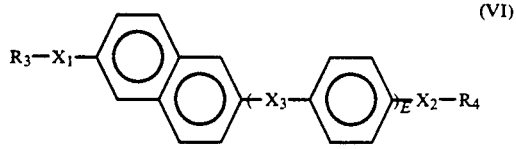 (VI)

wherein E denotes 0 or 1; $X_1'$ and $X_2'$ denote a single bond,

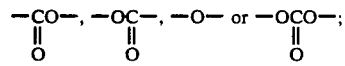

and $X_3'$ denote a single bond,

—CO—, —OC—, —CH$_2$O— or —OCH$_2$—;
  ‖          ‖
  O          O

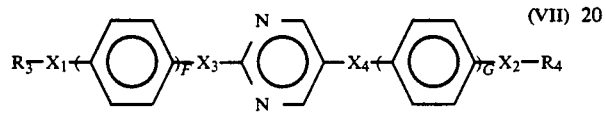 (VII)

wherein F and G denote 0 or 1; $X_1'$ and $X_2'$ denote a single bond,

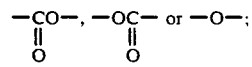

and $X_3'$ and $X_4'$ denote a single bond,

—CO—, —OC—, —CH$_2$O— or —OCH$_2$—;
  ‖          ‖
  O          O

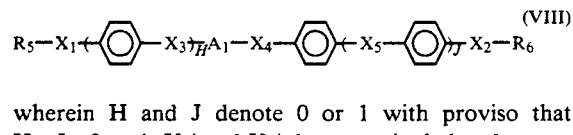 (VIII)

wherein H and J denote 0 or 1 with proviso that H+J=0 or 1; $X_1'$ and $X_2'$ denote a single bond,

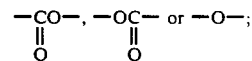

$A_1'$ denotes

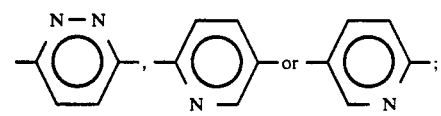

and $X_3'$ and $X_4'$ denote a single bond,

—CO—, —OC—, CH$_2$O— or —OCH$_2$—;
  ‖          ‖
  O          O

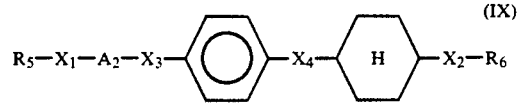 (IX)

wherein $X_1'$ and $X_2'$ denote a single bond,

—CO—, —OC— or —O—;
  ‖          ‖
  O          O $A_2'$ denotes

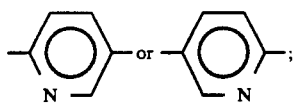

and $X_3'$ and $X_4'$ denote a single bond,

—CO—, —OC—, —CH$_2$O— or —OCH$_2$—;
  ‖          ‖
  O          O

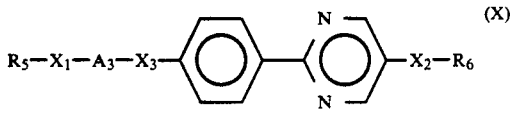 (X)

wherein $X_1'$ and $X_2'$ denote a single bond,

—CO—, —OC— or —O—;
  ‖          ‖
  O          O $A_2'$ denotes

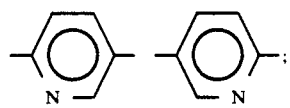

and $X_3'$ denote a single bond,

—CO—, —OC—, CH$_2$O— or —OCH$_2$—;
  ‖          ‖
  O          O wherein $R_1'$, $R_2'$, $R_3'$ and $R_4'$ independently denote a linear or branched alkyl group having 1-18 carbon atoms capable of including one or two or more non-neighboring methylene groups which can be replaced with —CHX— (wherein X is halogen) and capable of further including one or two or more non-neighboring methylene groups other than those directly connected to $X_1'$ or $X_2'$ which can be replaced with at least one species of

—O—, —C—, —OC—, —CO—,
      ‖     ‖     ‖
      O     O     O

CN         CN
   |          |
—CH—  and  —CCH$_3$—, with the proviso that $R_1'$, $R_2'$, $R_3'$ and $R_4'$ do not connect to a ring structure when $R_1'$, $R_2'$, $R_3'$ and $R_4'$ denote a halogenated alkyl group containing one methylene group replaced with —CHX— (wherein X is halogen);

$R_5'$ and $R_6'$ denote a linear or branched alkyl group having 1-18 carbon atoms capable of including one or two or more non-neighboring methylene groups other than those directly connected to $X_1'$ or $X_2'$ which can be replaced with at least one species of
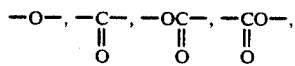
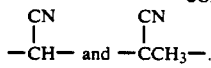
11. A liquid crystal composition according to claim 8, wherein the second mesomorphic compound is selected from the group consisting of the following Formulae (II a-d), (III a-c), (IV a, b), V a-f), (VI a, b), (VII a, b), (VIII a-c), (IX a, b), (X a-g):
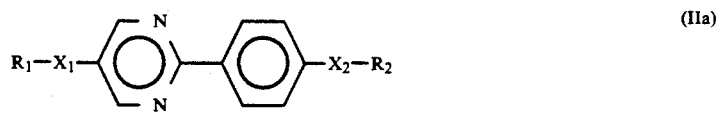
(IIa)
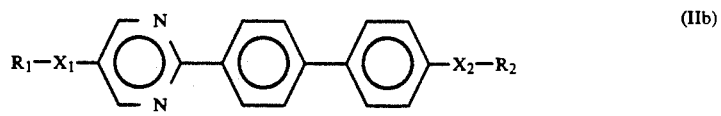
(IIb)
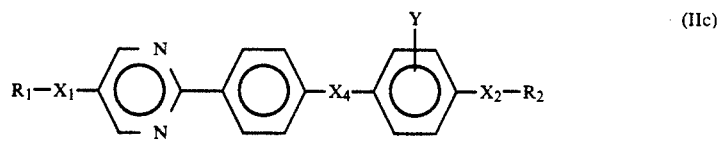
(IIc)
(IId)
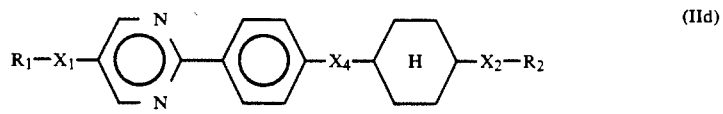
(IIIa)
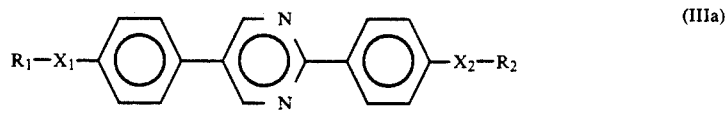
(IIIb)
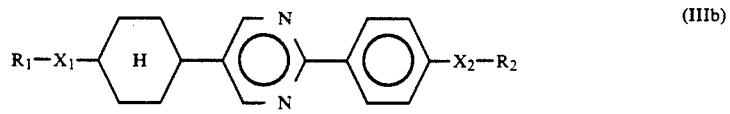
(IIIc)
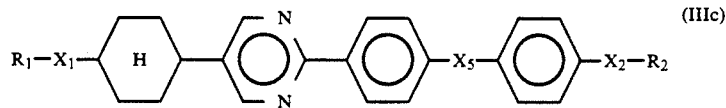
(IVa)
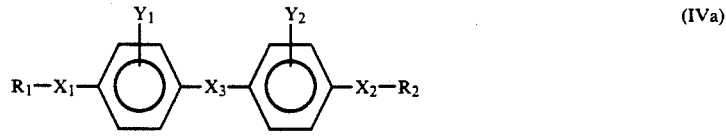
(IVb)
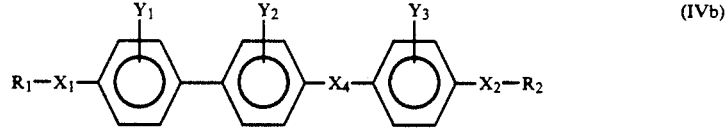
(Va)
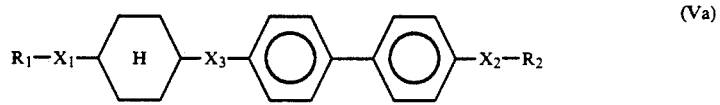
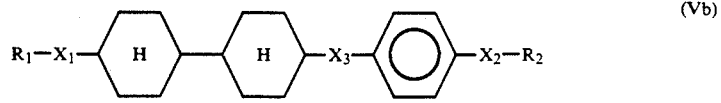
(Vb)

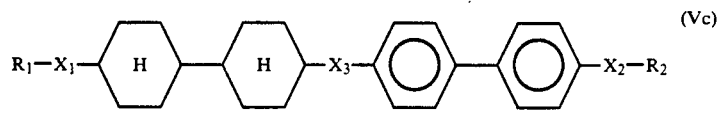
(Vc)
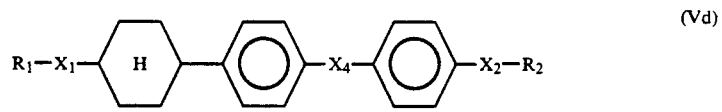
(Vd)
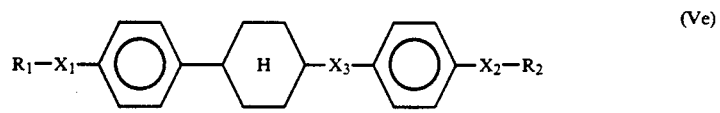
(Ve)
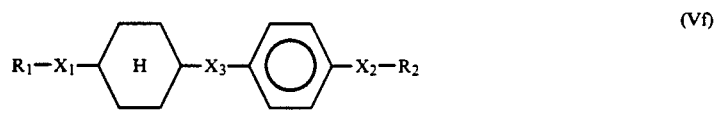
(Vf)
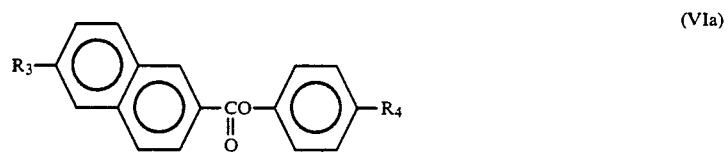
(VIa)
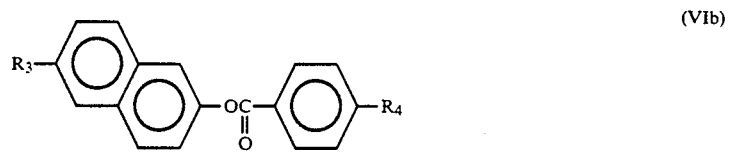
(VIb)
(VIIa)
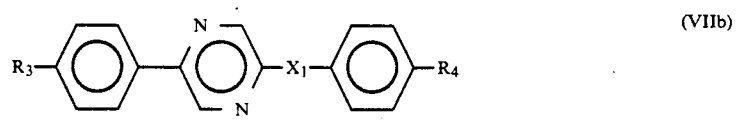
(VIIb)
(VIIIa)
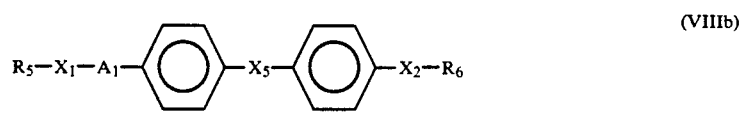
(VIIIb)
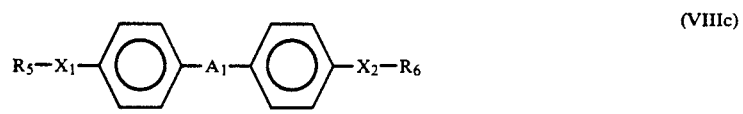
(VIIIc)
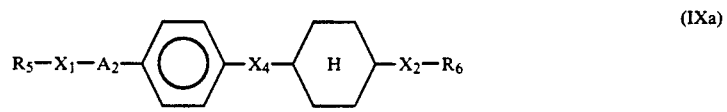
(IXa)
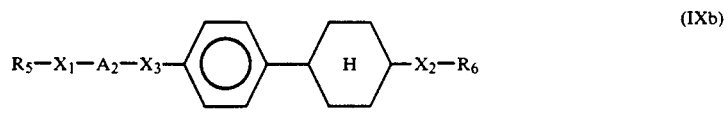
(IXb)

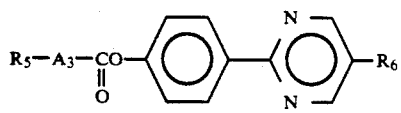 (Xa)

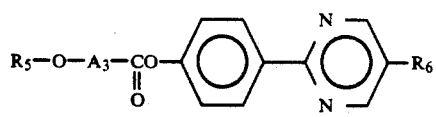 (Xb)

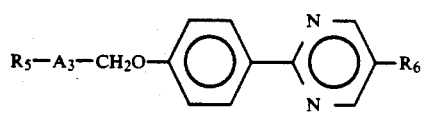 (Xc)

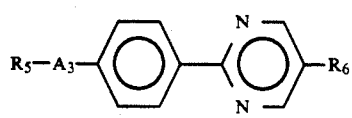 (Xd)

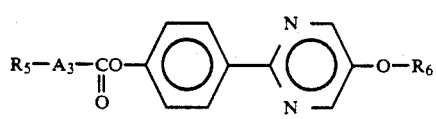 (Xe)

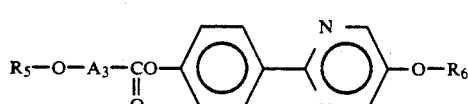 (Xf)

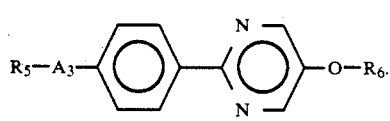 (Xg)

wherein $X_1'$ and $X_2'$ denote a single bond,

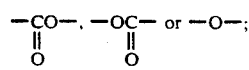

$X_3'$, $X_4'$ and $X_5'$ denote a single bond,

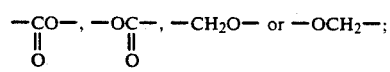

$Y'$, $Y_1'$, $Y_2'$ and $Y_3'$ denote H, halogen $CH_3$ or $CF_3$; $A_1'$, $A_2'$ and $A_3'$ denote

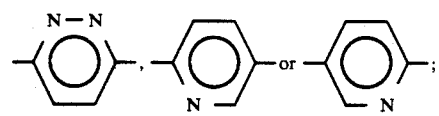

$R_1$ and $R_2'$ denote a linear or branched alkyl group having 1–18 carbon atoms capable of including one or two or more non-neighboring methylene groups which can be replaced with —CHX— (wherein X is a halogen) and capable of further including one or two mor more non-neighboring methylene groups other than those directly connected to $X_1'$ or $X_2'$ which can be replaced with at least one species of

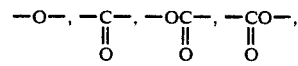

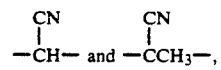

with proviso that $R_1'$ and $R_2'$ do not connect to a ring structure when $R_1'$ and $R_2'$ denote a halogenated alkyl group containing one methylene group replaced with —CHX— (wherein X is halogen); $R_3'$ and $R_4'$ denote a linear or branched alkyl group having 1–18 carbon atoms capable of including one or two or more non-neighboring methylene groups which can be replaced with —CHX— (wherein X is halogen) and capable of further including one or two or more non-neighboring methylene groups which can be replaced with at least one species of

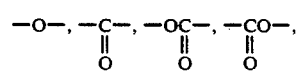

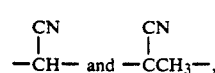

with proviso that $R_3$ and $R_4'$ do not connect to a ring structure when $R_3'$ and $R_4'$ denote a halogenated alkyl group containing one methylene group replaced with —CHX— (wherein X is halogen); $R_5'$ and $R_6'$ denote a linear or branched alkyl group having 1-18 carbon atoms capable of including one or two or more non-neighboring methylene groups other than those directly connected to $X_1'$, $X_2'$ or O which can be replaced with at least one species of

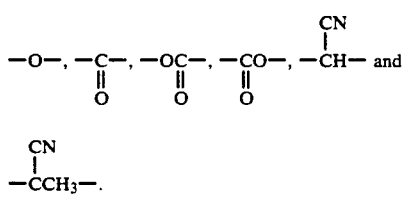

12. A liquid crystal composition according to claim 9, wherein the second mesomorphic compound is selected from the group consisting of the following formulae (II aa-dc), (III aa-cb), (IV aa-bf), (Vaa-fa), (VII aa-bb), (VIII aa-cc), (IX aa-bb):

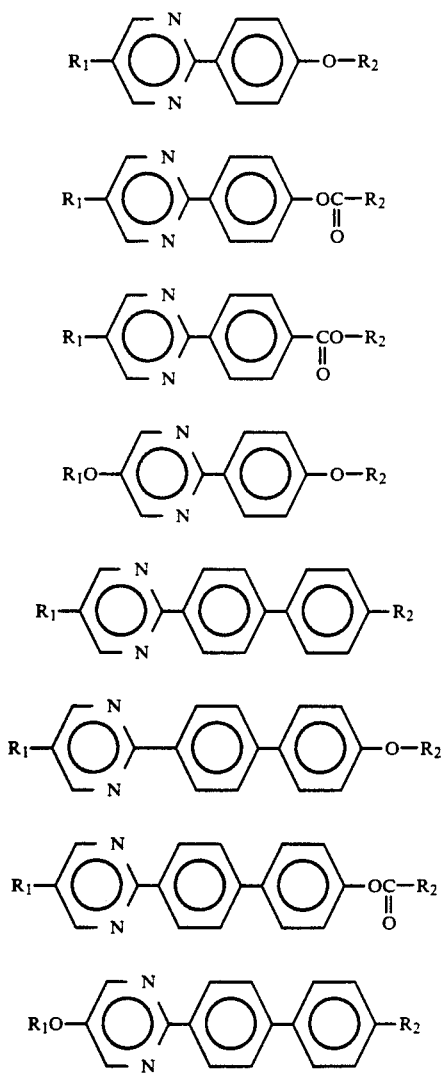

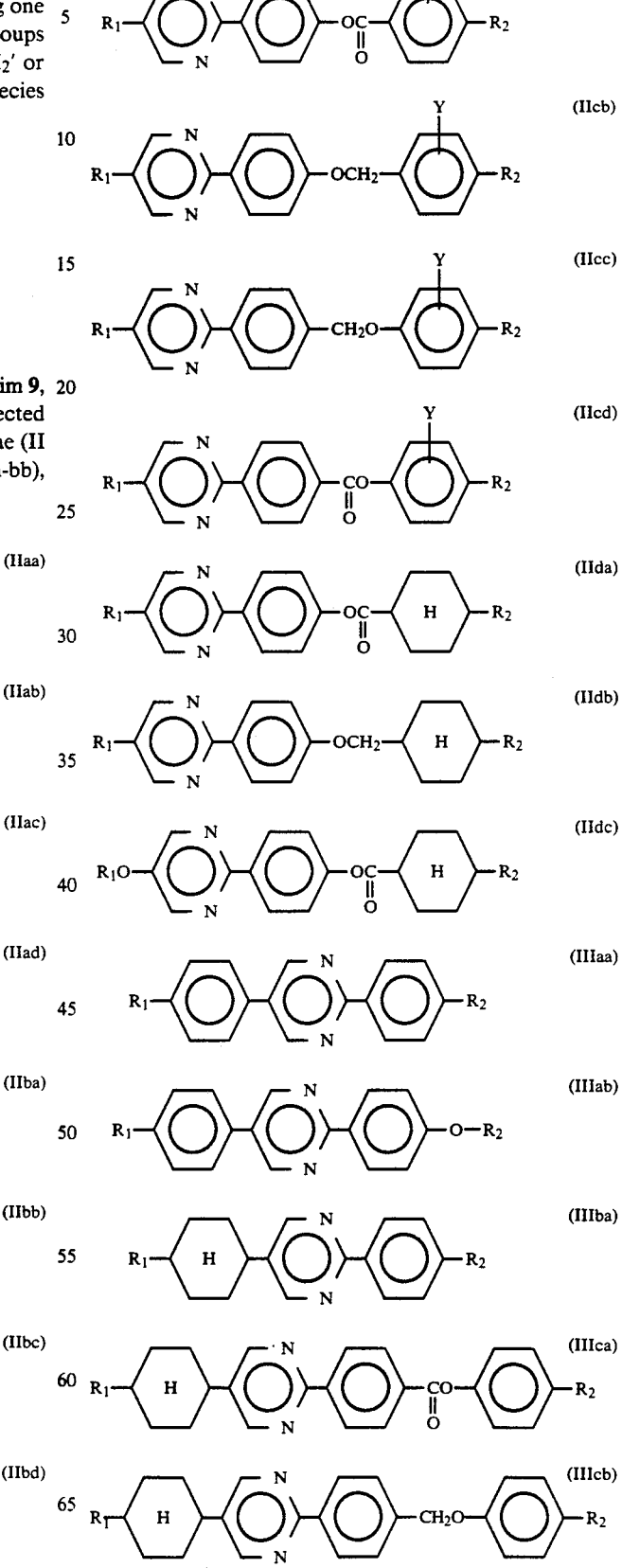

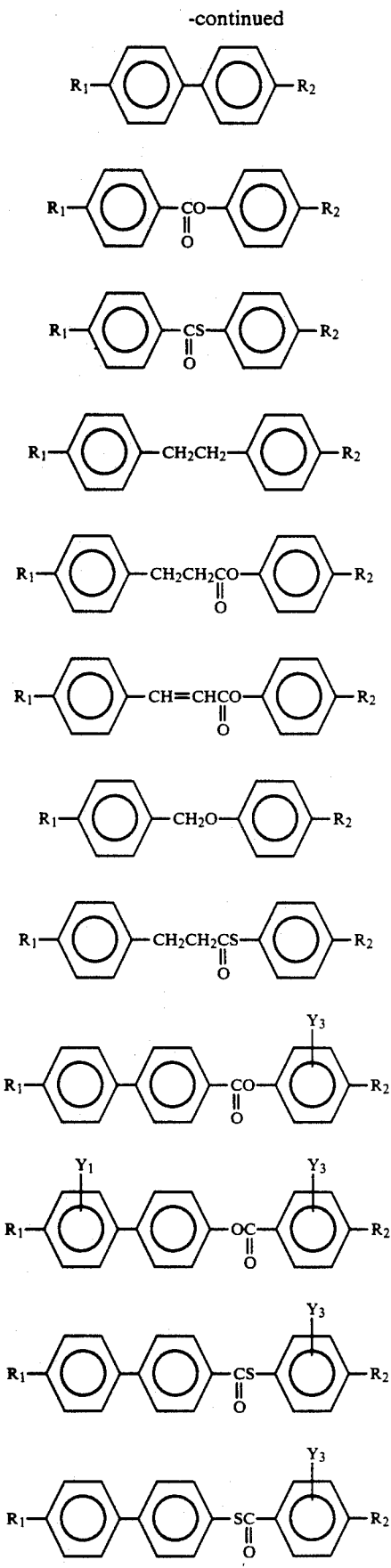
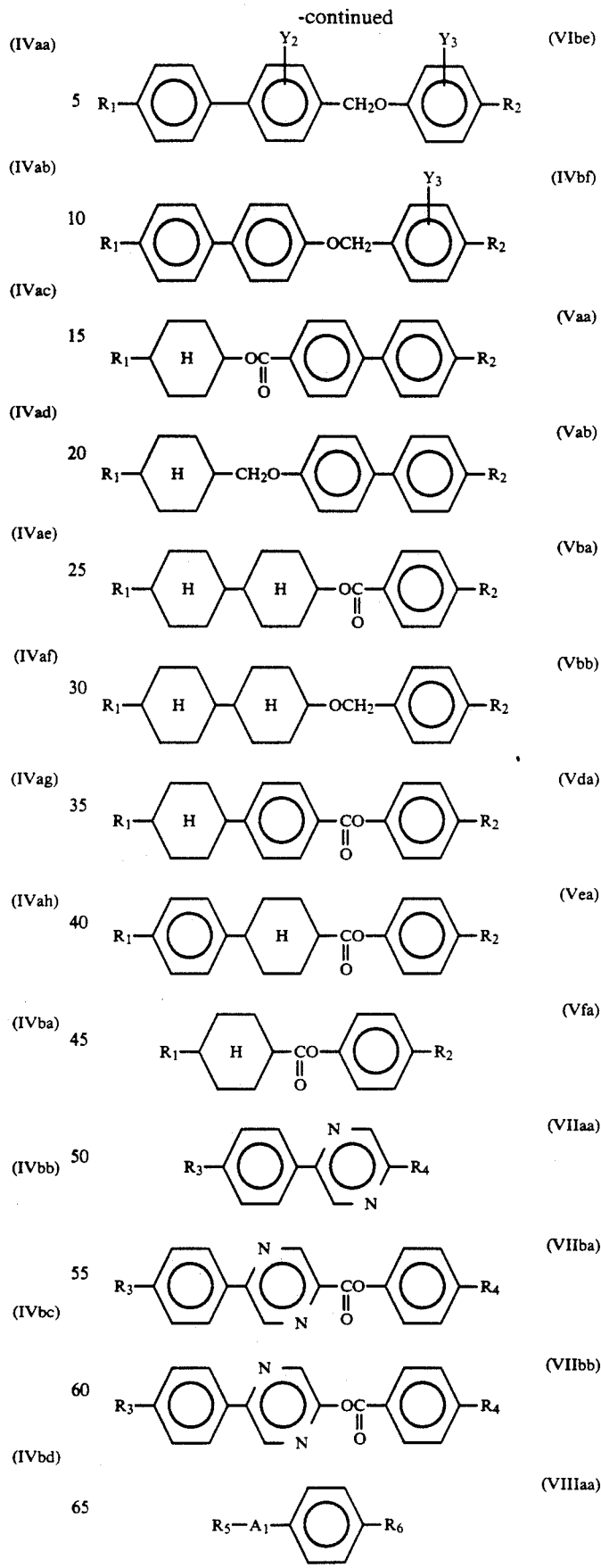

-continued

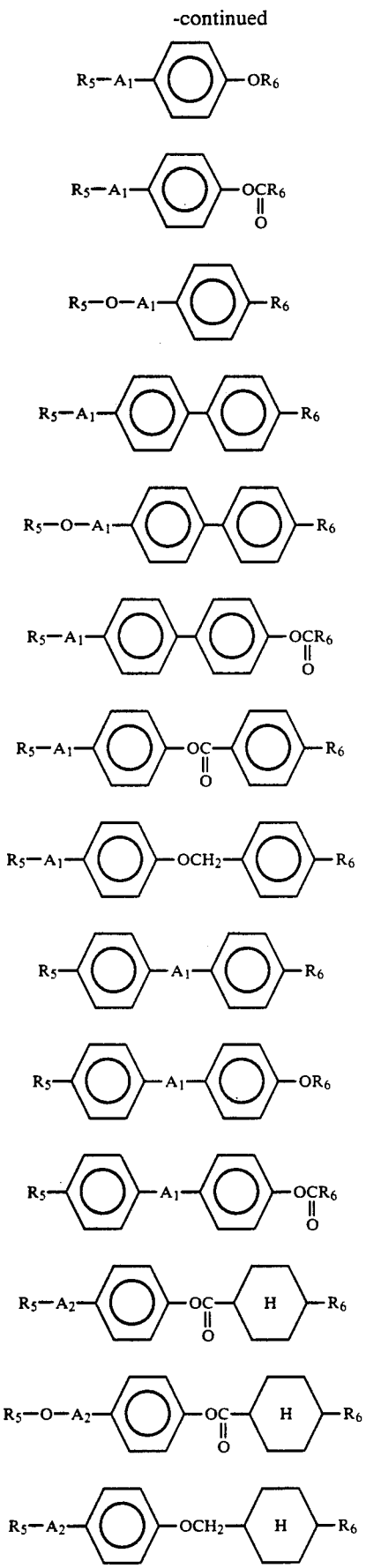

-continued

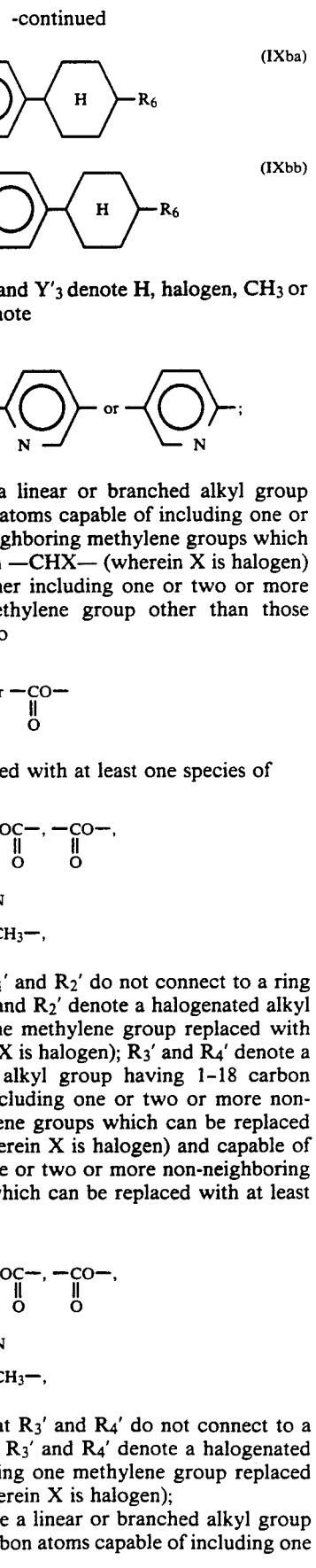

wherein Y', R'$_1$, Y'$_2$ and Y'$_3$ denote H, halogen, CH$_3$ or CF$_3$; A', and A'$_2$ denote $$-\underset{}{\bigcirc}-,\ -\underset{N}{\overset{N-N}{\bigcirc}}-,\ \text{or}\ -\underset{N}{\bigcirc}-;$$

R'$_1$ and R$_2$ denote a linear or branched alkyl group having 1-18 carbon atoms capable of including one or two or more non-neighboring methylene groups which can be replaced with —CHX— (wherein X is halogen) and capable of further including one or two or more non-neighboring methylene group other than those directly connected to $$-\text{O}-,\ -\underset{\text{O}}{\overset{}{\text{OC}}}-\ \text{or}\ -\underset{\text{O}}{\overset{}{\text{CO}}}-$$

which can be replaced with at least one species of $$-\text{O}-,\ -\underset{\text{O}}{\overset{}{\text{C}}}-,\ -\underset{\text{O}}{\overset{}{\text{OC}}}-,\ -\underset{\text{O}}{\overset{}{\text{CO}}}-,$$

$$-\underset{}{\overset{\text{CN}}{\text{CH}}}-\ \text{and}\ -\underset{}{\overset{\text{CN}}{\text{CCH}_3}}-,$$

with proviso that R$_1$' and R$_2$' do not connect to a ring structure when R$_1$' and R$_2$' denote a halogenated alkyl group containing one methylene group replaced with —CHX— (wherein X is halogen); R$_3$' and R$_4$' denote a linear or branched alkyl group having 1-18 carbon atoms capable of including one or two or more non-neighboring methylene groups which can be replaced with —CHX— (wherein X is halogen) and capable of further including one or two or more non-neighboring methylene groups which can be replaced with at least one species of $$-\text{O}-,\ -\underset{\text{O}}{\overset{}{\text{C}}}-,\ -\underset{\text{O}}{\overset{}{\text{OC}}}-,\ -\underset{\text{O}}{\overset{}{\text{CO}}}-,$$

$$-\underset{}{\overset{\text{CN}}{\text{CH}}}-\ \text{and}\ -\underset{}{\overset{\text{CN}}{\text{CCH}_3}}-,$$

with the proviso that R$_3$' and R$_4$' do not connect to a ring structure when R$_3$' and R$_4$' denote a halogenated alkyl group containing one methylene group replaced with —CHX— (wherein X is halogen);

R$_5$' and R$_6$' denote a linear or branched alkyl group having 1-18 carbon atoms capable of including one or two or more non-neighboring methylene groups other than those directly connected to

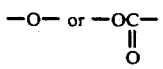

which can be replaced with at least one species of

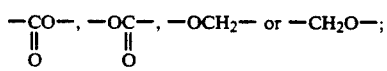

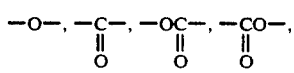

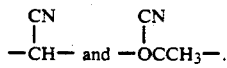

13. A cell comprising a pair of base plates having opposed electrodes and a mesomorphic compound of claims 1-6 disposed therebetween.

14. A display device comprising the cell of claim 13, and an alignment control layer.

15. A display apparatus comprising a device of claim 14, and a circuit for driving a liquid crystal.

16. A cell comprising a pair of base plates having opposed electrodes and a liquid crystal composition of claim 7.

17. A cell according to claim 16, wherein the composition comprises 1-60% by weight of the mesomorphic compound.

18. A cell according to claim 17, wherein the composition comprises 1-40% by weight of the mesomorphic compound.

19. A cell according to claim 16, wherein the second mesomorphic compound is selected from the group consisting of the following Formulae (II) to (X):

wherein e denotes 0 or 1 and f denotes 0 or 1 with proviso that e+f=0 or 1; Y' denotes H, halogen, CH₃ or CF₃; X₁' and X₂' denote a single bond,

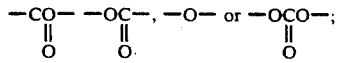

and X₃' and X₄' denote a single bond,

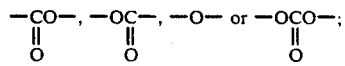  (III)

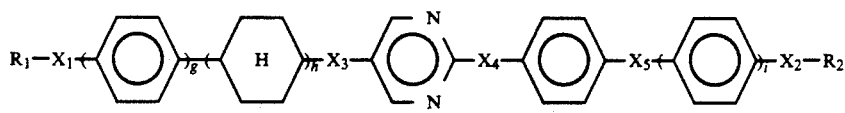

wherein g and h denote 0 or 1 with the proviso that g+h=1; i denotes 0 or 1; X₁' and X₂' denote a single bond,

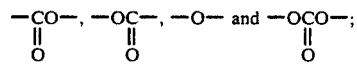

and X₃', X₄' and X₅' denote a single bond,

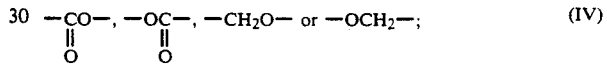  (IV)

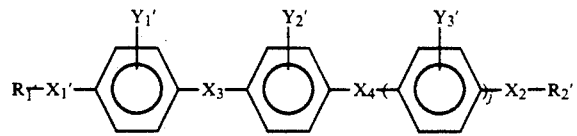

wherein j denotes 0 or 1; Y₁', Y₂' and Y₃' denote h, halogen, CH₃ or CF₃; X₁' and X₂' denote a single bond,

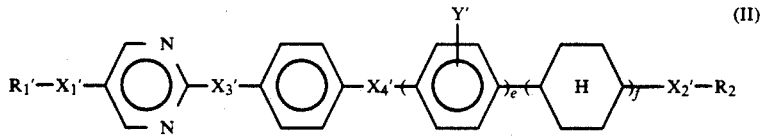

(II)

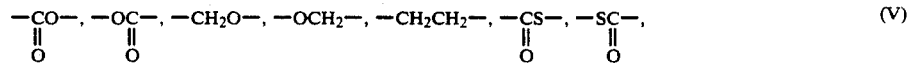

and X₃' and X₄' denote a single bond,

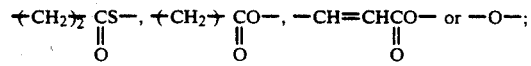  (V)

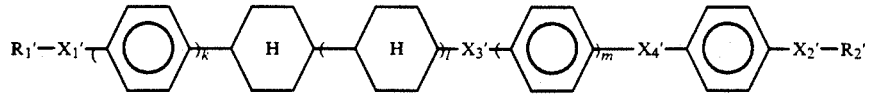

wherein k, l and m denote 0 or 1 with the proviso that k+l+m=0, 1 or 2; $X_1'$ and $X_2'$ denote a single bond,

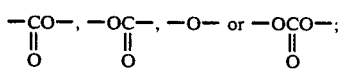

and $X_3'$ and $X_4'$ denote a single bond,

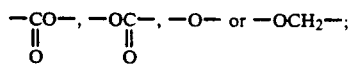 (VI)

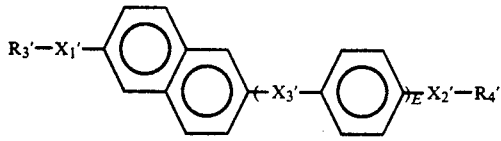

wherein E denotes 0 or 1; $X_1'$ and $X_2'$ denote a single bond,

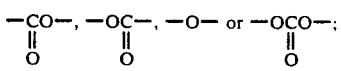

and $X_3'$ denote a single bond,

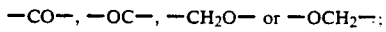 (VII)

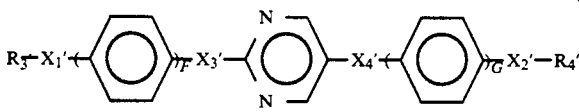

wherein F and G denote 0 or 1; $X_1'$ and $X_2'$ denote a single bond,

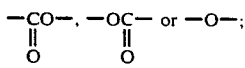

and $X_3'$ and $X_4'$ denote a single bond,

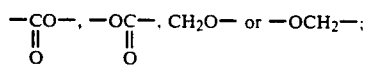

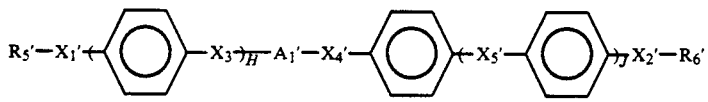

wherein H and J denote 0 or 1 with proviso that H+J=0 or 1; $X_1'$ and $X_2'$ denote a single bond,

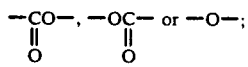

$A_1'$ denotes

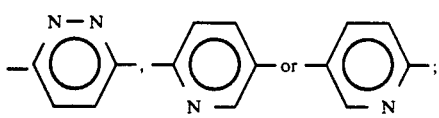

and $X_3'$ and $X_4'$ denote a single bond,

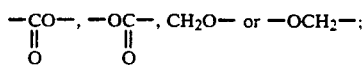 (IX)

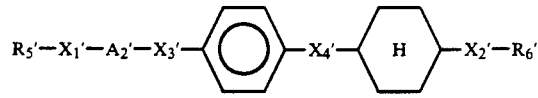

wherein $X_1'$ and $X_2'$ denote a single bond

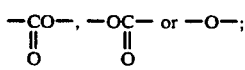

$A_2'$ denotes

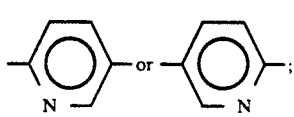

and $X_3'$ and $X_4'$ denote a single bond,

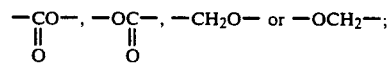 (X)

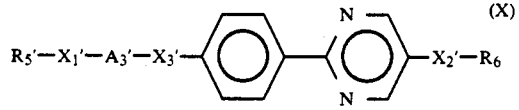 (X)

wherein $X_1'$ and $X_2'$ denote a single bond,

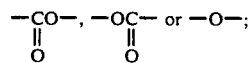

$A_2'$ denotes (VIII)

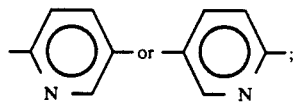

and $X_3'$ denote a single bond,

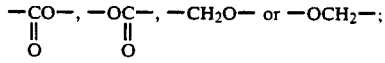

wherein $R_1'$, $R_2'$, $R_3'$ and $R_4'$ denote a linear or branched alkyl group having 1-18 carbon atoms capable of including one or two or more non-neighboring methylene groups which can be replaced with —CHX— (wherein X is halogen) and capable of further including one or two or more non-neighboring methylene groups other than those directly connected to $X_1'$ or $X_2'$ which can be replaced with at least one species of

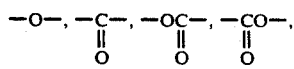
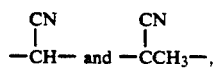

with the proviso that $R_1'$, $R_2'$, $R_3'$ and $R_4'$ do not connect to a ring structure when $R_1'$, $R_2'$, $R_3'$ and $R_4'$ denote a halogenated alkyl group containing one methylene group replaced with —CHX— (wherein X is halogen);

$R_5'$ and $R_6'$ denote a linear or branched alkyl group having 1-18 carbon atoms capable of including one or two or more non-neighboring methylene groups other than those directly connected to $X_1'$ and $X_2'$ which can be replaced with at least one species of

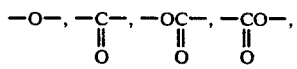

20. A cell according to claim 17, wherein the second mesomorphic compound is selected from the group consisting of the following Formulae (II a-d), (III a-c), (IV a, b), (V a-f), (VI a, b), (VII a, b), (VII a-c), (IX a, b), (X a-g):

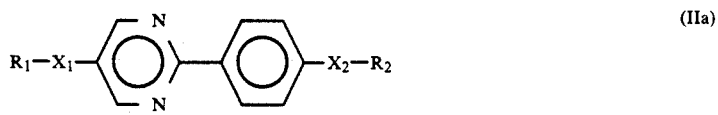
(IIa)

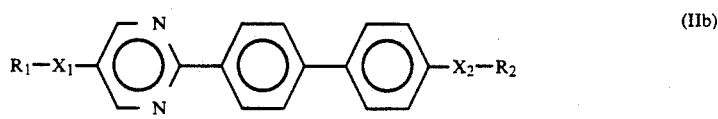
(IIb)

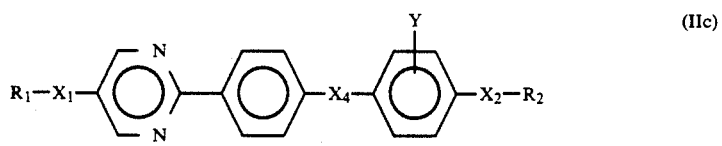
(IIc)

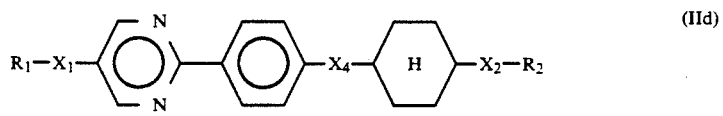
(IId)

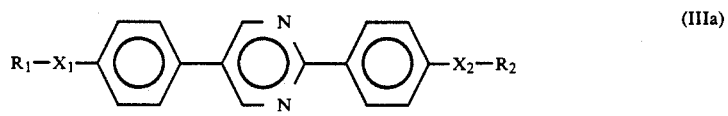
(IIIa)

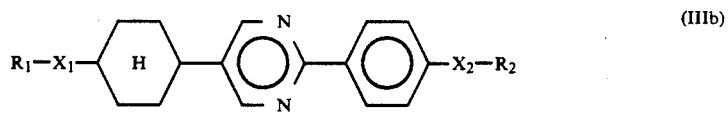
(IIIb)

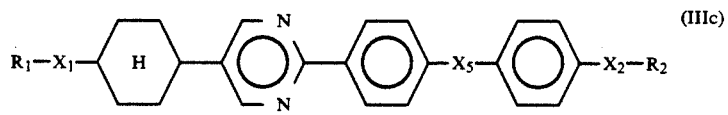
(IIIc)

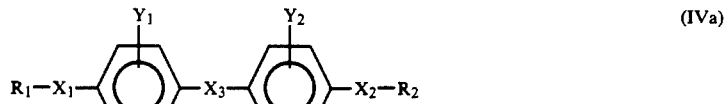
(IVa)

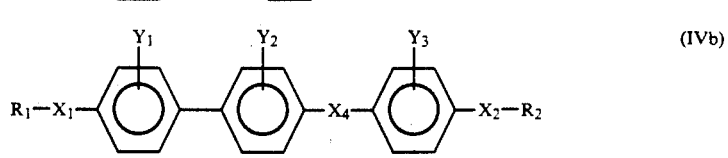
(IVb)

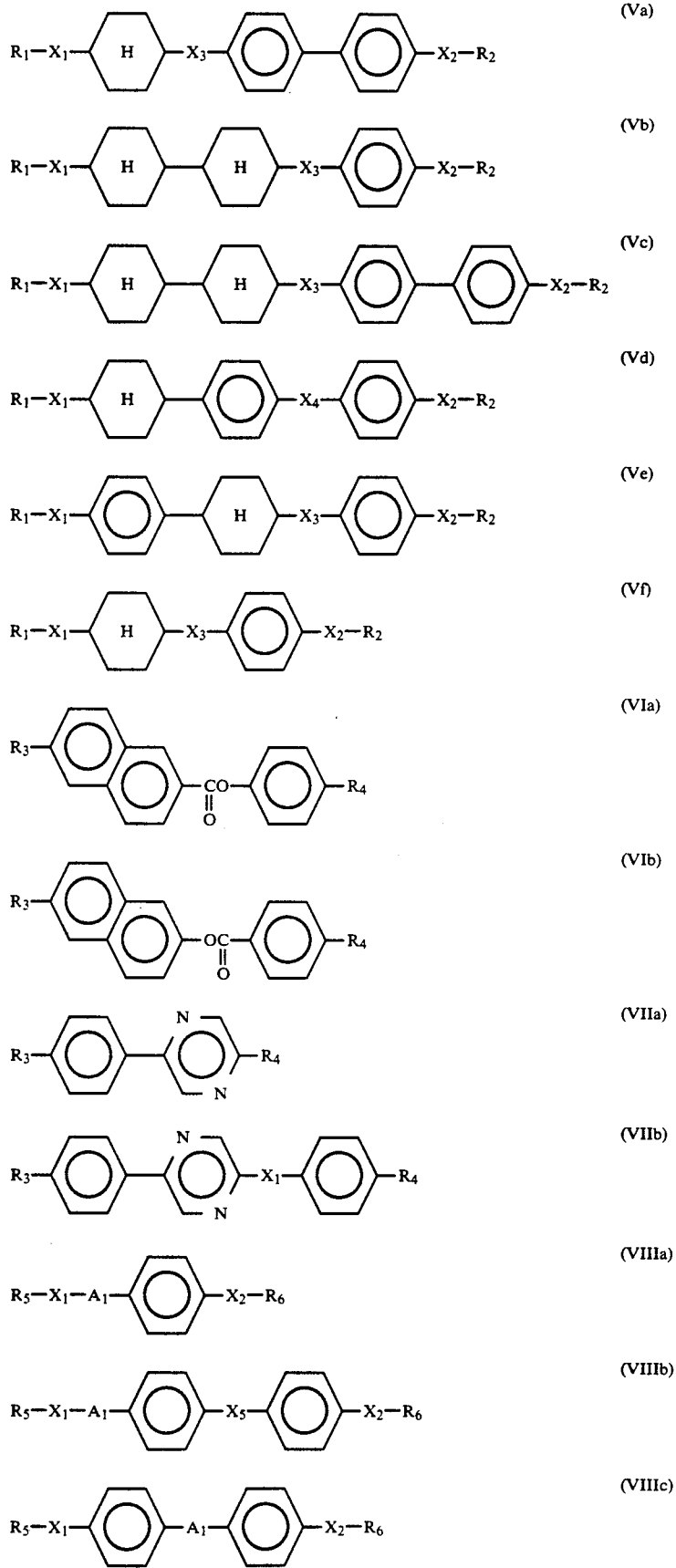

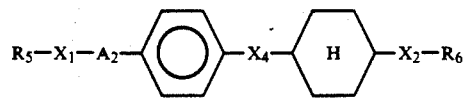 (IXa)

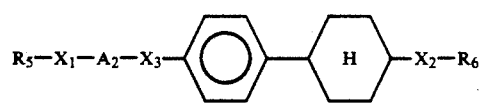 (IXb)

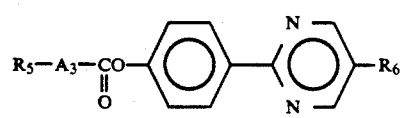 (Xa)

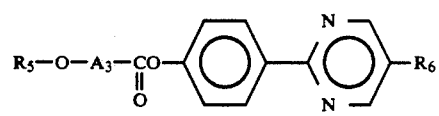 (Xb)

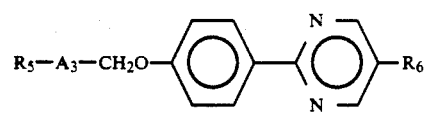 (Xc)

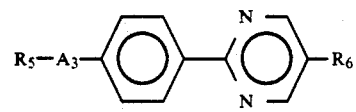 (Xd)

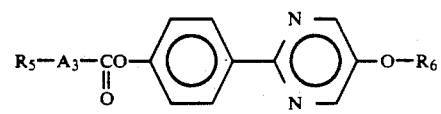 (Xe)

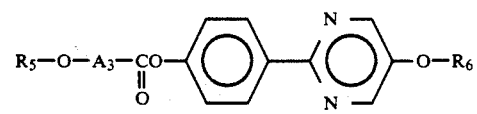 (Xf)

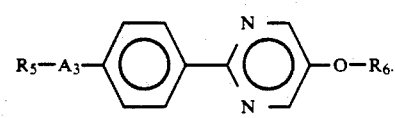 (Xg)

wherein $X_1'$ and $X_2'$ denote a single bond,

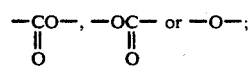

$X_3'$, $X_4'$ and $X_5'$ denote a single bond,

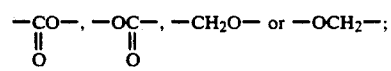

$Y'$, $Y_1'$, $Y_2'$ and $Y_3'$ denote H, halogen, $CH_3$ or $CF_3$; $A_1'$, $A_2'$ and $A_3'$ denote

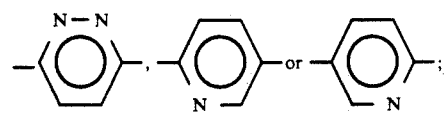

$R_1'$ and $R_2'$ denote a linear or branched alkyl group having 1-18 carbon atoms capable of including one or two or more non-neighboring methylene groups which can be replaced with —CHX— (wherein X is a halogen) and capable of further including one or two or more non-neighboring methylene groups other than those directly connected to $X_1'$ or $X_2'$ which can be replaced with at least one species of

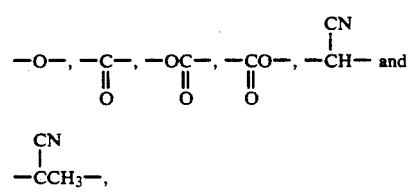

with proviso that $R_1'$ and $R_2'$ do not connect to a ring structure when $R_1'$ and $R_2'$ denote a halogenated alkyl group containing one methylene group replaced with —CHX— (wherein X is halogen); $R_3'$ and $R_4'$ denote a linear or branched alkyl group having 1-18 carbon atoms capable of including one or two or more non-neighboring methylene groups which can be replaced with —CHX— (wherein X is halogen) and capable of further including one or two or more non-neighboring methylene groups which can be replaced with at least one species of

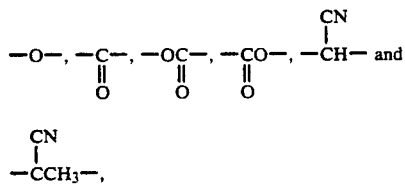

with proviso that $R_3'$ and $R_4'$ do not connect to a ring structure when $R_3'$ and $R_4'$ denote a halogenated alkyl group containing one methylene group replaced with —CHX— (wherein X is halogen); $R_5'$ and $R_6'$ denote a linear or branched alkyl group having 1-18 carbon atoms capable of including one or two or more non-neighboring methylene groups other than those directly connected to $X_1', X_2'$ or O which can be replaced with at least one species of

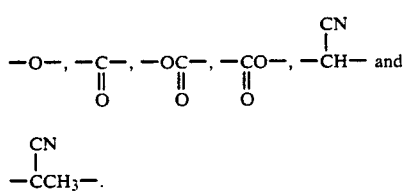

21. A cell according to claim 18, wherein the second mesomorphic compound is selected from the group consisting of the following formulae (II aa-dc), (III aa-cb), (IV aa-bf), (V aa-fa), (VII aa-bb), (VIII aa-cc), (IX aa-bb):

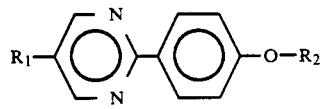 (IIaa)

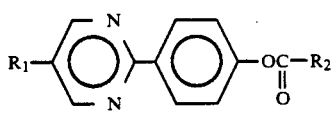 (IIab)

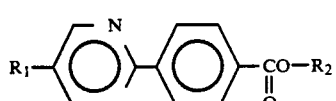 (IIac)

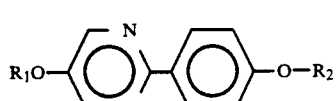 (IIad)

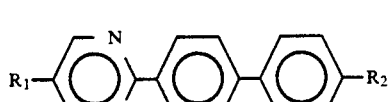 (IIba)

-continued

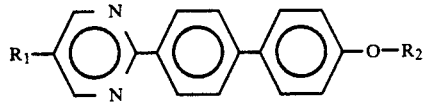 (IIbb)

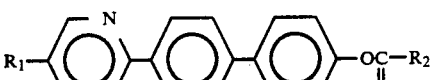 (IIbc)

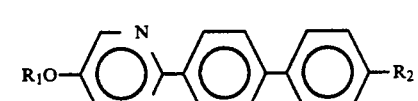 (IIbd)

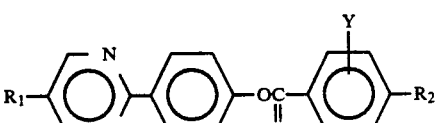 (IIca)

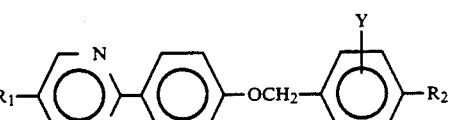 (IIcb)

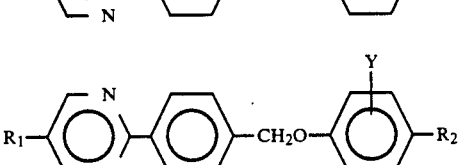 (IIcc)

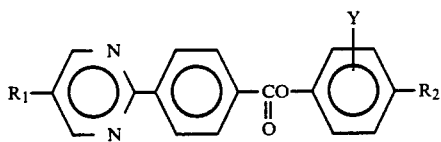 (IIcd)

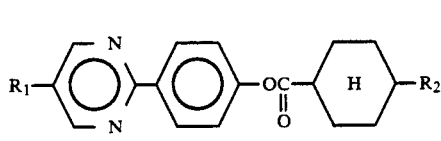 (IIda)

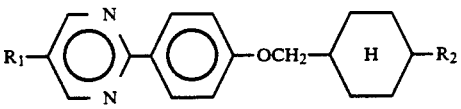 (IIdb)

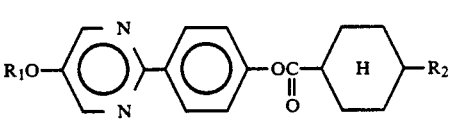 (IIdc)

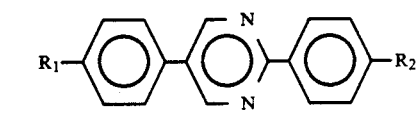 (IIIaa)

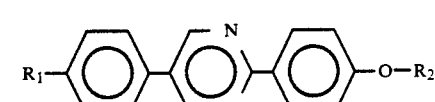 (IIIab)

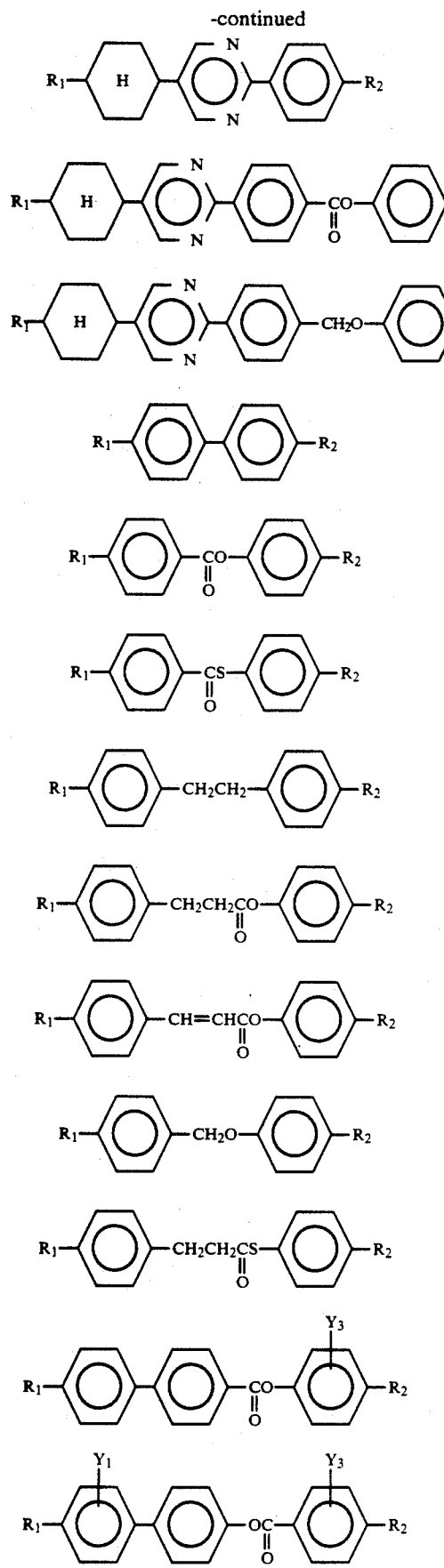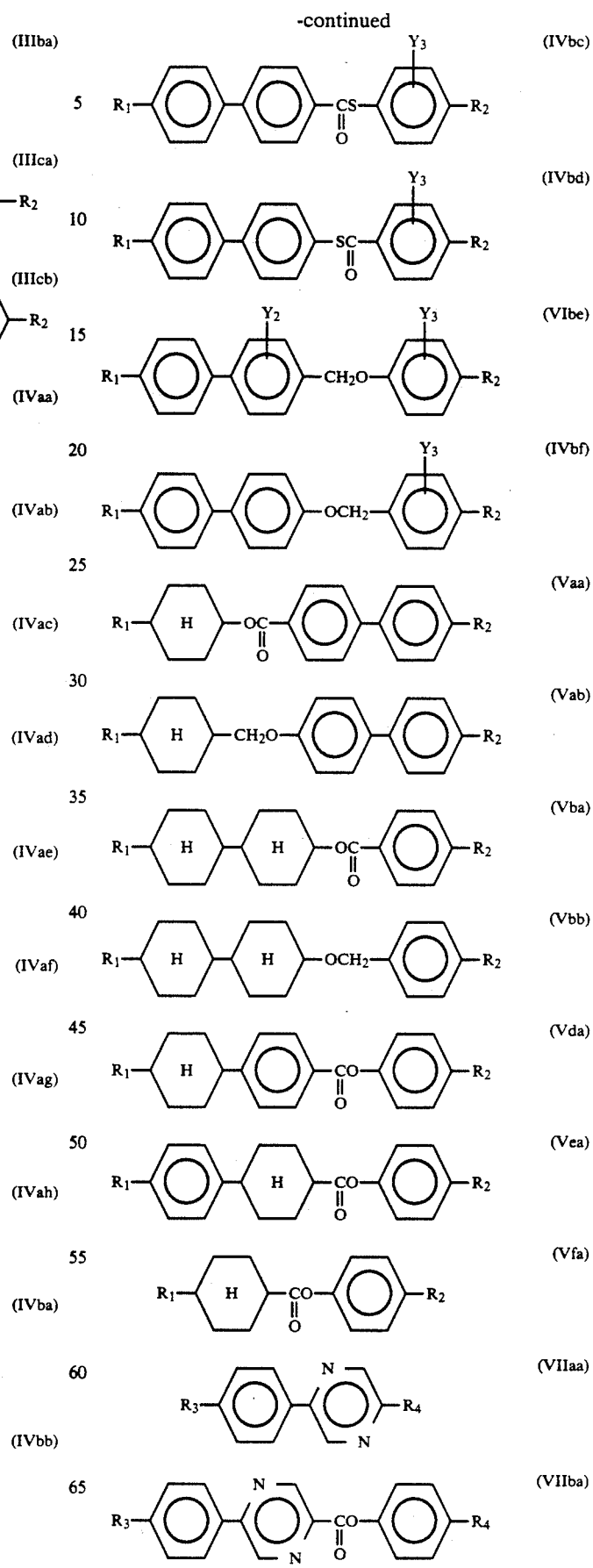

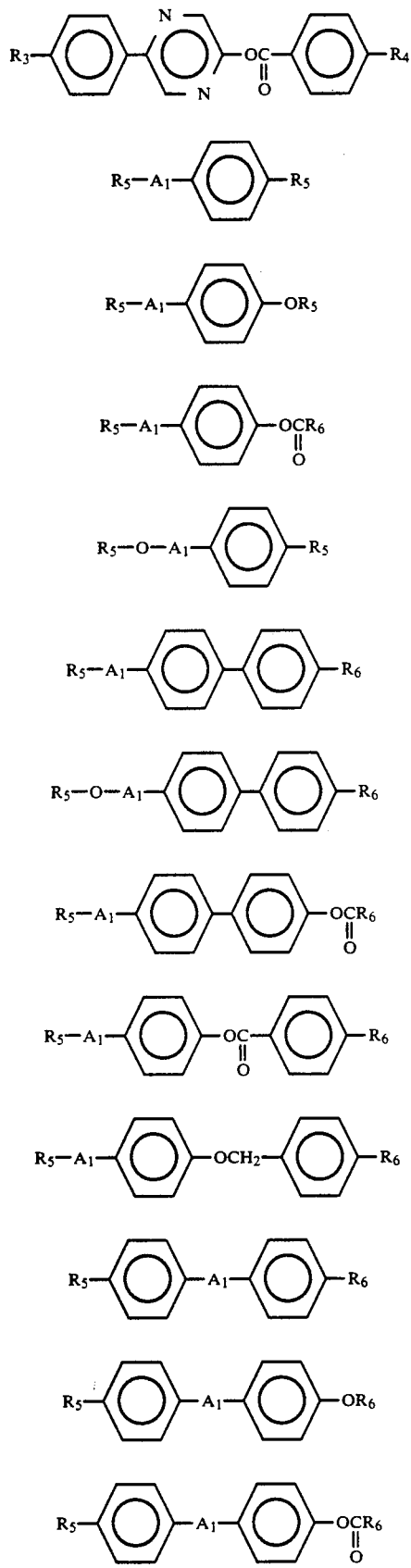

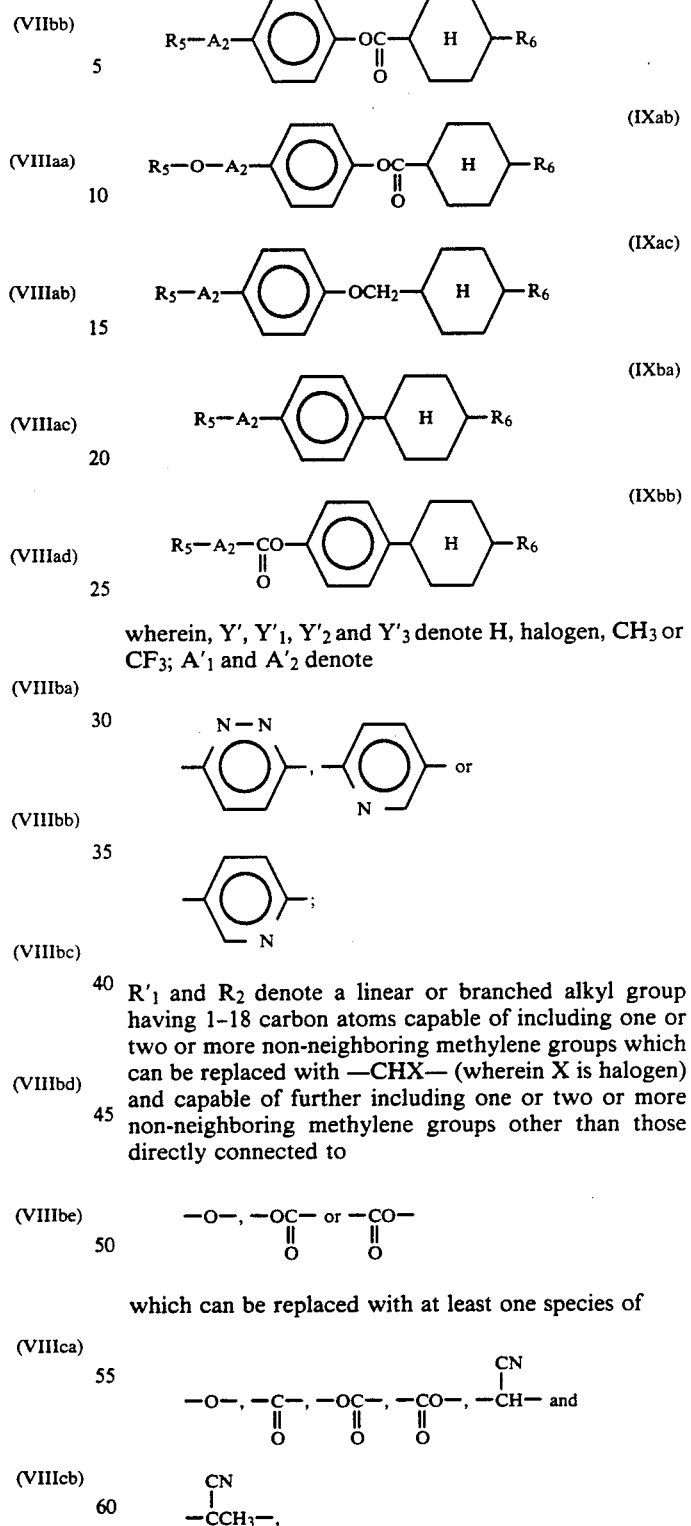

wherein, Y', Y'₁, Y'₂ and Y'₃ denote H, halogen, CH₃ or CF₃; A'₁ and A'₂ denote

R'₁ and R₂ denote a linear or branched alkyl group having 1-18 carbon atoms capable of including one or two or more non-neighboring methylene groups which can be replaced with —CHX— (wherein X is halogen) and capable of further including one or two or more non-neighboring methylene groups other than those directly connected to —O—, —OC— or —CO—
       ‖        ‖
       O        O which can be replaced with at least one species of —O—, —C—, —OC—, —CO—, —CH— and
     ‖      ‖      ‖      |
     O      O      O      CN

CN
        |
      —CCH₃—, with proviso that R₁' and R₂' do not connect to a ring structure when R₁' and R₂' denote a halogenated alkyl group containing one methylene group replaced with —CHX— (wherein X is halogen); R₃' and R₄' denote a linear or branched alkyl group having 1-18 carbon atoms capable of including one or two or more non-neighboring methylene groups which can be replaced with —CHX— (wherein X is halogen) and capable of further including one or two or more non-neighboring methylene groups which can be replaced with at least one species of

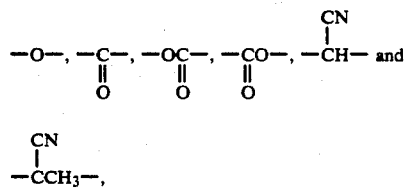

with the proviso that $R_3'$ and $R_4'$ do not connect to a ring structure when $R_3'$ and $R_4'$ denote a halogenated alkyl group containing one methylene group replaced with —CHX— (wherein X is halogen);

$R_5'$ and $R_6'$ denote a linear or branched alkyl group having 1–18 carbon atoms capable of including one or two or more non-neighboring methylene groups other than those directly connected to

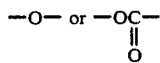

which can be replaced with at least one species of

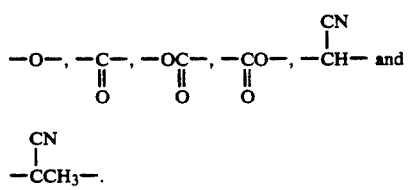

22. A display device comprising the cell of claim 16 and an alignment control layer.

23. A display apparatus comprising a device of claim and a circuit for driving a liquid crystal.

* * * * *

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

On title page,

AT [56] REFERENCES CITED

"Organisden" should read --Organischen--.

AT [57] ABSTRACT

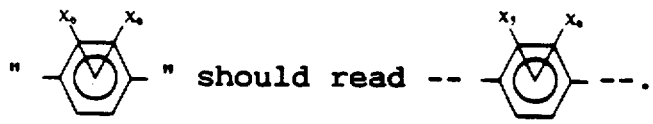

"$N_2$" should read --$n_2$-- and
"$A_2$ denote" should read --$A_2$ denotes--.

COLUMN 1

Line 26, "in which" should be deleted.

COLUMN 2

Line 23, "assumed" should read --assume--.
Line 36, "crystal" should be deleted.
Line 57, "a" should be deleted.

COLUMN 3

Line 40, "$X_2z$," should read --$X_2$,--.
Line 47, "bond" should read --bond,--.

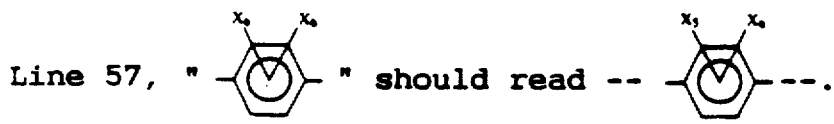

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 4

Line 7, "$X_0$" should read --$X_6$--.
Line 11, "at least $X_3$" should read
    --at least one of $X_2$ and $X_3$--.
Line 17, "0" should read --O--.
Line 30, "there between" should read --therebetween--.

Form [Ia], " 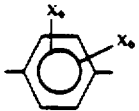 " should read -- 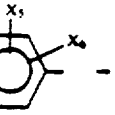 --.

COLUMN 5

Form [Ih], " 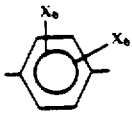 " should read -- 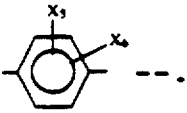 --.

Form [Iaa], " 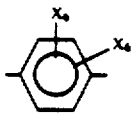 " should read -- 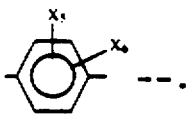 --.

COLUMN 6

Form [Iha], " 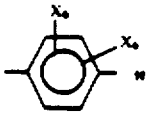 " should read --  --.

Line 63, "of" should read --or--.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 7

Line 19, "X" should read --x--.

COLUMN 8

Line 10, "$\overline{n1}$" should read --$\overline{\overline{n2}}$--.
Line 47, "these group" should read --these groups--.
Line 51, "Formula [I]in-" should read
--Formula [I] in- --.

COLUMN 11

Form (1-29), "$-(CH_2)_4-$" should read -- $-(CH_2)_6-$ --.

COLUMN 13

Form (1-38), "$C_{11}H_{25}$" should read --$C_{11}H_{23}$--.

COLUMN 23

Form (1-106), "$C_6H_{17}$" should read --$C_8H_{17}$--.

COLUMN 31

Form (1-153), "$CH_3$       " should read --$CH_3$      --.
            $|$                              $|$
            $CH_2H_5$                        $CHC_2H_5$

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.    Page 4 of 77

It is certified that error appears in the above-identified patent and that said Letters Patent is hereby corrected as shown below:

COLUMN 35

Form (1-175), "CH$_3$—CH$_2$H$_5$" should read --CH$_3$—CHC$_2$H$_5$--.

COLUMN 45

Form (1-236),  should read -- 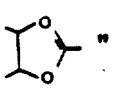 --.

COLUMN 57

Line 55, "3+f=0" should read --e+f=0--.
Line 65, "OR" should read --or--.
Form (IIb), "—X$_1$—" should read ----X$_1$.----.

COLUMN 59

Line 25, "Y$_2\cdot$, Y$_2\cdot$" should read --Y$_1$', Y$_2$'--.
Line 65,  should read -- 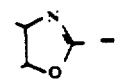 --.

COLUMN 60

Line 26,  should read -- 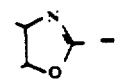 --.

UNITED STATES PATENT AND TRADEMARK OFFICE
CERTIFICATE OF CORRECTION

PATENT NO. : 5,244,596

DATED : September 14, 1993

INVENTOR(S) : TAKAO TAKIGUCHI ET AL.

It is certified that error appears in the above-identified patent and that said Letters Patent is hereby corrected as shown below:

COLUMN 61

Line 26, "$(CH_2)_2$" should read -- $(CH_2)_u$ --.
Line 66, "OR" should read --or--.

COLUMN 63

Line 37, "2" should read --w--.
Line 53, " of 0 - 2 " should read -- of o- 2 --

COLUMN 64

Line 42, "OR" should read --or--.

COLUMN 65

Line 29, "OR" should read --or--.

COLUMN 66

Line 32, "g" should read --q--.

COLUMN 68

Line 43, "(IIIcd);" should read --(IIIcb);--.

COLUMN 70

Line 66, "Formula" should read --Formulae--.

UNITED STATES PATENT AND TRADEMARK OFFICE
CERTIFICATE OF CORRECTION

PATENT NO. : 5,244,596

DATED : September 14, 1993

INVENTOR(S) : TAKAO TAKIGUCHI ET AL.

It is certified that error appears in the above-identified patent and that said Letters Patent is hereby corrected as shown below:

COLUMN 71

Line 20, "Formula" should read --Formulae--.
Line 22, "Formulas" should read --Formulae

COLUMN 72

Line 19, "Formula" should read --Formulae--.
Line 49, "formulation" should read --formulating--.

COLUMN 73

Line 15, "electrodes" should read --electrode--.
Line 66, "shows" should read --show--.

COLUMN 75

Line 39, "I-119" should read --1-119--.

COLUMN 77

Line 34, "IO-230)" should read --1-230--.
Line 48, "I-74" should read --1-74--.
Line 65, formula should be deleted.

UNITED STATES PATENT AND TRADEMARK OFFICE
CERTIFICATE OF CORRECTION

PATENT NO. : 5,244,596

DATED : September 14, 1993

INVENTOR(S) : TAKAO TAKIGUCHI ET AL.

It is certified that error appears in the above-identified patent and that said Letters Patent is hereby corrected as shown below:

COLUMN 78

Line 29, "which" should read --in which--.
Line 30, "to" should read --of--.
Line 38, "acid-chlorined" should read --acid-chlorinated--.
Line 42, "and" should read --with--.
Line 52, "0,40 g" should read --0.40 g--.

COLUMN 79

Line 2, "I-65)" should read --1-65)--.
Line 34, "I-85)" should read --1-85)--.

COLUMN 80

Line 10, "I-51" should read --1-51--.
Line 29, "-7.5-5°C." should read -- -7.5 - -5°C--.
Line 37, "(4-decyloxyphenyl)-" should read --2-(4-decyloxyphenyl)- --.
Line 46, "chloric" should read --hydrochloric--.
Line 55, "(0,84" should read --(0.84--.

COLUMN 81

Line 11, "I-190" should read --1-190--.
Line 37, "0.85 g" should read --0.95 g--.

UNITED STATES PATENT AND TRADEMARK OFFICE
CERTIFICATE OF CORRECTION

PATENT NO.  : 5,244,596
DATED       : September 14, 1993
INVENTOR(S) : TAKAO TAKIGUCHI ET AL.

It is certified that error appears in the above-identified patent and that said Letters Patent is hereby corrected as shown below:

COLUMN 82

Line 13, "I-162" should read --1-162--.
Line 49, "bonyl)phenyl" should read --bonyl)phenyl]--
        and "I-" should read --1- --.

COLUMN 83

Line 36, "was synthesized" should read
        --(Example Compound 1-140) was synthesized--.
Line 67, "I-141" should read --1-141--.

COLUMN 84

Line 29, "  COCH$_3$" should read --COCH$_3$--.

Line 33, "  COH" should read --COH--.

Line 45, "-carbonyl(phenyl)-" should read
        -- -carbonyl(phenyl))- --.
Line 50, "chloric" should read --hydrochloric--.
Line 52, "2-(4-carboxy-phenyl" should read
        --2-(4-carboxy-phenyl)--.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 85

Line 33, "$C_{22}H_{23}$" should read --$C_{11}H_{23}$--.
    Line 47, "I-190" should read --1-190--.
    Line 54, "I-190" should read --1-190--.

COLUMN 86

Line 4, "file" should read --film--.

COLUMN 87

Line 36, "I-230" should read --1-230--.

COLUMN 88

Line 7, "I-230" should read --1-230--.

COLUMN 91

Line 55, "I-5, I-18 and I-71" should read
         --1-5, 1-18 and 1-71--.
    Line 61, "I-105" should read --1-105--.
    Line 65, "I-131" should read --1-131--.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 92

Line 4, "I-170" should read --1-170--.
    Line 26, "I-105, I-131 and I-170" should read
        --1-105, 1-131 and 1-170--.
    Ex. Comp. No. I-127, "I-127" should read --1-127--.
    Ex. Comp. No. I-180, "I-180" should read --1-180--.
    Ex. Comp. No. I-198, "I-198" should read --1-198--.

COLUMN 95

Ex. Comp. No. I-79, "I-79" should read --1-79--.

Ex. Comp. No. I-154, "I-154" should read --1-154--.
    Ex. Comp. No. I-185, "I-185" should read --1-185--.

COLUMN 96

Line 50, "I-79, I-154 and I-185" should read
        --1-79, 1-154 and 1-185--.
    Ex. Comp. No. I-164, "I-164" should read --1-164--.
    Ex. Comp. No. I-194, "I-194" should read --1-194-.

COLUMN 97

Ex. Comp. No. I-225, "I-225" should read --1-225--.
    Line 28, "I-164, I-194 and I-225" should read
        --1-164, 1-194 and 1-225--.
    Ex. Comp. No. I-171, "I-171" should read --1-171--.
    Ex. Comp. No. I-213, "I-213" should read --1-213--.
    Ex. Comp. No. I-232, "I-232" should read --1-232--.

UNITED STATES PATENT AND TRADEMARK OFFICE
CERTIFICATE OF CORRECTION

PATENT NO. : 5,244,596

DATED : September 14, 1993

INVENTOR(S) : TAKAO TAKIGUCHI ET AL.

It is certified that error appears in the above-identified patent and that said Letters Patent is hereby corrected as shown below:

COLUMN 101

Line 67, "I-55, I-78 and I-202" should read
--1-55, 1-78 and 1-202--.

COLUMN 102

Line 36, "I-136" should read --1-136--.
Line 40, "I-176" should read --1-176--.
Line 45, "I-210" should read --1-210--.

COLUMN 103

Line 1, "I-136, I-176 and I-210" should read
--1-136, 1-176 and 1-210--.
Line 6, "I-52" should read --1-52--.
LIne 10, "I-73" should read --1-73--.
Line 14, "I-208" should read --1-208--.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 104

Line 20, "manner." should read
--manner. ¶

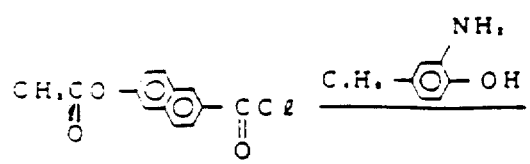

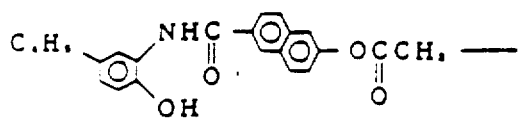

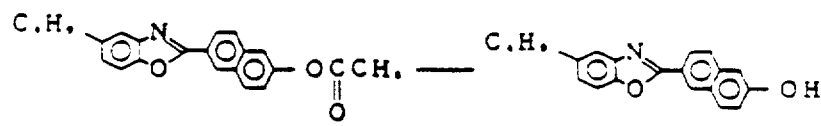

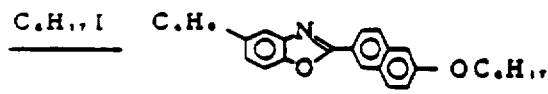

Lines 23-25, delete in entirety.
Line 29, "2-naphthoe" should read --2-naphthoic--.
Line 54, "chloric" should read --hydrochloric--.
Line 56, "acetoneethanol" should read --acetone-ethanol--.
Line 67, "water dried" should read --water, dried--.

UNITED STATES PATENT AND TRADEMARK OFFICE
CERTIFICATE OF CORRECTION

PATENT NO. : 5,244,596

DATED : September 14, 1993

INVENTOR(S) : TAKAO TAKIGUCHI ET AL.

It is certified that error appears in the above-identified patent and that said Letters Patent is hereby corrected as shown below:

COLUMN 105

Line 15, "I-249)" should read --1-249)--.
    Line 50, "I-250)" should read --1-250)--.

COLUMN 106

Line 11, "I-275)" should read --1-275)--.

COLUMN 107

Line 10, "I-5, I-18 and I-71" should read --1-5, 1-18 and 1-71--.
    Line 16, "I-190" should read --1-190--.
    Line 20, "I-145" should read --1-145--.
    Line 24, "I-249" should read --1-249--.
    Line 45, "I-79, I-154 and I-185" should read --1-79, 1-154 and 1-185--.
    Line 52, "I-250" should read --1-250--.
    Line 56, "I-275" should read --1-275--.
    Line 60, "I-286" should read --1-286--.

COLUMN 108

Line 12, "I-55, I-78 and I-202" should read --1-55, 1-78 and 1-202--.
    Line 17, "I-255" should read --1-255--.
    Line 22, "I-282" should read --1-282--.
    Line 26, "I-66" should read --1-66--.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 109

Line 25, " 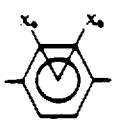 " should read --  --.

Line 43, "n is 1" should read --$n_1$ is 1--.
Line 51, "$Z_2$ denote" should read --$A_2$ denotes--.
Line 60, "[Ia]-]Ik]:" should read --[Ia]-[Ik]:--.

Form [Ia], " 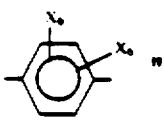 " should read -- 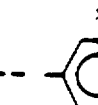 --.

COLUMN 110

Form [Ih], " 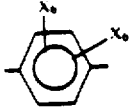 " should read -- 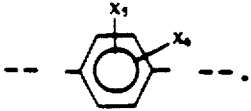 --.

COLUMN 111

Line 5, "  " should read -- 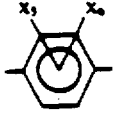 --.

Line 21, "$n_2$ or 0" should read --$n_2$ is 0--.

Form [Iaa], "  " should read -- 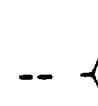 --.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.          Page 15 of 77

It is certified that error appears in the above-identified patent and that said Letters Patent is hereby corrected as shown below:

COLUMN 112

Form [Iha], 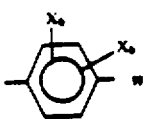 should read -- 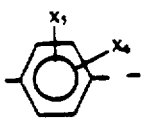 --.

Line 43, "(3);" should read --(3)--.
Line 51, "compounds" should read --compound--.

COLUMN 113

Form (II), "Y" should read --Y'--.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 115

Form (VI), " 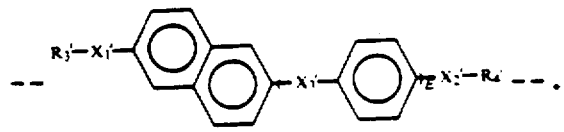 " should read

-- 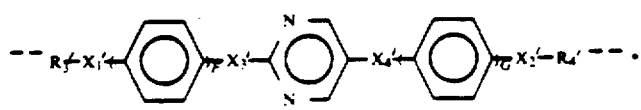 --.

Line 15, "$X_3$ denote" should read --$X_3$ denotes--.

Form (VII), " " should read

-- --.

Form (VIII), " "

should read -- --.

Form (IX), " "

should read -- --.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 116

Form (X), "  "

should read --  --.

Line 34, " -⟨O⟩- " should read -- -⟨O⟩- or--.

Line 38, "$X_3$. denote" should read --$X_3$. denotes--.

COLUMNS 118-121

Line 9, "Va-f)," should read --(Va-f),--.

Forms (IIa)-(Xg),

"
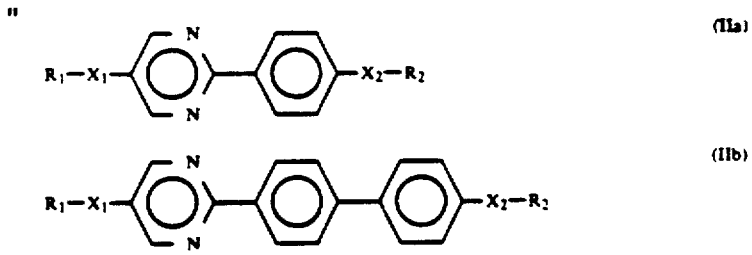

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 118-121

Forms (IIa)-(Xg), (continued)

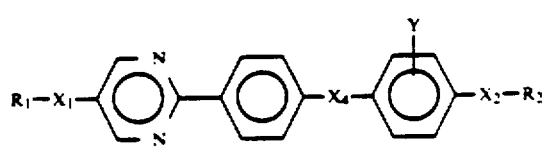 (IIc)

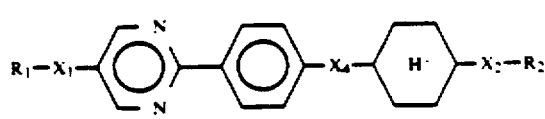 (IId)

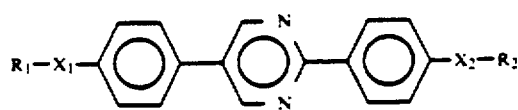 (IIIa)

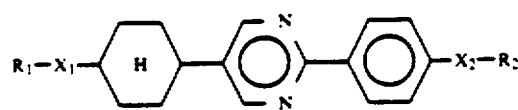 (IIIb)

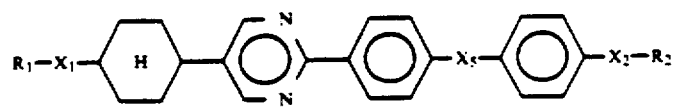 (IIIc)

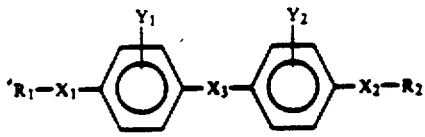 (IVa)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

<u>COLUMNS 118-121</u>

Forms (IIa)-(Xg), (continued)

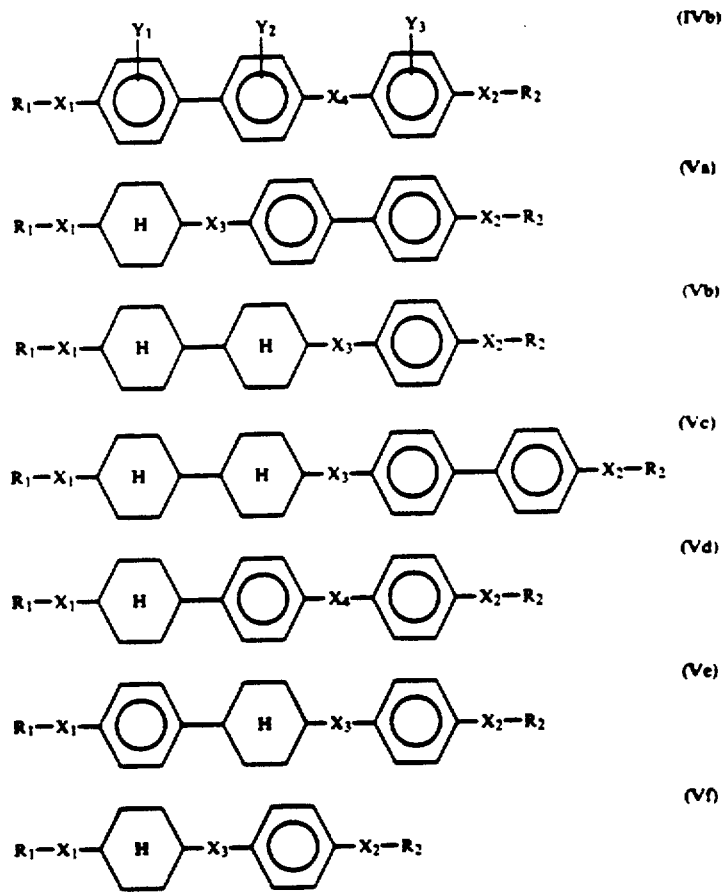

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 118-121

Forms (IIa)-(Xg), (continued)

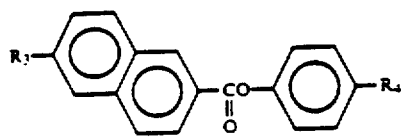 (VIa)

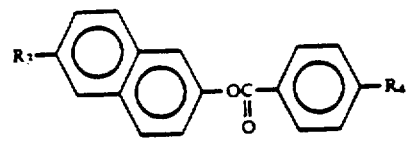 (VIb)

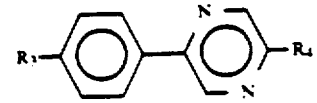 (VIIa)

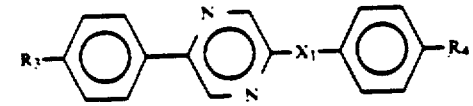 (VIIb)

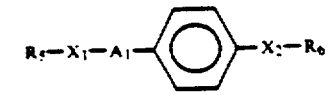 (VIIIa)

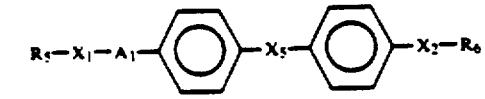 (VIIIb)

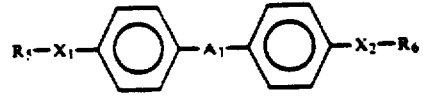 (VIIIc)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 118-121

Forms (IIa)-(Xg), (continued)

(IXa)

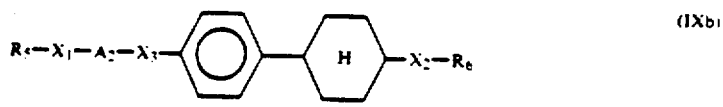 (IXb)

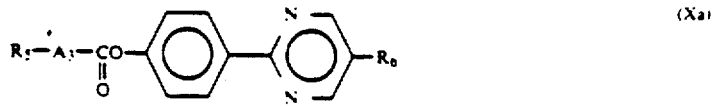 (Xa)

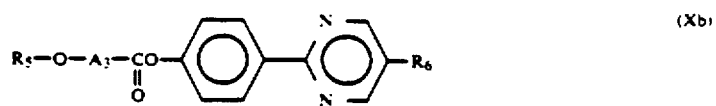 (Xb)

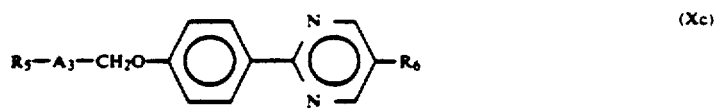 (Xc)

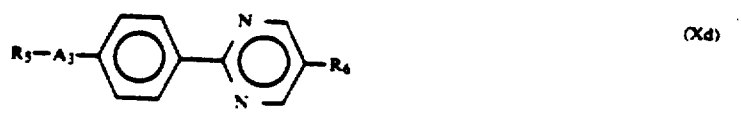 (Xd)

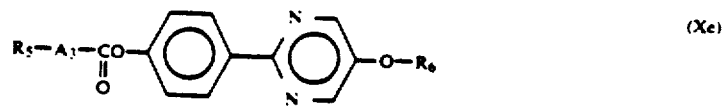 (Xe)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 118-121

Forms (IIa)-(Xg), (continued)

(Xf)

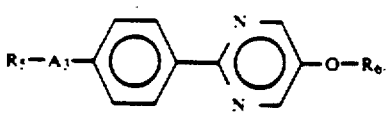 (Xg) "

should read

-- 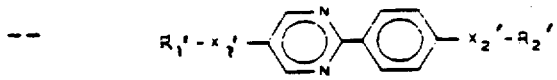 (IIa) [.]

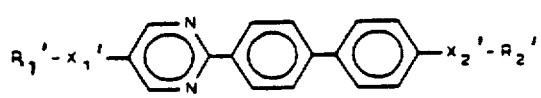 (IIb) [.]

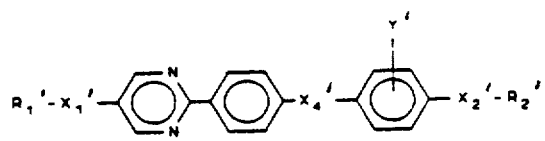 (IIc) [.]

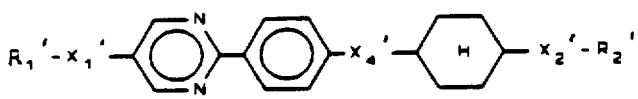 (IId) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 118-121

Forms (IIa)-(Xg), (continued)

(IIIa)[.]

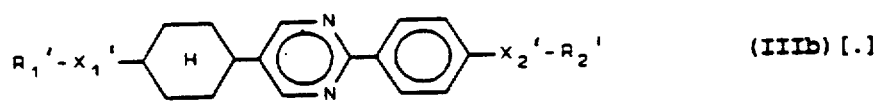  (IIIb)[.]

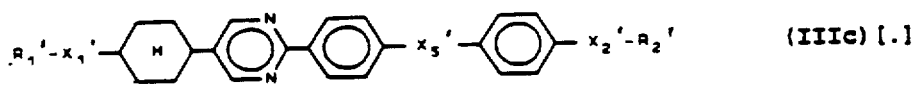  (IIIc)[.]

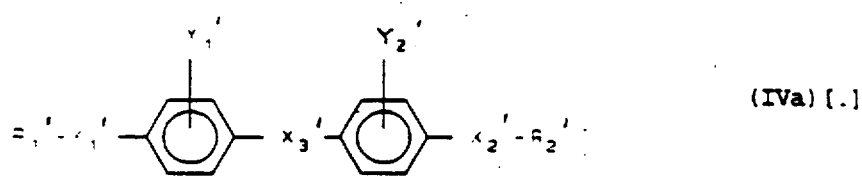  (IVa)[.]

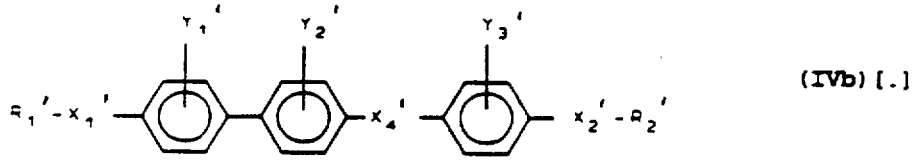  (IVb)[.]

  (Va)[.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 118-121

Forms (IIa)-(Xg), (continued)

(Vb) [.]

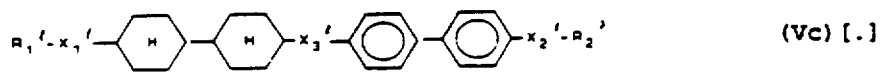 (Vc) [.]

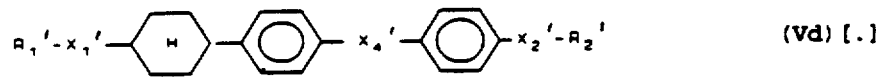 (Vd) [.]

 (Ve) [.]

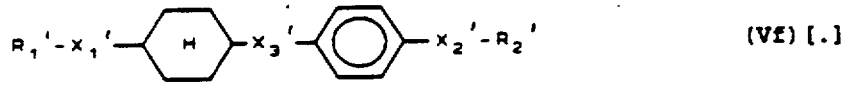 (Vf) [.]

 (VIa) [.]

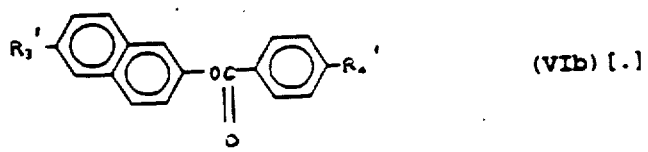 (VIb) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 118-121

Forms (IIa)-(Xg), (continued)

(VIIa) [.]

 (VIIb) [.]

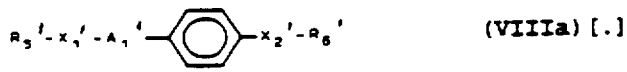 (VIIIa) [.]

 (VIIIb) [.]

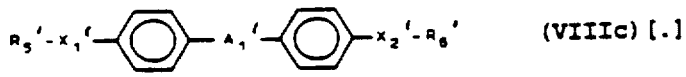 (VIIIc) [.]

 (IXa) [.]

 (IXb) [.]

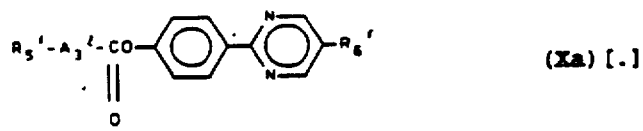 (Xa) [.]

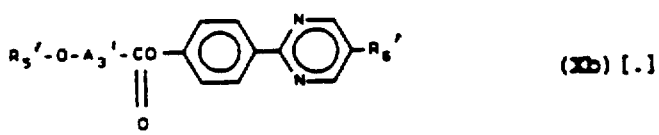 (Xb) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 118-121

Forms (IIa)-(Xg), (continued)

(Xc) [.]

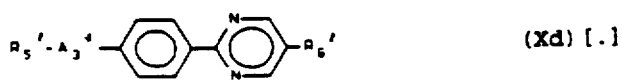 (Xd) [.]

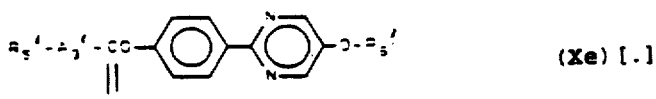 (Xe) [.]

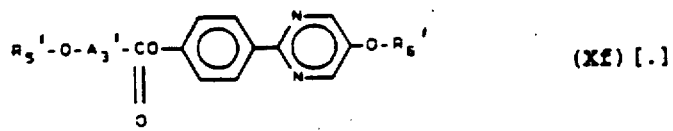 (Xf) [.]

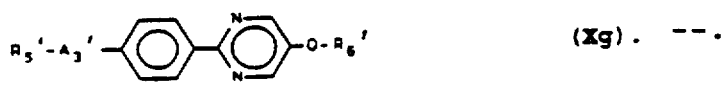 (Xg). --.

COLUMN 121

Line 59, "$R_1$" should read --$R_1'$--.
Line 64, "mor" should read --or--.

COLUMN 122

Line 67, "$R_3$" should read --$R_3'$--.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb)

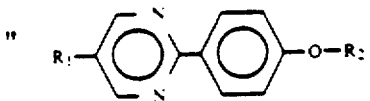
(IIaa)

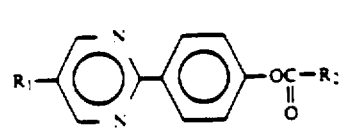
(IIab)

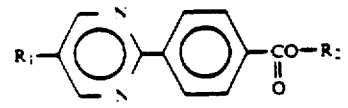
(IIac)

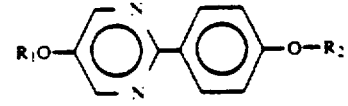
(IIad)

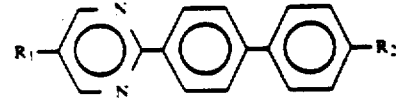
(IIba)

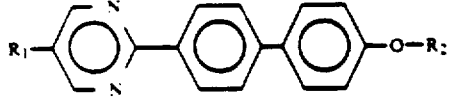
(IIbb)

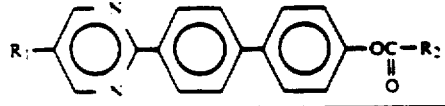
(IIbc)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

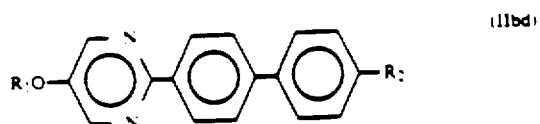 (IIbd)

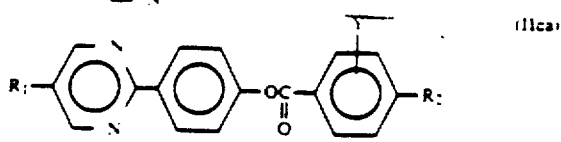 (IIca)

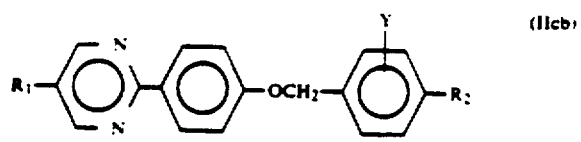 (IIcb)

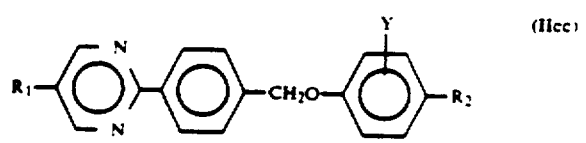 (IIcc)

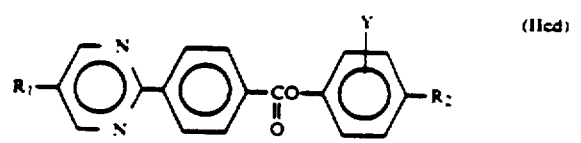 (IIcd)

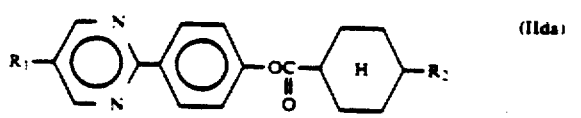 (IIda)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

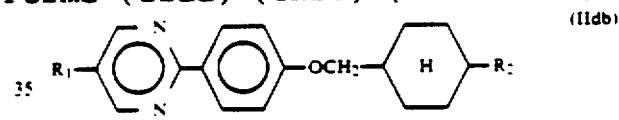
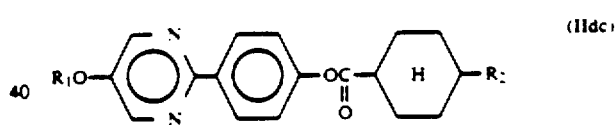
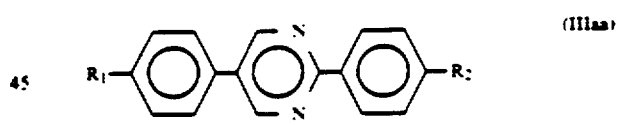
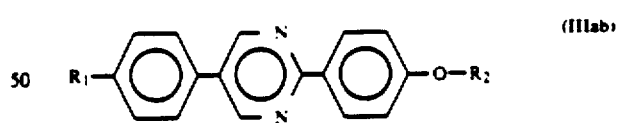
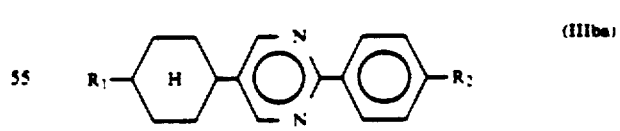
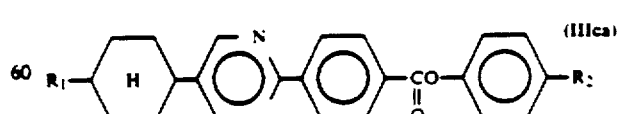
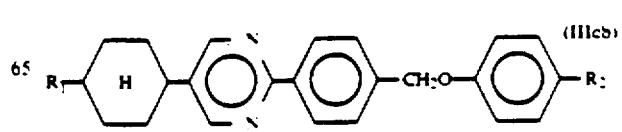

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

(IVaa)

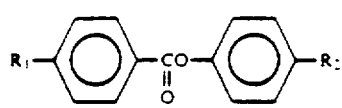
(IVab)

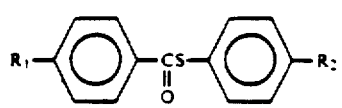
(IVac)

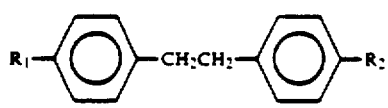
(IVad)

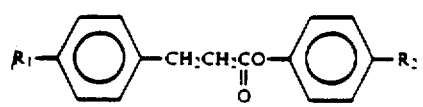
(IVae)

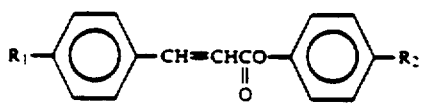
(IVaf)

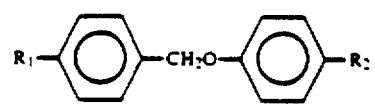
(IVag)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

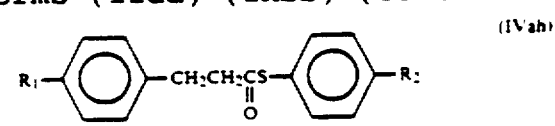
(IVah)

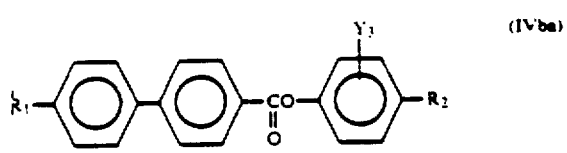
(IVba)

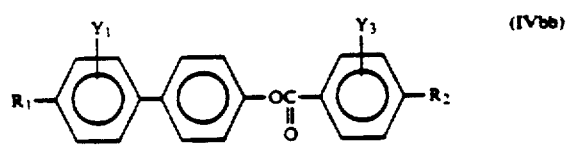
(IVbb)

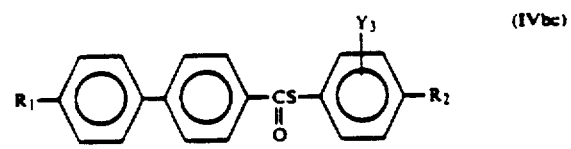
(IVbc)

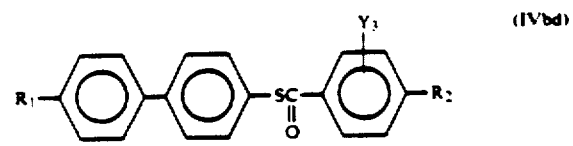
(IVbd)

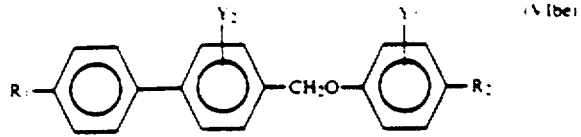
(IVbe)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

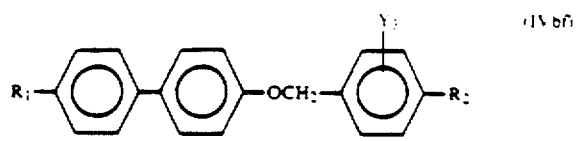

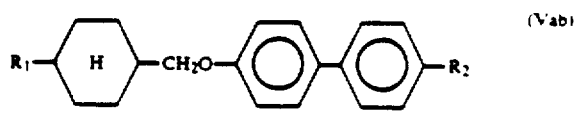

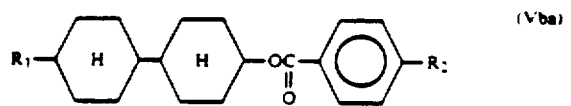

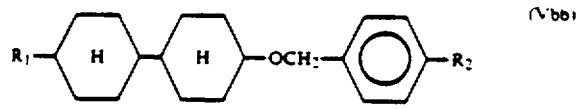

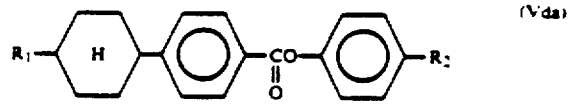

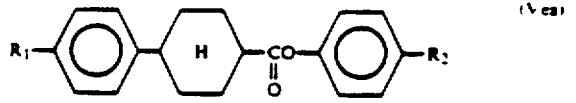

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

(Vfa)

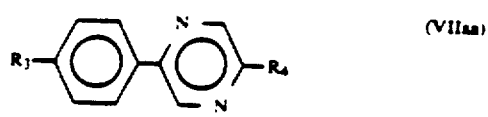

(VIIaa)

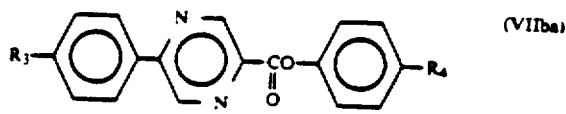

(VIIba)

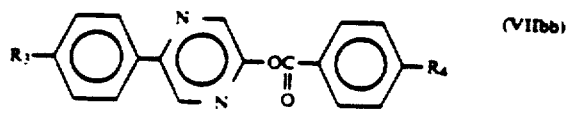

(VIIbb)

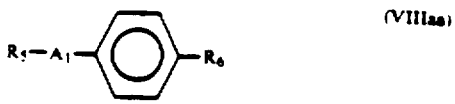

(VIIIaa)

(VIIIab)

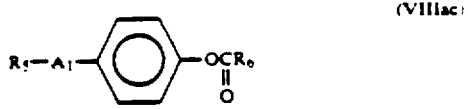

(VIIIac)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

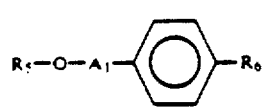
(VIIIad)

(VIIIba)

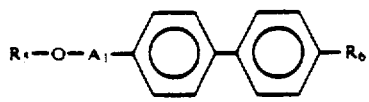
(VIIIbb)

(VIIIbc)

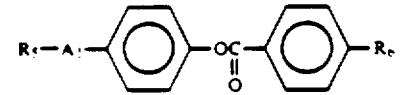
(VIIIbd)

(VIIIbe)

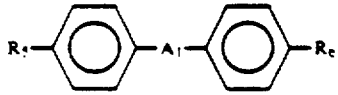
(VIIIca)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

(VIIIcb)

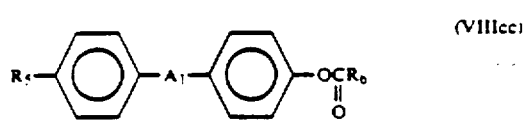
(VIIIcc)

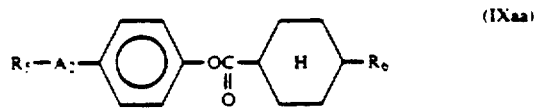
(IXaa)

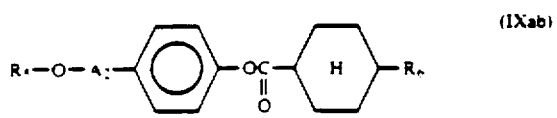
(IXab)

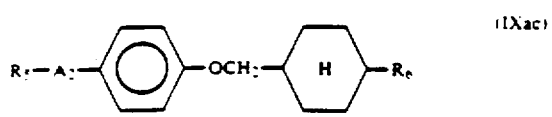
(IXac)

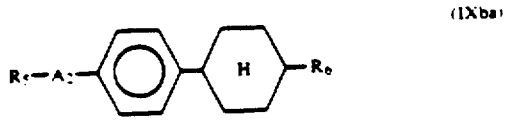
(IXba)

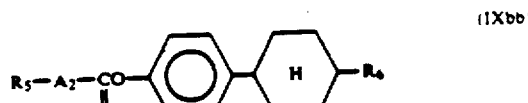
(IXbb)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

should read
--

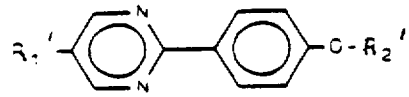 (IIaa) [.]

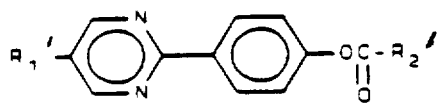 (IIab) [.]

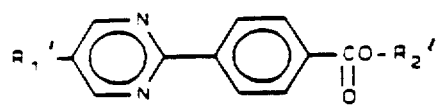 (IIac) [.]

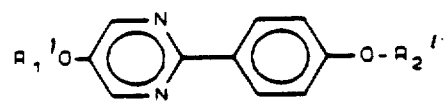 (IIad) [.]

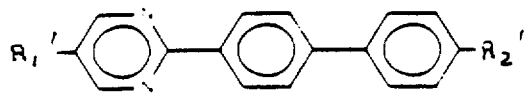 (IIba) [.]

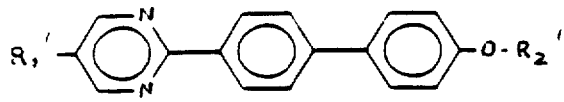 (IIbb) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

(IIbc) [.]

 (IIbd) [.]

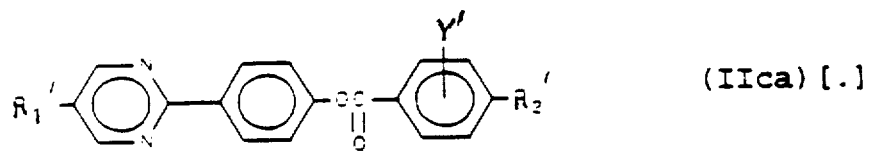 (IIca) [.]

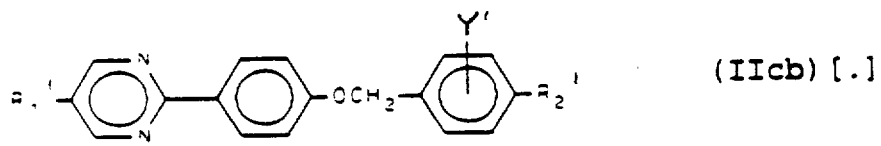 (IIcb) [.]

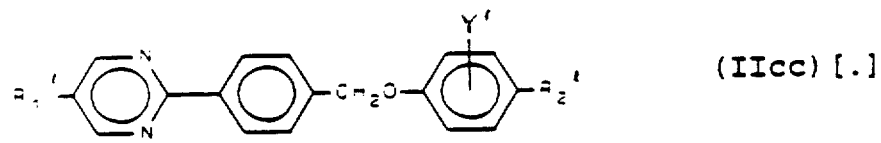 (IIcc) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

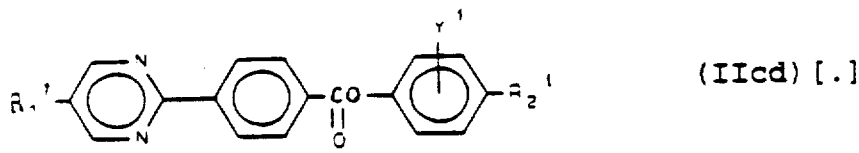  (IIcd) [.]

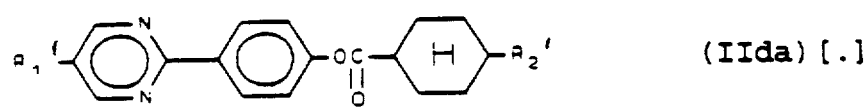  (IIda) [.]

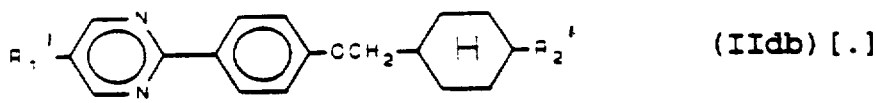  (IIdb) [.]

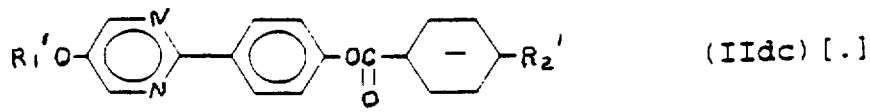  (IIdc) [.]

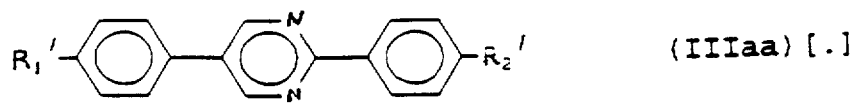  (IIIaa) [.]

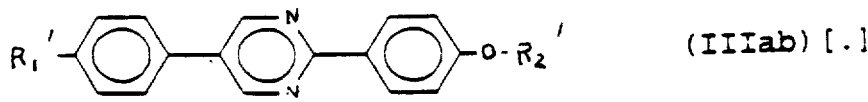  (IIIab) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

(IIIba) [.]

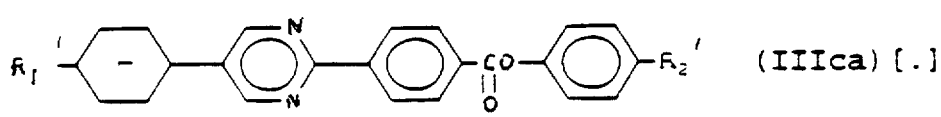 (IIIca) [.]

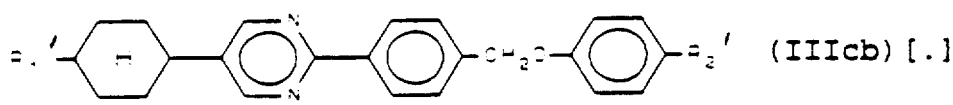 (IIIcb) [.]

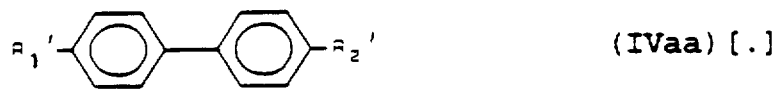 (IVaa) [.]

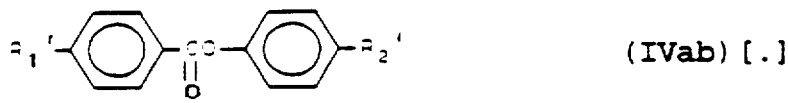 (IVab) [.]

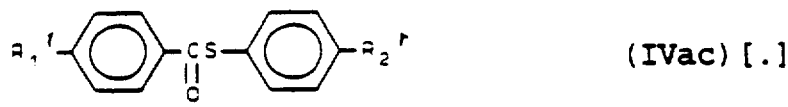 (IVac) [.]

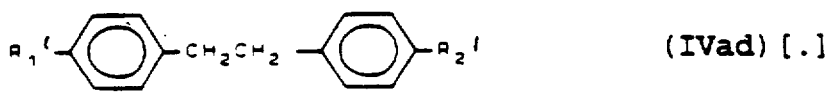 (IVad) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

(IVae) [.]

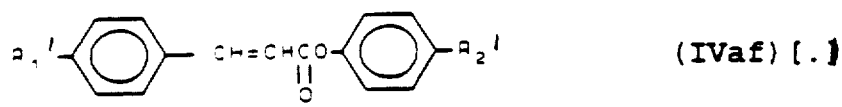   (IVaf) [.]

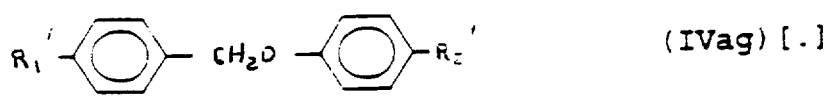   (IVag) [.]

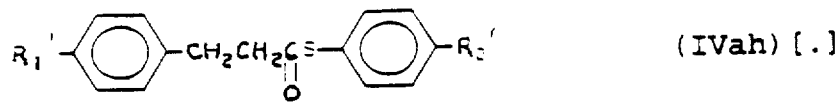   (IVah) [.]

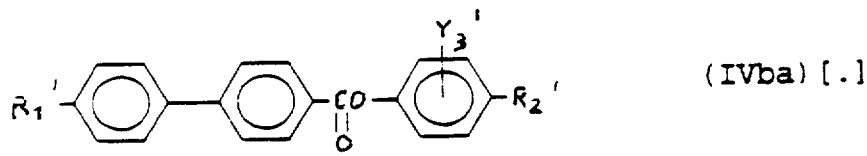   (IVba) [.]

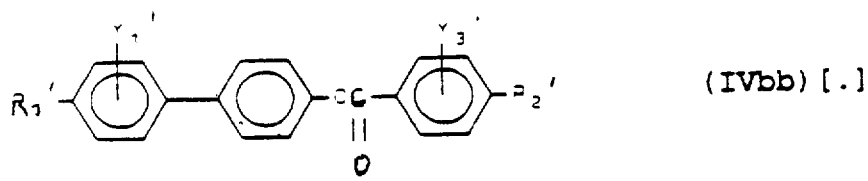   (IVbb) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

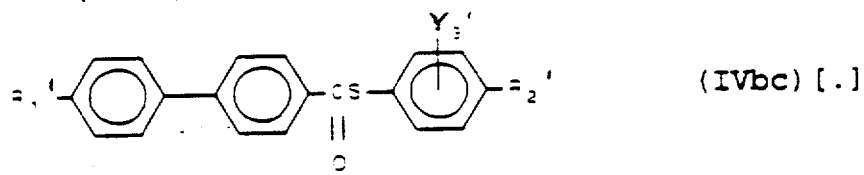    (IVbc) [.]

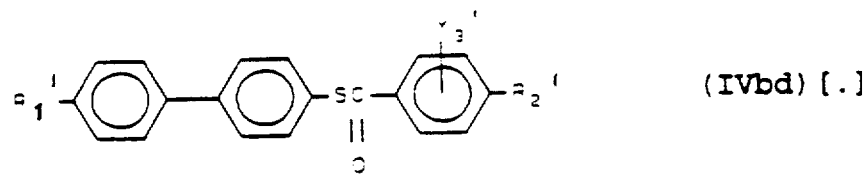    (IVbd) [.]

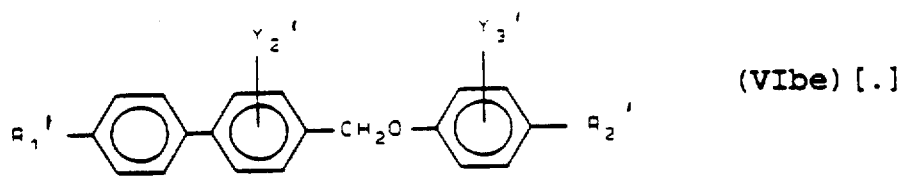    (VIbe) [.]

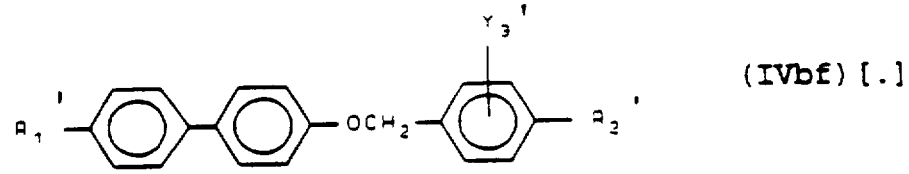    (IVbf) [.]

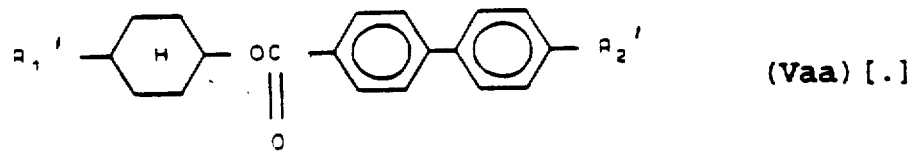    (Vaa) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

(Vab) [.]

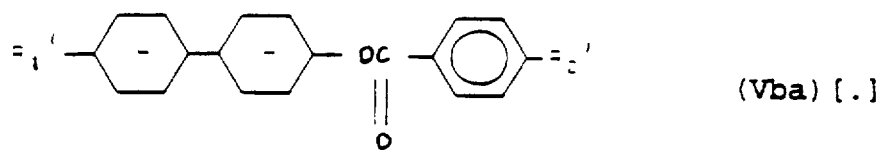  (Vba) [.]

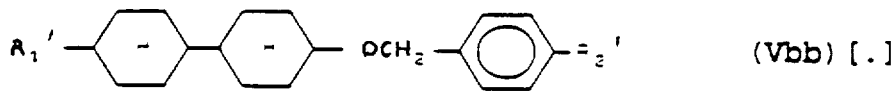  (Vbb) [.]

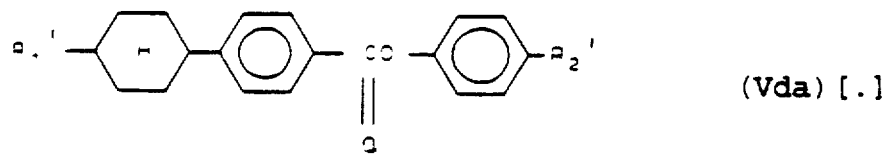  (Vda) [.]

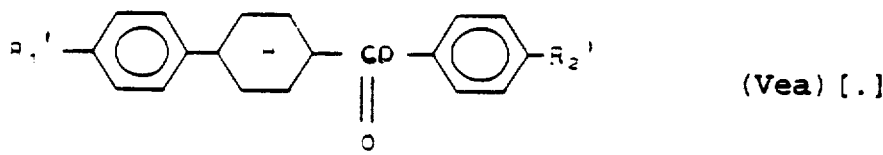  (Vea) [.]

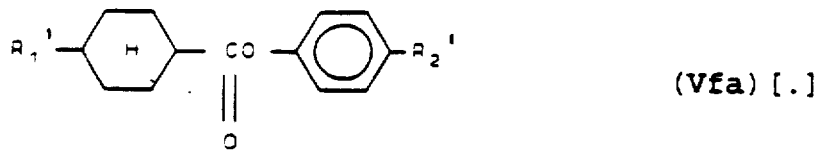  (Vfa) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

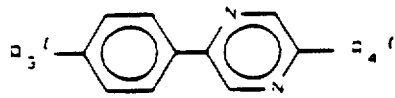 (VIIaa) [.]

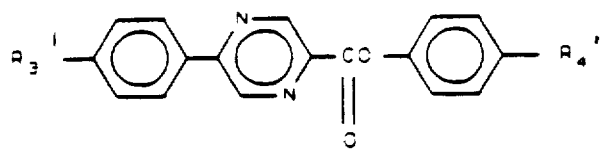 (VIIba) [.]

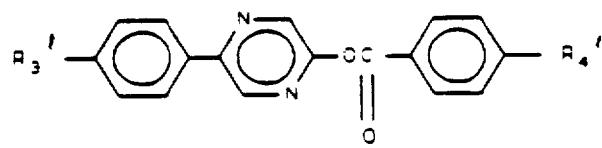 (VIIbb) [.]

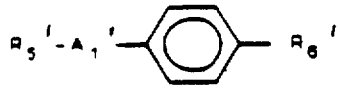 (VIIIaa) [.]

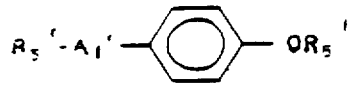 (VIIIab) [.]

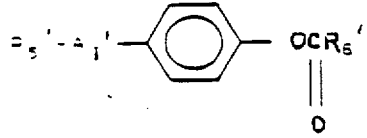 (VIIIac) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

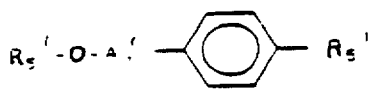 (VIIIad) [.]

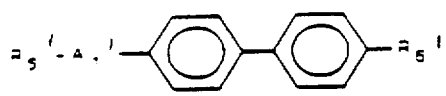 (VIIIba) [.]

 (VIIIbb) [.]

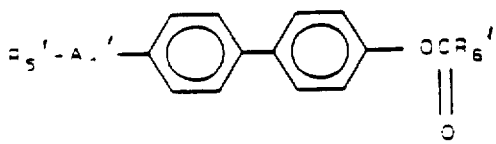 (VIIIbc) [.]

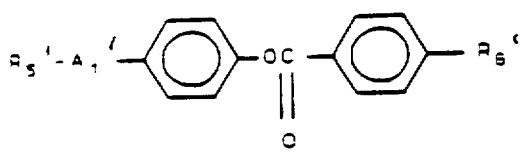 (VIIIbd) [.]

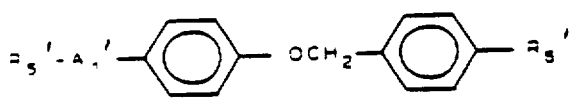 (VIIIbe) [.]

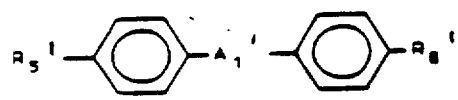 (VIIIca) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 123-128

Forms (IIaa)-(IXbb) (continued)

(VIIIcb) [.]

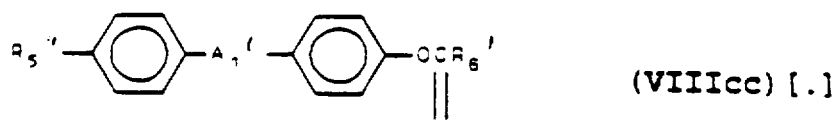 (VIIIcc) [.]

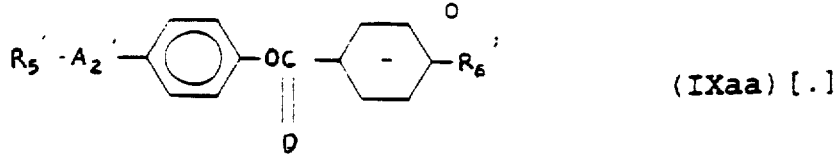 (IXaa) [.]

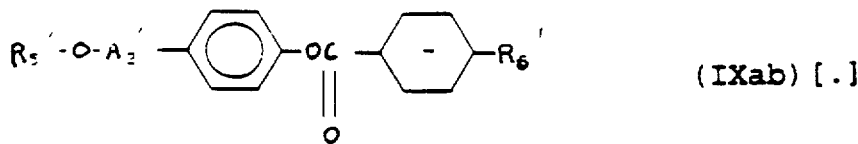 (IXab) [.]

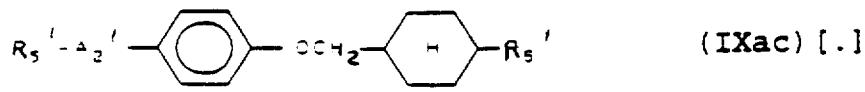 (IXac) [.]

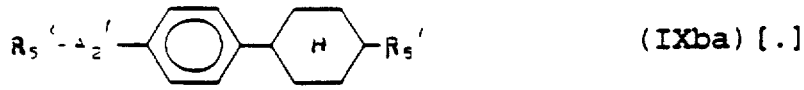 (IXba) [.]

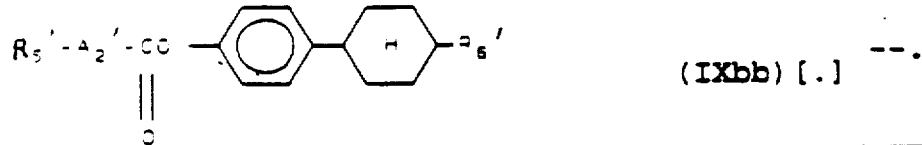 (IXbb) [.] --.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 128

Line 13, "$R'_1$, $Y'_2$ and $Y'_3$" should read --$R_1'$, $Y_2'$ and $Y_3'$--.
Line 14, "$A'_2$" should read --$A_2'$--.
Line 22, "$R'_1$ and $R_2$" should read --$R_1'$ and $R_2'$--.

COLUMN 129

Line 25, "CN
            |
         -OCCH$_3$-" should read --CN
                                  |
                                -CCH$_3$- --.

Column 129-134, line 44 to 13
Form (II), "$R_2$" should read --$R_2'$--.

COLUMN 130

Form (III), "  "

should read

-- 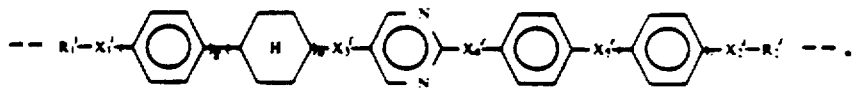 --.

Form (IV), "$X_3$" should read --$X_3'$--;
           "$X_4$" should read --$X_4'$--; and
           "$X_2$" should read --$X_2'$--
Line 39, "denote h," should read --denote H,--.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 131

Line 27, "$X_3$. denote" should read --$X_3'$ denotes--.
Form (VIII), "$X_3$" should read --$X_3'$--.

COLUMN 132

Form (X), "$R_6$" should read --$R_6'$--.
Line 59, "$X_3$. denote" should read --$X_3'$ denotes--.

COLUMN 134

Line 12, "CN " should read --CN --.
Line 18, "(VII a-c)," should read --(VIII a-c),--.

Forms (IIa)-(Xg),

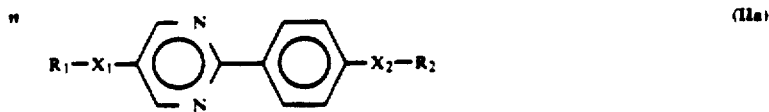

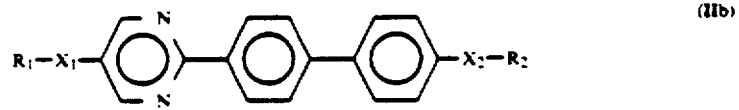

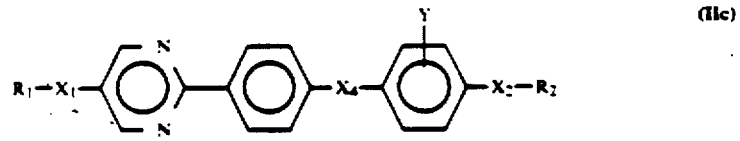

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 134

Forms (IIa)-(Xg) (continued)

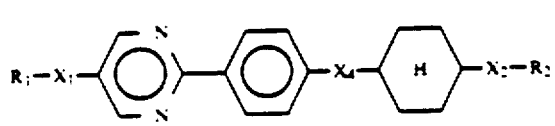 (IId)

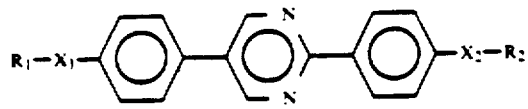 (IIIa)

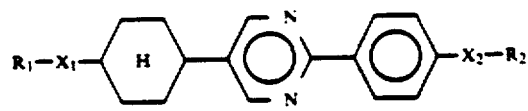 (IIIb)

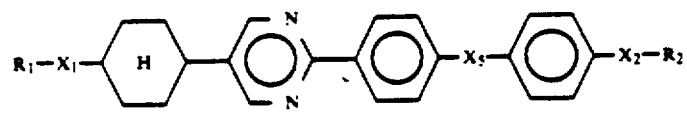 (IIIc)

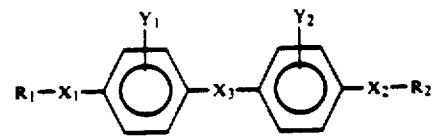 (IVa)

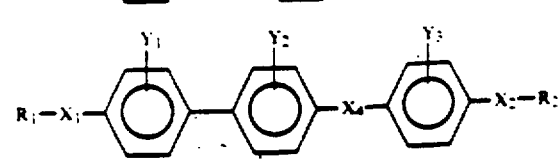 (IVb)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 134

Forms (IIa)-(Xg) (continued)

(Va)

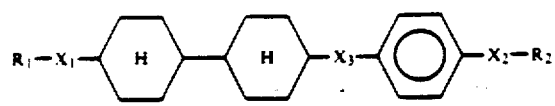 (Vb)

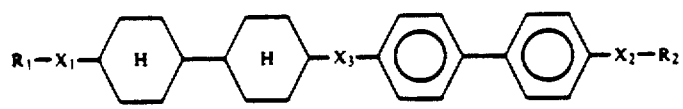 (Vc)

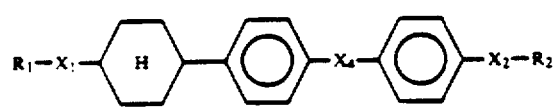 (Vd)

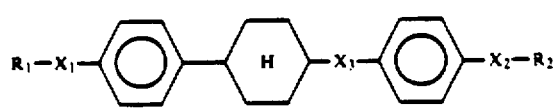 (Ve)

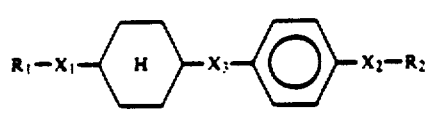 (Vf)

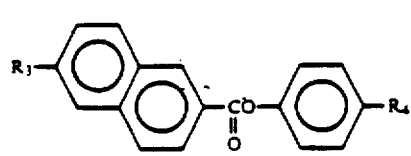 (VIa)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 134

Forms (IIa)-(Xg) (continued)

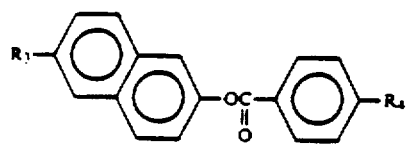
(VIb)

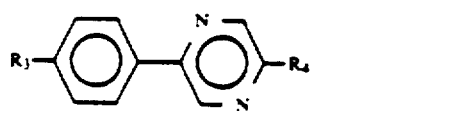
(VIIa)

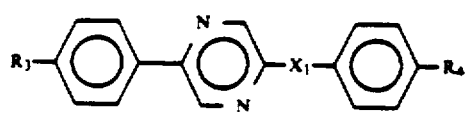
(VIIb)

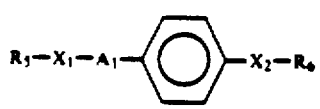
(VIIIa)

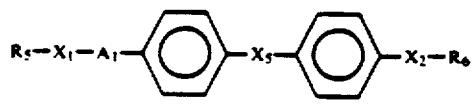
(VIIIb)

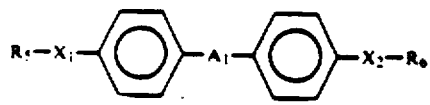
(VIIIc)

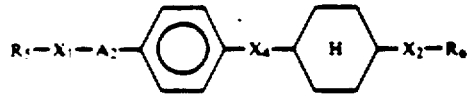
(IXa)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 134
Forms (IIa)-(Xg) (continued)

(IXb)

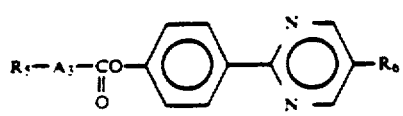 (Xa)

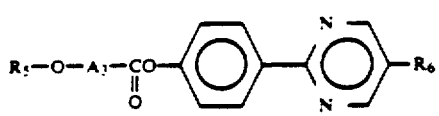 (Xb)

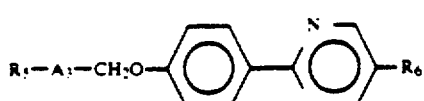 (Xc)

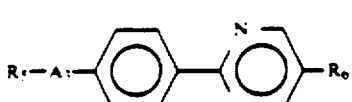 (Xd)

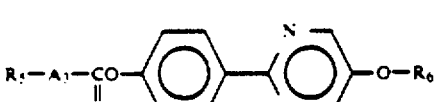 (Xe)

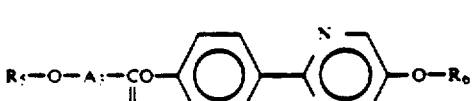 (Xf)

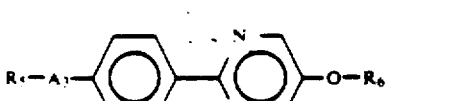 (Xg)

UNITED STATES PATENT AND TRADEMARK OFFICE
CERTIFICATE OF CORRECTION

PATENT NO. : 5,244,596

DATED : September 14, 1993

INVENTOR(S) : TAKAO TAKIGUCHI ET AL.

It is certified that error appears in the above-identified patent and that said Letters Patent is hereby corrected as shown below:

COLUMNS 134

Forms (IIa)-(Xg) (continued)

should read (IIa)[.]

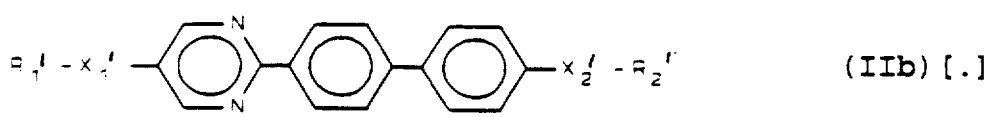 (IIb)[.]

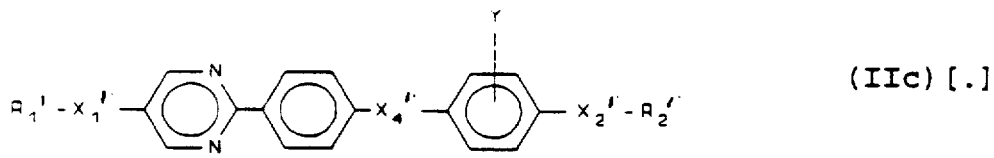 (IIc)[.]

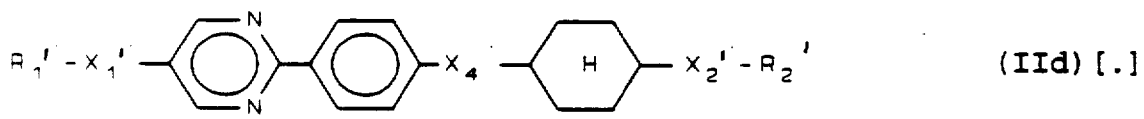 (IId)[.]

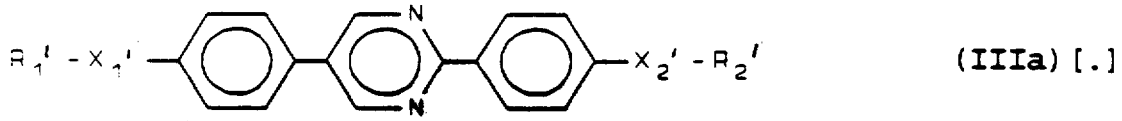 (IIIa)[.]

COLUMNS 134
Forms (IIa)-(Xg) (continued)
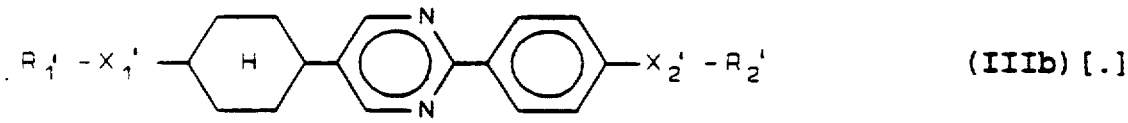 (IIIb) [.]
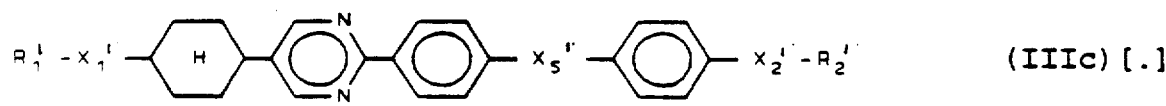 (IIIc) [.]
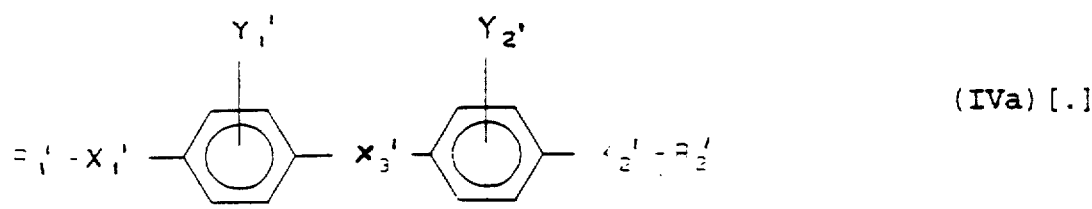 (IVa) [.]
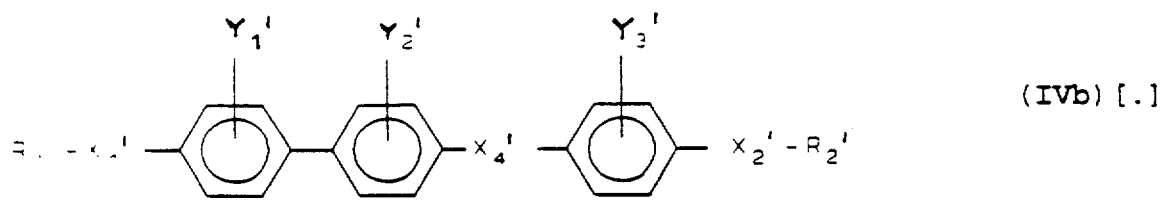 (IVb) [.]
 (Va) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 134

Forms (IIa)-(Xg) (continued)

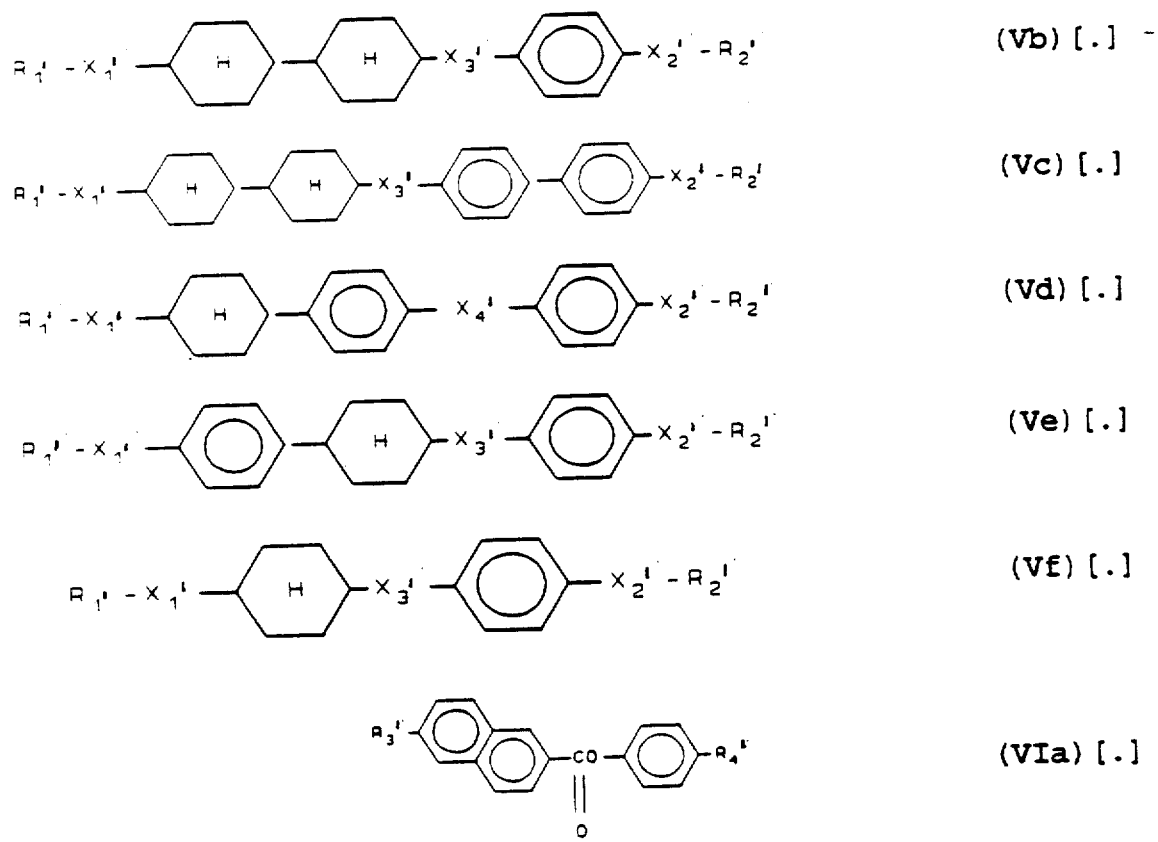

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 134

Forms (IIa)-(Xg) (continued)

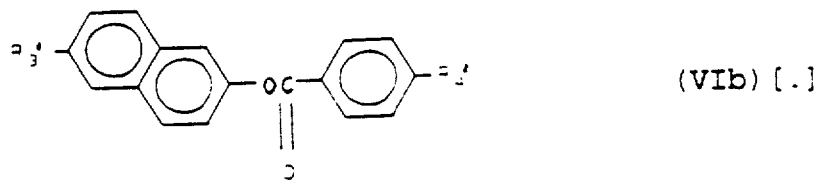   (VIb) [.]

   (VIIa) [.]

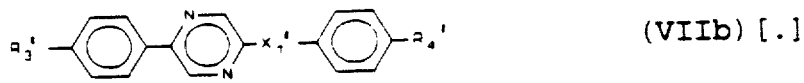   (VIIb) [.]

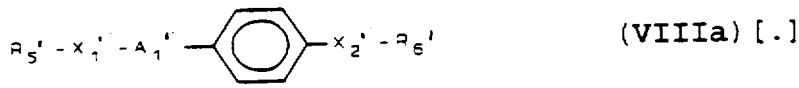   (VIIIa) [.]

   (VIIIb) [.]

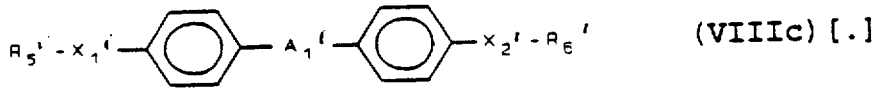   (VIIIc) [.]

   (IXa) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 134

Forms (IIa)-(Xg) (continued)

(IXb) [.]

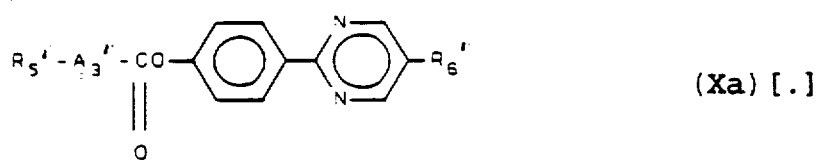 (Xa) [.]

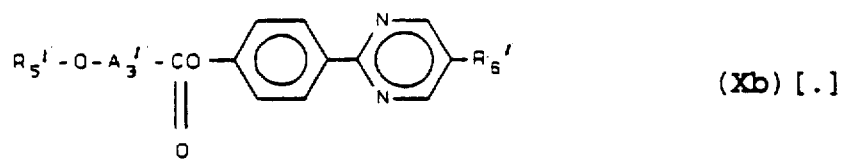 (Xb) [.]

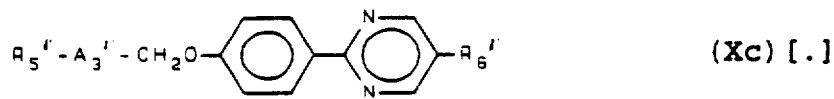 (Xc) [.]

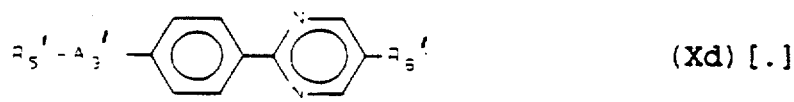 (Xd) [.]

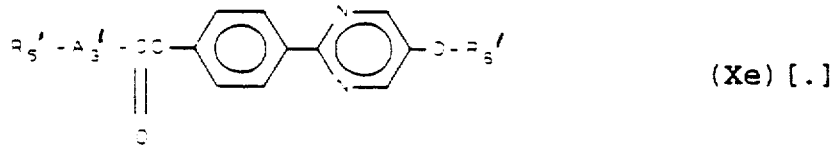 (Xe) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 134

Forms (IIa)-(Xg) (continued)

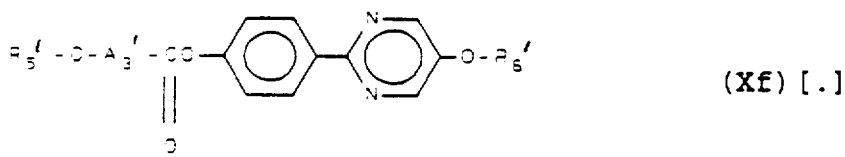  (Xf) [.]

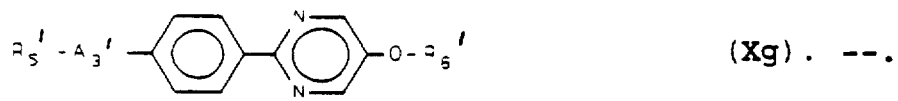  (Xg). --.

COLUMN 137

Line 67, "$R_1$" should read --$R_1'$--.

COLUMN 139

Line 17, "$R_3$" should read --$R_3'$--.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb),

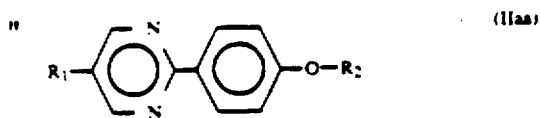
(IIaa)

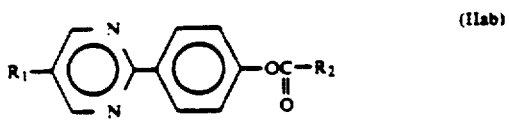
(IIab)

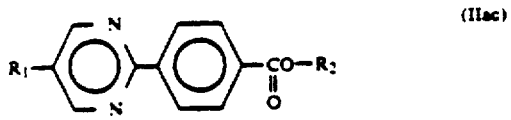
(IIac)

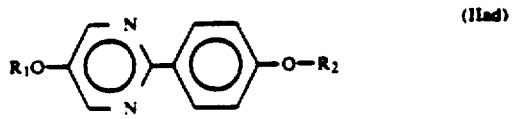
(IIad)

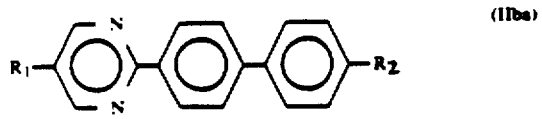
(IIba)

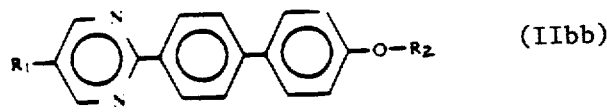
(IIbb)

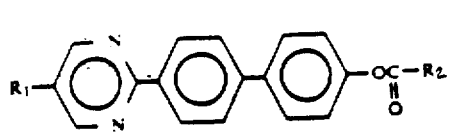
(IIbc)

COLUMNS 139-144
Forms (IIaa)-(IXbb), (Continued)
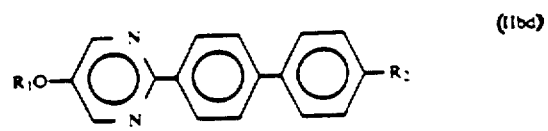
(IIbd)
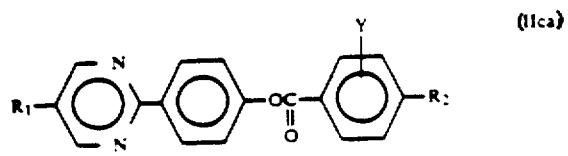
(IIca)
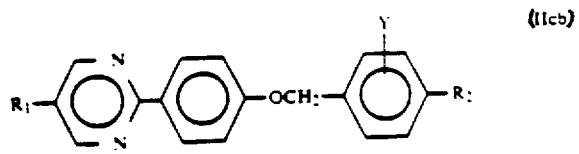
(IIcb)
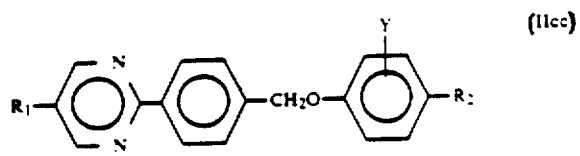
(IIcc)
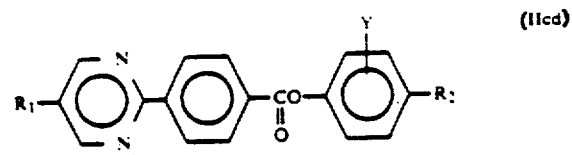
(IIcd)
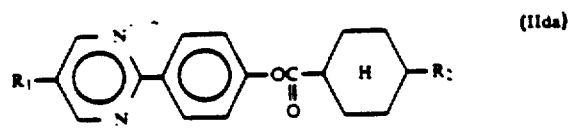
(IIda)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

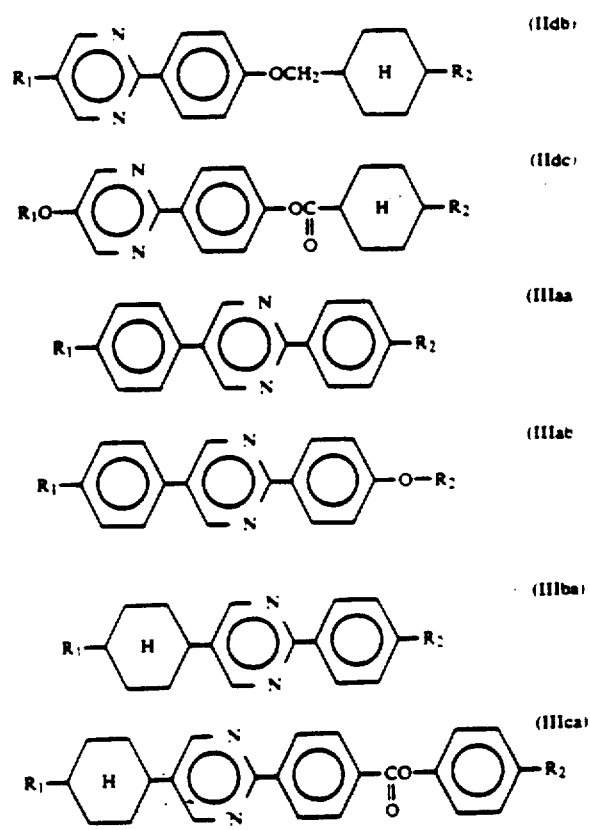

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

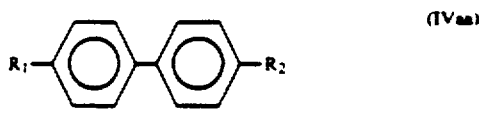

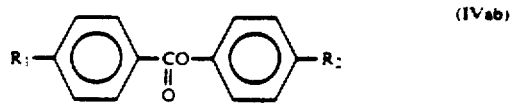

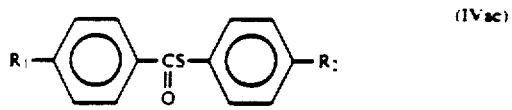

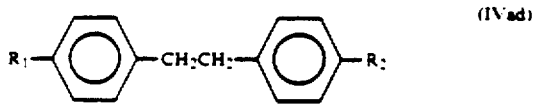

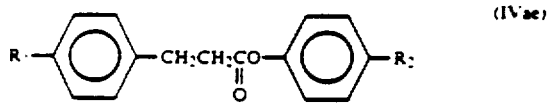

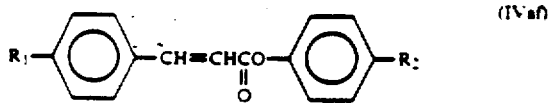

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

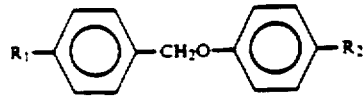 (IVag)

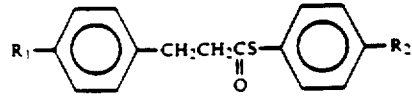 (IVah)

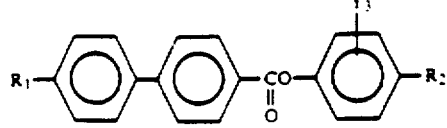 (IVba)

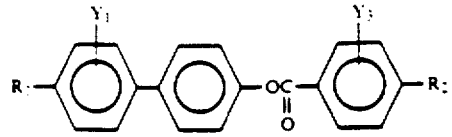 (IVbb)

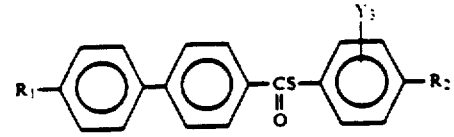 (IVbc)

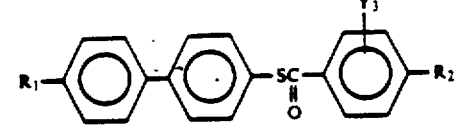 (IVbd)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

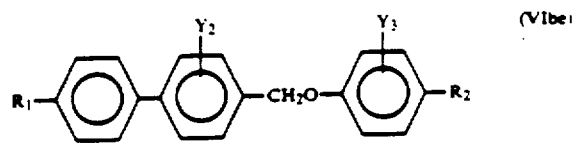
(VIbe)

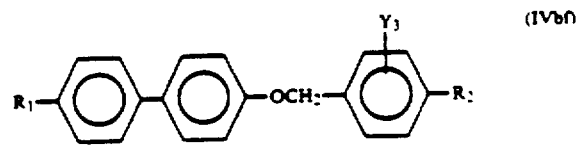
(IVbf)

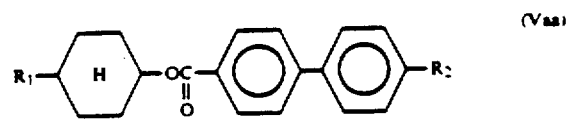
(Vaa)

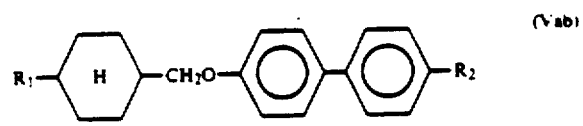
(Vab)

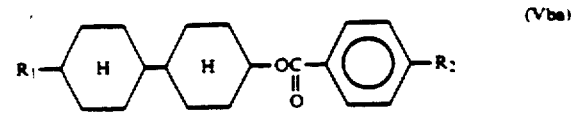
(Vba)

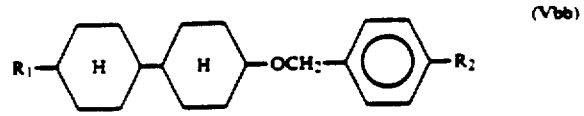
(Vbb)

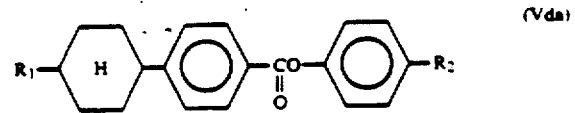
(Vda)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

(Vea)

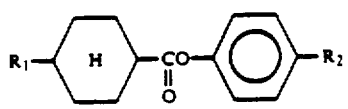 (Vfa)

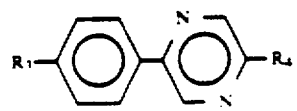 (VIIaa)

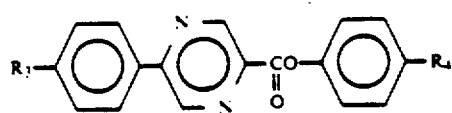 (VIIba)

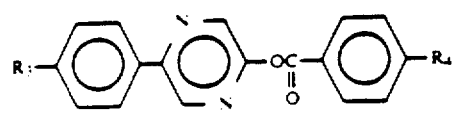 (VIIbb)

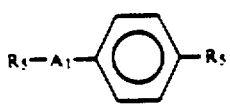 (VIIIaa)

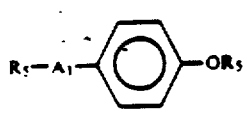 (VIIIab)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

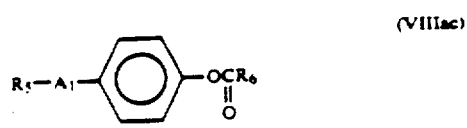 (VIIIac)

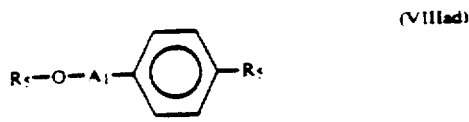 (VIIIad)

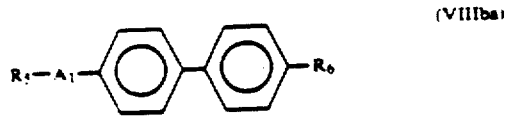 (VIIIba)

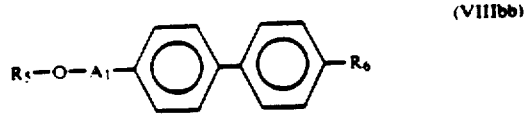 (VIIIbb)

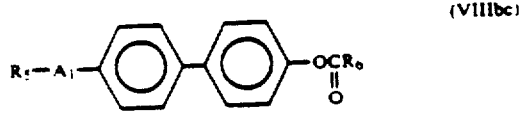 (VIIIbc)

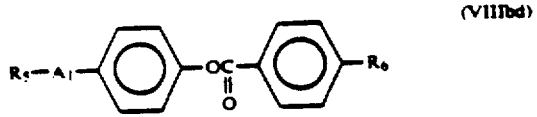 (VIIIbd)

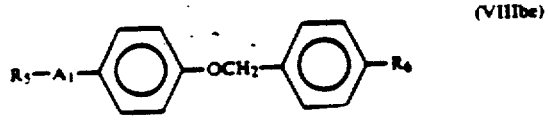 (VIIIbe)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144
Forms (IIaa)-(IXbb), (Continued)

(VIIIca)

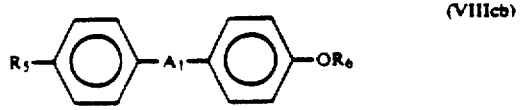 (VIIIcb)

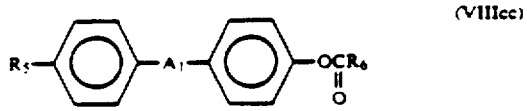 (VIIIcc)

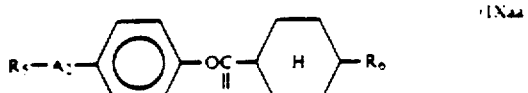 (IXaa)

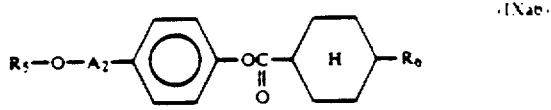 (IXab)

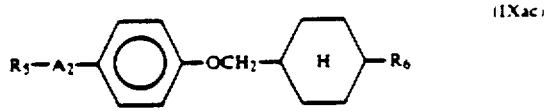 (IXac)

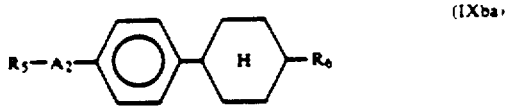 (IXba)

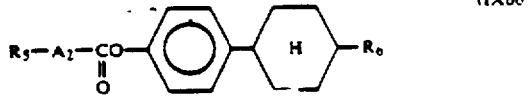 (IXbb)

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)
should read

--

(IIaa) [.]

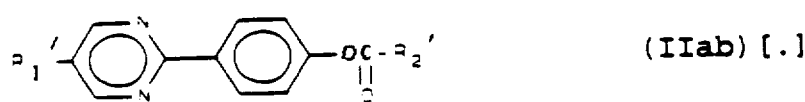 (IIab) [.]

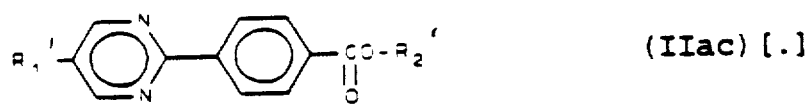 (IIac) [.]

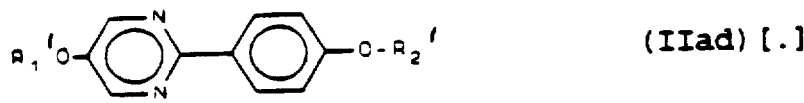 (IIad) [.]

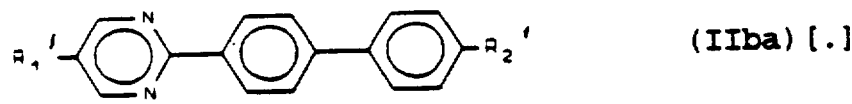 (IIba) [.]

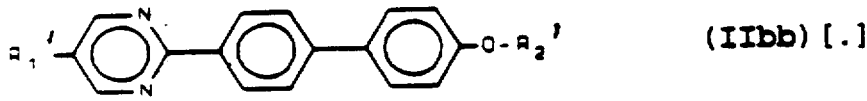 (IIbb) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

(IIbc) [.]

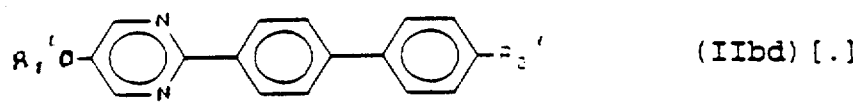  (IIbd) [.]

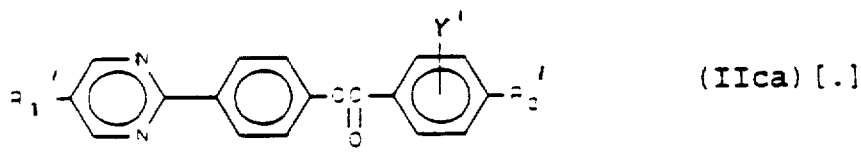  (IIca) [.]

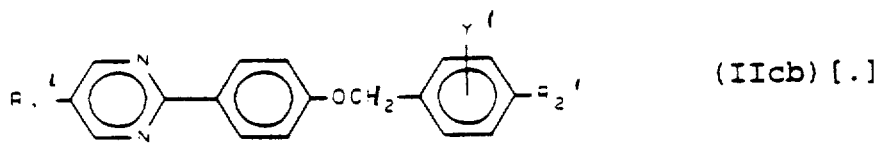  (IIcb) [.]

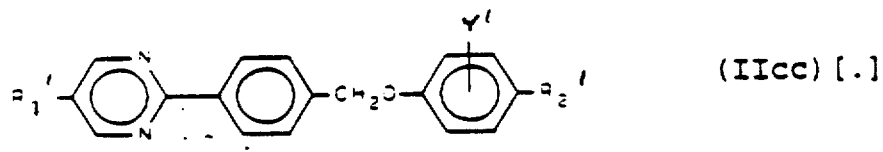  (IIcc) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

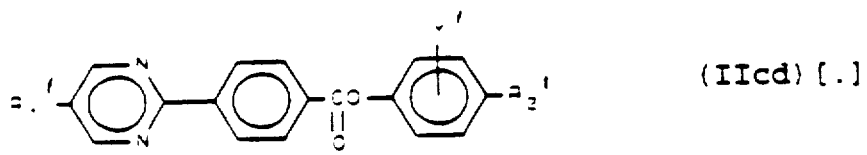 (IIcd) [.]

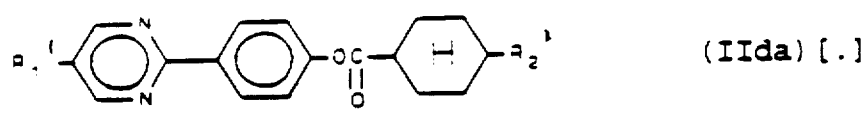 (IIda) [.]

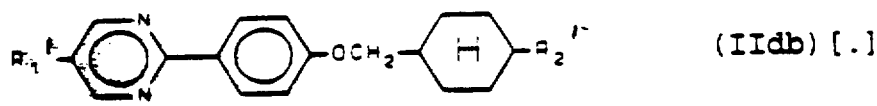 (IIdb) [.]

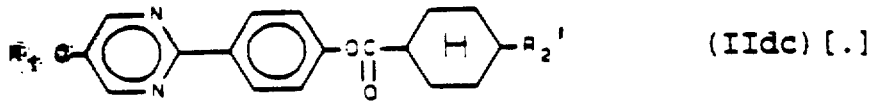 (IIdc) [.]

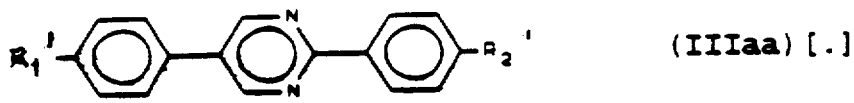 (IIIaa) [.]

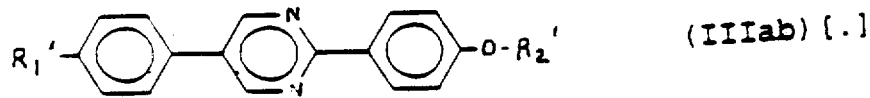 (IIIab) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

(IIIba) [.]

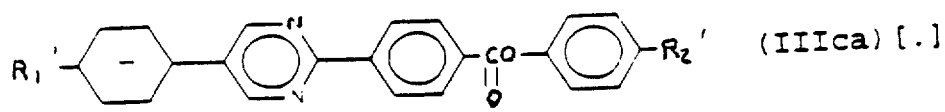 (IIIca) [.]

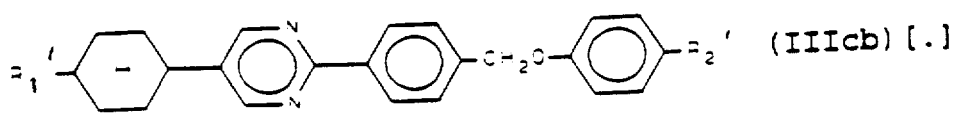 (IIIcb) [.]

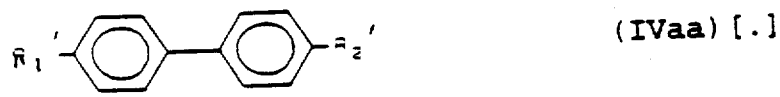 (IVaa) [.]

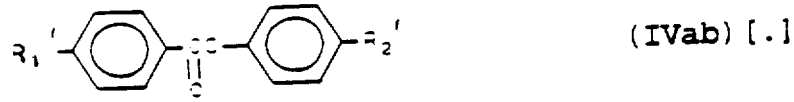 (IVab) [.]

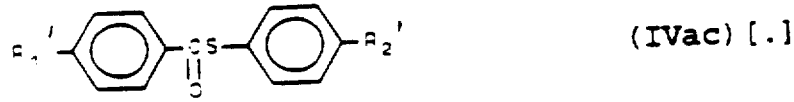 (IVac) [.]

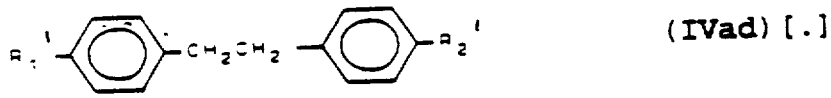 (IVad) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

(IVae) [.]

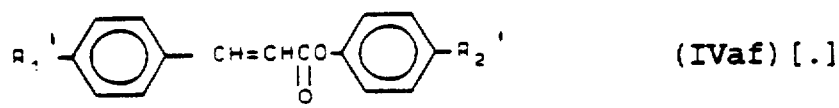 (IVaf) [.]

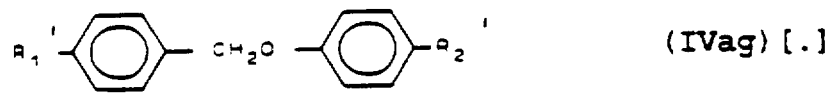 (IVag) [.]

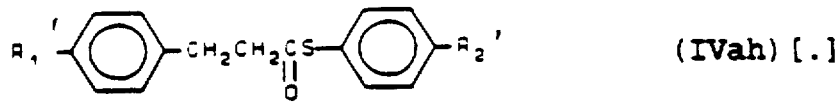 (IVah) [.]

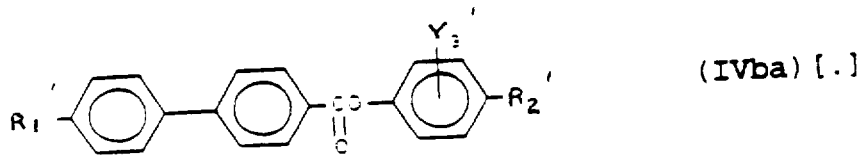 (IVba) [.]

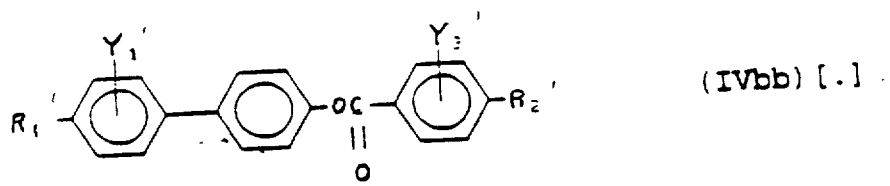 (IVbb) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144
Forms (IIaa)-(IXbb), (Continued)

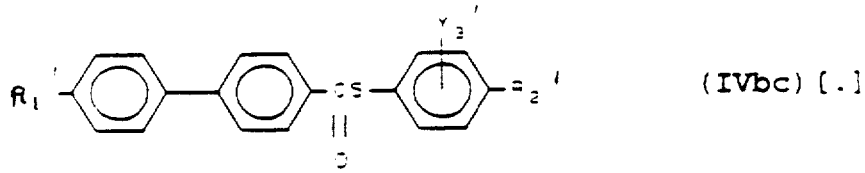 (IVbc) [.]

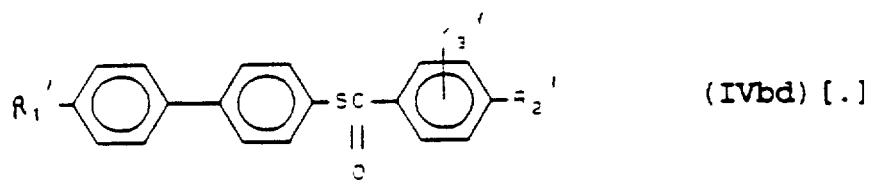 (IVbd) [.]

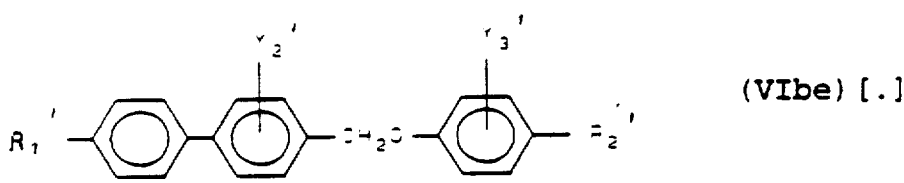 (VIbe) [.]

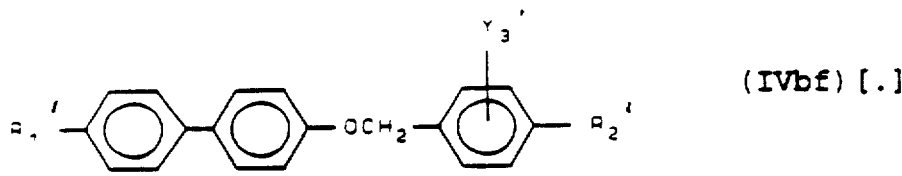 (IVbf) [.]

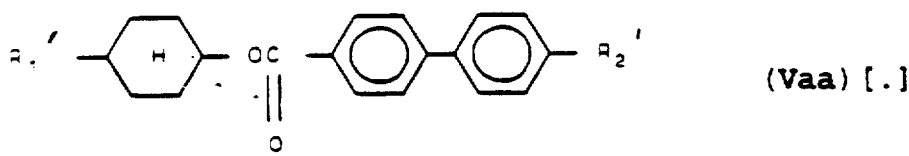 (Vaa) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

(Vab) [.]

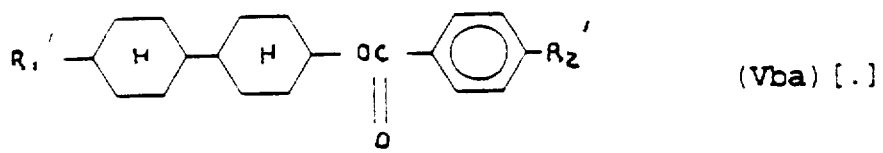 (Vba) [.]

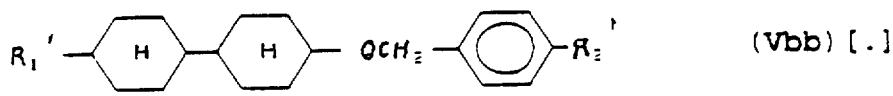 (Vbb) [.]

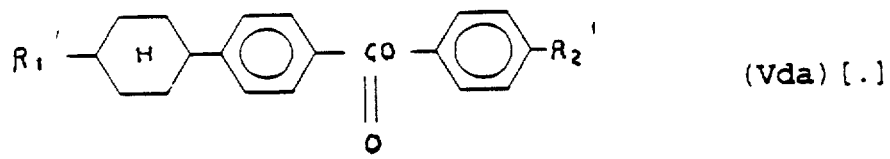 (Vda) [.]

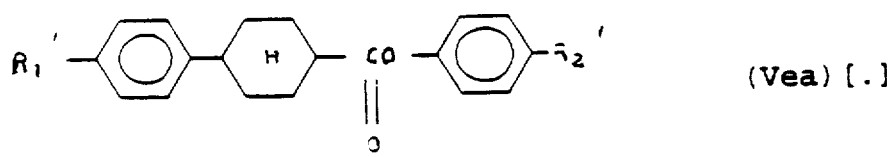 (Vea) [.]

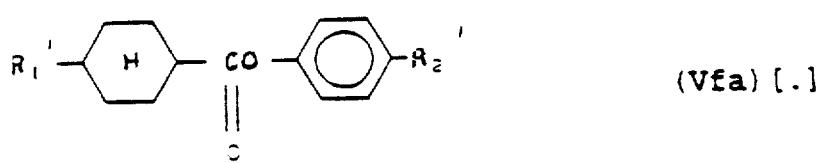 (Vfa) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMNS 139-144

Forms (IIaa)-(IXbb), (Continued)

(VIIaa) [.]

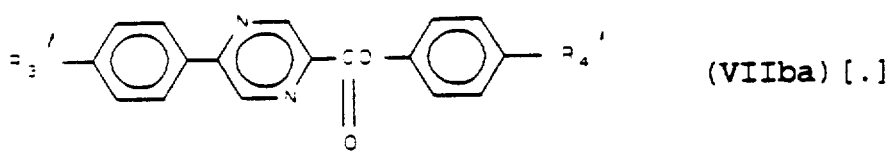 (VIIba) [.]

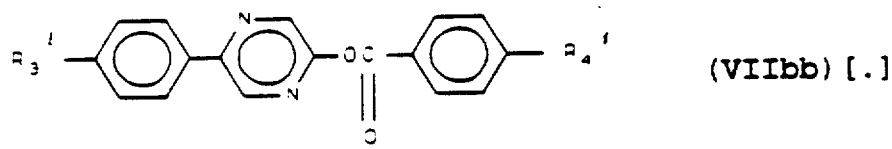 (VIIbb) [.]

 (VIIIaa) [.]

 (VIIIab) [.]

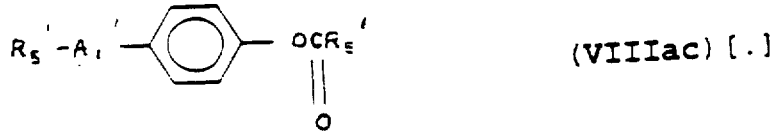 (VIIIac) [.]

COLUMNS 139-144
Forms (IIaa)-(IXbb), (Continued)
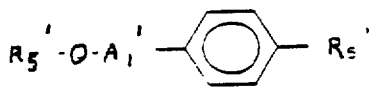 (VIIIad) [.]
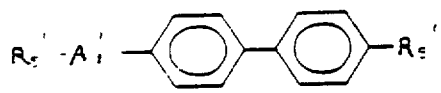 (VIIIba) [.]
 (VIIIbb) [.]
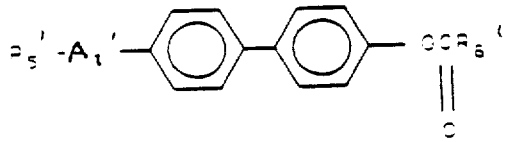 (VIIIbc) [.]
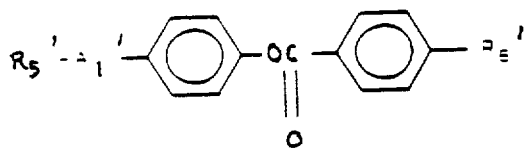 (VIIIbd) [.]
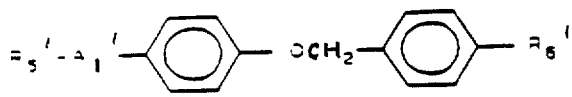 (VIIIbe) [.]
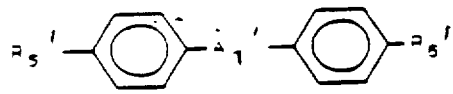 (VIIIca) [.]

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

<u>COLUMNS 139-144</u>
Forms (IIaa)-(IXbb), (Continued)

(VIIIcb) [.]

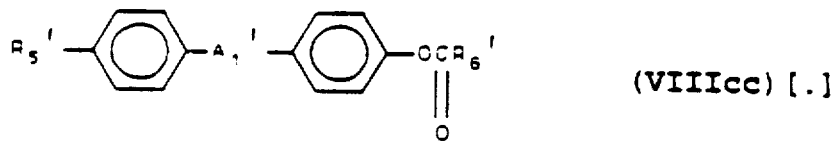    (VIIIcc) [.]

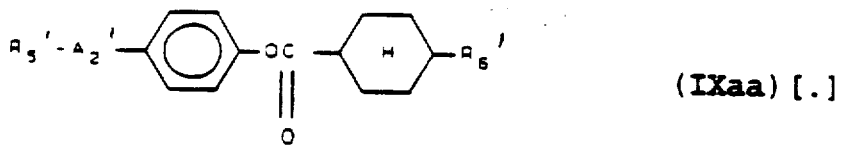    (IXaa) [.]

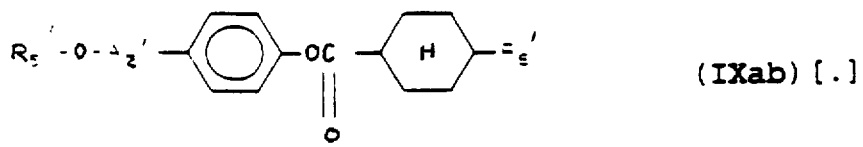    (IXab) [.]

    (IXac) [.]

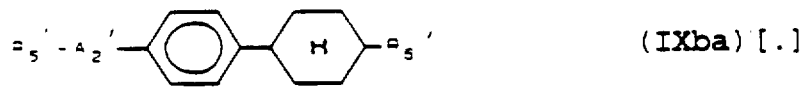    (IXba) [.]

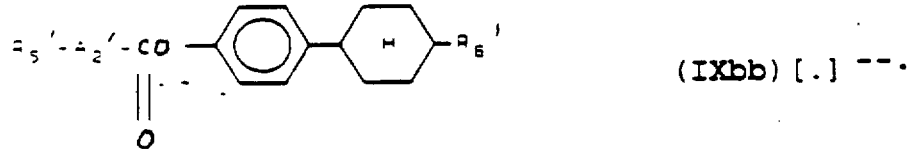    (IXbb) [.] --.

UNITED STATES PATENT AND TRADEMARK OFFICE
CERTIFICATE OF CORRECTION

PATENT NO. : 5,244,596
DATED : September 14, 1993
INVENTOR(S) : TAKAO TAKIGUCHI ET AL.

It is certified that error appears in the above-identified patent and that said Letters Patent is hereby corrected as shown below:

COLUMN 144

Line 27, "$Y'_1$, $Y'_2$ and $Y'_3$" should read --$Y_1'$, $Y_2'$ and $Y_3'$--.
Line 28, "$A'_1$ and $A'_2$" should read --$A_1'$ and $A_2'$--.
Line 40, "$R'_1$ and $R_2$" should read --$R_1'$ and $R_2'$--.

COLUMN 146

Line 21, "claim" should read --claim 22--.

Signed and Sealed this

Eighteenth Day of October, 1994

Attest:

BRUCE LEHMAN

*Attesting Officer*  *Commissioner of Patents and Trademarks*